(12) United States Patent
Sutton et al.

(10) Patent No.: US 10,172,830 B2
(45) Date of Patent: Jan. 8, 2019

(54) PYRAZOLONE COMPOUNDS HAVING HUMAN NEUTROPHIL ELASTASE INHIBITORY PROPERTIES

(71) Applicant: CHIESI FARMACEUTICI S.P.A., Parma (IT)

(72) Inventors: Jonathan Mark Sutton, Harlow (GB); Robert Andrew Heald, Harlow (GB); Andrew Stephen Robert Jennings, Harlow (GB); Carmelida Capaldi, Parma (IT); Elisabetta Armani, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 0 days.

(21) Appl. No.: 15/606,154

(22) Filed: May 26, 2017

(65) Prior Publication Data

US 2017/0340611 A1    Nov. 30, 2017

(30) Foreign Application Priority Data

May 31, 2016   (EP) .................................... 16172201

(51) Int. Cl.

| | |
|---|---|
| *A61K 31/4152* | (2006.01) |
| *A61K 31/4155* | (2006.01) |
| *C07D 401/14* | (2006.01) |
| *C07D 403/04* | (2006.01) |
| *C07D 403/14* | (2006.01) |
| *C07D 413/14* | (2006.01) |
| *A61K 31/277* | (2006.01) |
| *C07D 231/44* | (2006.01) |
| *C07D 249/08* | (2006.01) |
| *C07D 401/04* | (2006.01) |

(52) U.S. Cl.
CPC ........ *A61K 31/4152* (2013.01); *A61K 31/277* (2013.01); *C07D 231/44* (2013.01); *C07D 249/08* (2013.01); *C07D 401/04* (2013.01); *C07D 401/14* (2013.01); *C07D 403/04* (2013.01); *C07D 403/14* (2013.01); *C07D 413/14* (2013.01)

(58) Field of Classification Search
CPC ............ A61K 31/4152; A61K 31/4155; C07D 401/14; C07D 403/04; C07D 403/14; C07D 413/14
USPC .......... 514/218, 254.05, 278, 316, 326, 341, 514/364, 374, 378, 404; 540/575; 544/371; 546/16, 187, 208, 276.1; 548/143, 236, 247, 312.4, 365.4
See application file for complete search history.

(56) References Cited

U.S. PATENT DOCUMENTS

2014/0018345 A1   1/2014   Capaldi et al.

FOREIGN PATENT DOCUMENTS

| EP | 2 740 728 | 6/2014 |
|---|---|---|
| WO | 2015/124563 | 8/2015 |
| WO | 2016/096638 | 6/2016 |

OTHER PUBLICATIONS

European Search Report in Application No. 16172201.2 dated Jul. 27, 2016.
International Search Report in Application No. PCT/EP2017/062756 dated Jul. 13, 2017.

*Primary Examiner* — Brenda L Coleman
(74) *Attorney, Agent, or Firm* — Oblon, McClelland, Maier & Neustadt, L.L.P.

(57) ABSTRACT

Pyrazolone derivatives of formula (I) defined herein exhibit human neutrophil elastase inhibitory properties and are useful for the treatment of diseases or conditions in which HNE is implicated.

15 Claims, No Drawings

PYRAZOLONE COMPOUNDS HAVING HUMAN NEUTROPHIL ELASTASE INHIBITORY PROPERTIES

CROSS REFERENCES TO RELATED APPLICATIONS

This application claims priority to European Patent Application No. 16172201.2, filed on May 31, 2016, which is incorporated herein by reference in its entirety.

BACKGROUND OF THE INVENTION

Field of the Invention

The present invention relates to pyrazolone derivatives having human neutrophil elastase inhibitory properties, and the therapeutic use of such derivatives.

Discussion of the Background

Human neutrophil elastase (HNE) is a 32 kDa serine proteinase found in the azurophilic granules of neutrophils. It has a role in the degradation of a wide range of extracellular matrix proteins, including fibronectin, laminin, proteoglycans, Type III and Type IV collagens as well as elastin (see Bieth, G. in *Regulation of Matrix accumulation*, Mecham, R. P. (Eds), Academic Press, NY, USA 1986, 217-306, which is incorporated herein by reference in its entirety). HNE has long been considered to play an important role in homeostasis through repair and disposal of damaged tissues via degradation of the tissue structural proteins. It is also relevant in the defense against bacterial invasion by means of degradation of the bacterial body. In addition to its effects on matrix tissues, HNE has been implicated in the upregulation of IL-8 gene expression and also induces IL-8 release from the epithelial cells of the lung. In animal models of Chronic Obstructive Pulmonary Disease induced by tobacco smoke exposure both small molecule inhibitors and protein inhibitors of HNE inhibit the inflammatory response and the development of emphysema (see Wright, J. L. et al. *Am. J. Respir. Crit. Care Med.* 2002, 166, 954-960; Churg, A. et al. *Am. J. Respir. Crit. Care Med.* 2003, 168, 199-207, which are incorporated herein by reference in their entireties).

Thus, HNE may play a role both in matrix destruction and in amplifying inflammatory responses in chronic respiratory diseases where neutrophil influx is a characteristic feature. Indeed, HNE is believed to play a role in several pulmonary diseases, including chronic obstructive pulmonary disease (COPD), cystic fibrosis (CF), acute respiratory distress syndrome (ARDS), pulmonary emphysema, pneumonia and lung fibrosis. It is also implicated in several cardiovascular diseases in which tissue remodeling is involved, for example, in heart failure and the generation of ischemic tissue injury following acute myocardial infarction.

COPD is an umbrella term encompassing three different pathological conditions, all of which contribute to limitation of airflow: chronic bronchitis, emphysema and small-airway disease. Generally all three will exist to varying extents in patients presenting with COPD, and all three may be due to neutrophil-mediated inflammation, as supported by the increased number of neutrophils observed in bronchoalveolar leakage (BAL) fluids of COPD patients (see Thompson, A. B.; Daughton, D.; et al. *Am. Rev. Respir. Dis.* 1989, 140, 1527-1537, which is incorporated herein by reference in its entirety). The major pathogenic determinant in COPD has long been considered to be the protease-anti-protease balance (also known as the "elastase:anti-elastase hypothesis"), in which an imbalance of HNE and endogenous antiproteases such as α1-antitrypsin ($\alpha_1$-AT), secretory leukocyte protease inhibitor (SLPI) and pre-elafin leads to the various inflammatory disorders of COPD. Individuals that have a genetic deficiency of the protease inhibitor α1-antitrypsin develop emphysema that increases in severity over time (see Laurrell, C. B.; Erikkson, S *Scand. J. Clin. Invest.* 1963 15, 132-140, which is incorporated herein by reference in its entirety). An excess of HNE is therefore destructive, leading to the breakdown of pulmonary morphology with loss of elasticity and destruction of alveolar attachments of airways in the lung (emphysema) whilst simultaneously increasing microvascular permeability and mucus hypersecretion (chronic bronchitis).

Several human neutrophil inhibitors have been disclosed so far. In particular, WO2011/110858, WO2011/110859, WO 2014/095700, and WO 2015/091281, which are incorporated herein by reference in their entireties, describe pyrimidine derivatives having human neutrophil elastase inhibitory properties.

Although several HNE inhibitors have been disclosed so far as above reported, there is still a need for further HNE inhibitors. Particularly, there is still a need for further HNE inhibitors endowed with a high potency for HNE enzyme inhibition.

Particularly advantageous would also be the identification of further HNE inhibitors endowed with a high potency for HNE enzyme inhibition and which would show an appropriate developability profile as an inhalation treatment.

SUMMARY OF THE INVENTION

Accordingly, it is one object of the present invention to provide novel to pyrazolone derivatives having human neutrophil elastase inhibitory properties.

It is another object of the present invention to provide novel methods of treating and/or preventing certain diseases by administering such a pyrazolone derivative.

These and other objects, which will become apparent during the following detailed description, have been achieved by the inventors' discovery of the compounds of formula (I) described below.

Thus, in one aspect the present invention provides a compound of formula (I) or a pharmaceutically acceptable salt thereof:

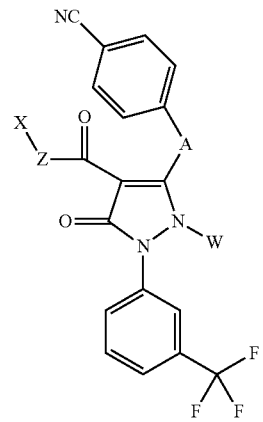

wherein
Z is —O— or —NH;
W is —H or ($C_1$-$C_4$)alkyl;
A is selected from the group consisting of

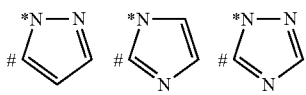

X is selected from the group consisting of —(C$_1$-C$_6$)alkyl, —(C$_2$-C$_6$)alkylene-NR$_d$R$_e$, —(C$_2$-C$_6$)alkylene-N$^+$R$_a$R$_b$R$_c$, linear or branched —(C$_1$-C$_4$)alkylene-aryl, linear or branched —(C$_2$-C$_4$)alkylene-heteroaryl; or is selected from the group consisting of

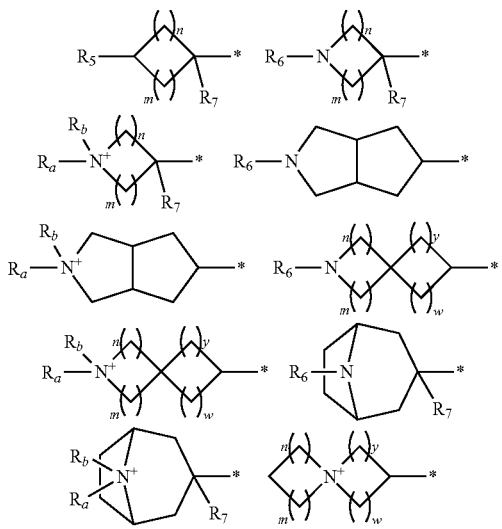

or is selected from a group consisting of

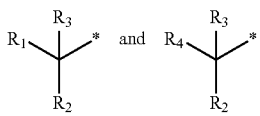

R$_1$ is selected from the group consisting of

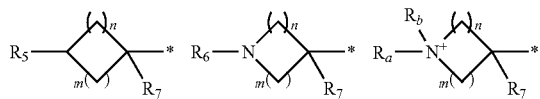

n is an integer from 1 to 4;
m is an integer from 1 to 4;
t is 0 or an integer from 1 to 4;
y is an integer from 1 to 4;
w is an integer from 1 to 4;
R$_2$ is —H or linear or branched —(C$_1$-C$_4$)alkyl;
R$_3$ is —H, or is selected from a group consisting of linear or branched —(C$_1$-C$_4$)alkyl or R$_2$ and R$_3$ may form together a —(C$_3$-C$_6$)cycloalkyl;
R$_4$ is selected from the group consisting of heteroaryl, -arylene-(C$_1$-C$_4$)alkylene-NR$_d$R$_e$, —arylene-(C$_1$-C$_4$)alkylene-N$^+$R$_a$R$_b$R$_c$, —heteroarylene-(C$_1$-C$_4$)alkylene-NR$_d$R$_e$, -heteroarylene-(C$_1$-C$_4$)alkylene-N$^+$R$_a$R$_b$R$_c$ or is selected from the group consisting of

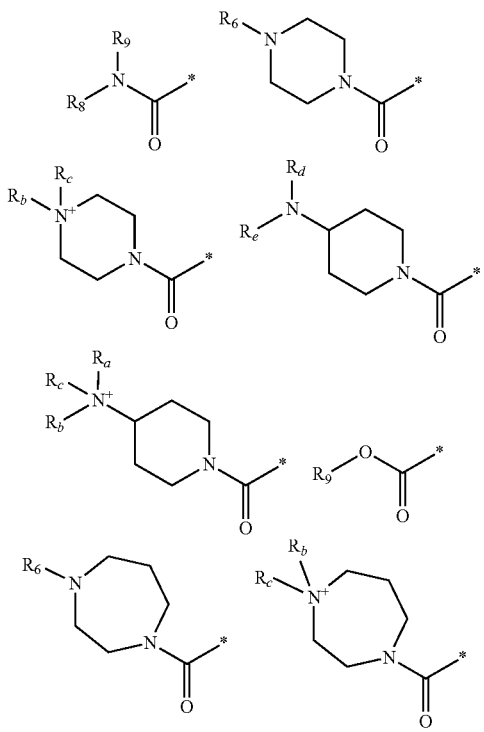

R$_5$ is —H or is selected from the group consisting of —(CH$_2$)$_t$-heteroaryl, aryl-(C$_1$-C$_4$)alkyleneoxy-, linear or branched (C$_1$-C$_4$)alkyl-OC(O)—NH—, —(CH$_2$)$_t$—NR$_d$R$_e$, —(CH$_2$)$_t$—N$^+$R$_a$R$_b$R$_c$, -heteroaryl-(CH$_2$)$_t$—N$^+$R$_a$R$_b$R$_c$, —C(O)—N(R$_{10}$)(C$_1$-C$_4$)alkylene-NR$_d$R$_e$, —C(O)N(R$_{10}$)(C$_1$-C$_4$)alkylene-N$^+$R$_a$R$_b$R$_c$, —C(O)O(C$_1$-C$_4$)alkylene-NR$_d$R$_e$, —C(O)O(C$_1$-C$_4$)alkylene-N$^+$R$_a$R$_b$R$_c$, —O—C(O)—(C$_1$-C$_4$)alkylene-NR$_d$R$_e$, —O—C(O)—(C$_1$-C$_4$)alkylene-N$^+$R$_a$R$_b$R$_c$, —(CH$_2$)$_t$NHC(O)—(C$_1$-C$_4$)alkylene-NR$_d$R$_e$, —(CH$_2$)$_t$NHC(O)—(C$_1$-C$_4$)alkylene-N$^+$R$_a$R$_b$R$_c$, or is selected from a group consisting of

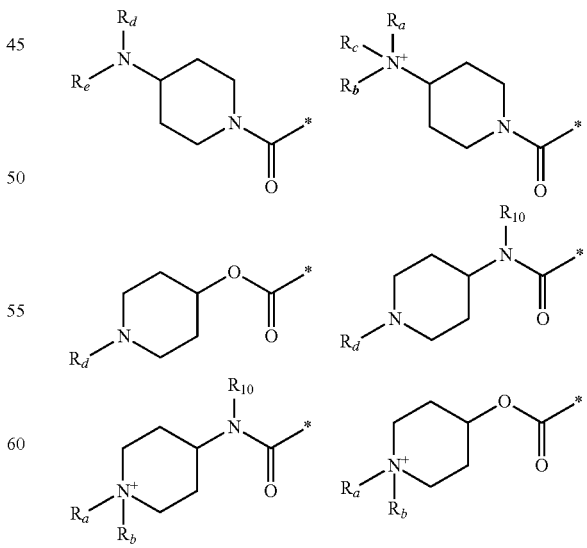

R$_6$ is —H or is selected from the group consisting of —(C$_1$-C$_4$)alkyl, aryl-(C$_1$-C$_4$)alkylene-OC(O)—, CF$_3$C (O)—, aryl-($C_1$-$C_4$)alkylene-, linear or branched ($C_1$-$C_4$) alkyl-OC(O)—, —C(O)—($C_1$-$C_4$)alkylene-$NR_dR_e$, —C(O)—($C_1$-$C_4$)alkylene-$N^+R_aR_bR_c$, —C(O)-heterocycloalkyl, —C(O)O—($C_1$-$C_4$)alkylene-$NR_dR_e$, —C(O)O—($C_1$-$C_4$)alkylene-$N^+R_aR_bR_c$, —C(O)—N($R_{10}$)($C_1$-$C_4$)alkylene-$NR_dR_e$, —C(O)N($R_{10}$)($C_1$-$C_4$)alkylene-$N^+R_aR_bR_c$;

$R_a$ is —($C_1$-$C_4$)alkyl;
$R_b$ is —($C_1$-$C_4$)alkyl;
$R_c$ is selected from a group consisting of —($C_1$-$C_4$)alkyl, aryl-($C_1$-$C_4$)alkylene- and heteroaryl-($C_1$-$C_4$)alkylene-, wherein said heteroaryl-($C_1$-$C_4$)alkylene may be optionally substituted by one or more —($C_1$-$C_4$)alkyl groups;
$R_d$ is —H or —($C_1$-$C_4$)alkyl;
$R_e$ is —H or —($C_1$-$C_4$)alkyl;
$R_7$ is —H or —($C_1$-$C_4$)alkyl;
$R_8$ is —H or —($C_1$-$C_4$)alkyl;
$R_9$ is selected from a group consisting of -heterocycloalkyl, heterocycloalkyl-($C_1$-$C_4$)alkylene-, ($C_1$-$C_4$)alkylene-$NR_dR_e$ and ($C_1$-$C_4$)alkylene-$N^+R_aR_bR_c$;
$R_{10}$ is —H or —($C_1$-$C_4$)alkyl;
wherein any of such heterocycloalkyl, aryl, heteroaryl, heterocycloalkyl-($C_1$-$C_4$)alkylene- and aryl-($C_1$-$C_4$)alkylene may be optionally substituted by one or more groups independently selected from —($C_1$-$C_4$)alkyl and —$OR_7$ and wherein the nitrogen atom in the heterocycloalkyl, aryl, heteroaryl, heterocycloalkyl-($C_1$-$C_4$)alkylene- and aryl-($C_1$-$C_4$)alkylene groups may be quaternized.

The compounds of formula (I) can be prepared in the form of salts, particularly pharmaceutically acceptable salts, N-oxides, hydrates, solvates and polymorphs thereof. Any reference to a compound herein, or reference to "compounds of the invention", "compounds of formula (I)", and the like includes such compounds whether or not in salt, N-oxide, hydrate, solvate or polymorphic form.

The compounds of the present invention can be used in the treatment or prevention of diseases in which HNE is implicated, for example chronic obstructive pulmonary disease (COPD), bronchiectasis, chronic bronchitis, lung fibrosis, pneumonia, acute respiratory distress syndrome (ARDS), pulmonary emphysema, smoking-induced emphysema and cystic fibrosis.

Hence other aspects of the invention are (i) a pharmaceutical composition comprising a compound of the invention and a pharmaceutically acceptable carrier or excipient; and (ii) the use of a compound of the invention for the manufacture of a medicament for the treatment or prevention of a disease or condition in which HNE is implicated.

DETAILED DESCRIPTION OF THE PREFERRED EMBODIMENTS

The term "($C_a$-$C_b$)alkyl" wherein a and b are integers refers to a straight or branched chain alkyl radical having from a to b carbon atoms. Thus when a is 1 and b is 6, for example, the term includes methyl, ethyl, n-propyl, isopropyl, n-butyl, isobutyl, sec-butyl, t-butyl, n-pentyl and n-hexyl.

The term "($C_a$-$C_b$) cycloalkyl", wherein a and b are integers, refers to saturated monocyclic, bicyclic or tricyclic hydrocarbon groups containing from a to b ring carbon atoms, as appropriate. Examples include cyclopropyl, cyclobutyl, cyclopentyl, cyclohexyl and cycloheptyl, adamantyl.

The term "heterocyclic" relates to a saturated mono-, bi- or tri-cyclic non-aromatic radical containing one or more heteroatoms selected from S, N and O. In the case of bicyclic heterocyclic systems, included within the scope of the term are fused, spiro and bridged bicyclic systems, such as for example a quinuclidine ring. In particular, the term "$C_a$-$C_b$ heterocycloalkyl" refers to monocyclic ($C_a$-$C_b$)cycloalkyl groups, in which at least one ring carbon atom is replaced by a heteroatom (e.g. N, NH, S or O). Examples of ($C_a$-$C_b$) heterocycloalkyl include pyrrolidinyl, thiazolidinyl, piperazinyl, piperidinyl, morpholinyl, thiomorpholinyl.

By analogy, the expression "heterocycloalkylenee" refers to a divalent heterocyclic radical as above defined. In particular, the expression "($C_a$-$C_b$)heterocycloalkylenee" refers to a divalent ($C_a$-$C_b$)heterocycloalkyl radical (such as for example pyrrolidinene) wherein "($C_a$-$C_b$)heterocycloalkyl group is as above defined.

The expression "heteroaryl" refers to mono or bi-cyclic ring systems with 5 to 11 ring atoms, in which at least one ring is aromatic and in which at least one ring atom is a heteroatom (e.g. N, NH, S or O).

Examples of suitable 5,6-membered heteroaryl monocyclic systems include, for instance thiophene (thiophenyl), pyrrole (pyrrolyl), pyrazole (pyrazolyl), imidazole (imidazolyl), isoxazole (isoxazolyl), oxazole (oxazolyl), isothiazole (isothiazolyl), thiazole (thiazolyl), pyridine (pyridinyl), pyrimidine (pyrimidinyl), pyridazine (pyridazinyl) and furan (furanyl) radicals and the like.

Examples of suitable bi-cyclic heteroaryl ring systems include quinolones (quinolonyl), isoquinolines (isoquinolinyl), indole (indolyl), isoindole (isoindolyl), indolizine (indolizinyl), benzimidazole (benzimidazolyl), azabenzimidazole (azabenzimidazolyl), benzoxazole (benzoxazolyl) and benzothiazole (benzthiazolyl) radicals and the like.

Throughout the specification the use of an asterisk "*" and "#" in the definition of a structural formula, indicates the points of attachment for the radical groups to the rest of the molecule. In particular, the nitrogen atom indicated with * in group A is directly linked to the carbon atom of fragment

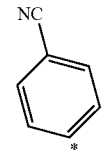

also indicated with *, and the carbon atom indicated with # in group A is directly linked to the carbon atom of fragment

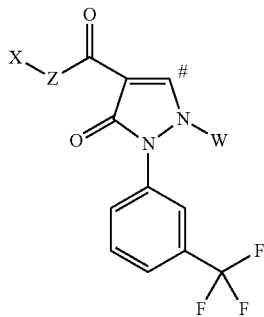

also indicated with #.

The term "Pharmaceutically acceptable salts" refers to derivatives of compounds of formula (I) wherein the parent compound is modified by converting any of the free acid or basic group, if present, into the corresponding addition salt with any base or acid conventionally intended as being pharmaceutically acceptable.

Where the compounds of the invention have at least one stereogenic center, they can exist as enantiomers. When the compounds according to the invention possess two or more stereogenic centers, they can additionally exist as diastereoisomers. It is to be understood that all such isomers and mixtures thereof in any proportion are encompassed within the scope of the present invention.

The absolute configuration for carbon (1) is assigned on the basis of Cahn-Ingold-Prelog nomenclature based on groups' priorities.

It is to be understood that all preferred groups or embodiments described here below for compounds of formula (I) may be combined among each other mutatis mutandis.

In one embodiment for compounds of formula (I), Z is —O—.

In another embodiment Z is —NH.
In another embodiment W is —H or ($C_1$-$C_4$)alkyl;
In another embodiment, A is

In another embodiment, A is

In another embodiment X is selected from the group consisting of —($C_1$-$C_6$)alkyl, —($C_2$-$C_6$)alkylene-$NR_dR_e$, —($C_2$-$C_6$)alkylene-$N^+R_aR_bR_c$, linear or branched —($C_1$-$C_4$)alkylene-aryl and linear or branched —($C_2$-$C_4$)alkylene-heteroaryl.

In another embodiment X is

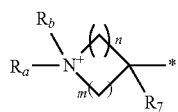

$R_a$ and $R_b$ are independently —($C_1$-$C_4$)alkyl; n is 2; m is 2; $R_7$ is —H or —($C_1$-$C_4$)alkyl.

In another embodiment X is

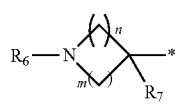

$R_6$ is —H or is selected from the group consisting of —($C_1$-$C_4$)alkyl, —C(O)—($C_1$-$C_4$)alkylene-$NR_dR_e$, —C(O)—($C_1$-$C_4$)alkylene-$N^+R_aR_bR_c$ and —C(O)-heterocycloalkyl, wherein the heterocycloalkyl may be optionally substituted by one or more —($C_1$-$C_4$)alkyl and the nitrogen atom in the heterocycloalkyl may be quaternized; $R_d$ and $R_e$ are independently —H or —($C_1$-$C_4$)alkyl; $R_a$ is —($C_1$-$C_4$)alkyl; $R_b$ is —($C_1$-$C_4$)alkyl; $R_c$ is selected from a group consisting of —($C_1$-$C_4$)alkyl, aryl-($C_1$-$C_4$)alkylene- and heteroaryl-($C_1$-$C_4$)alkylene-, wherein said heteroaryl-($C_1$-$C_4$)alkylene may be optionally substituted by one or more —($C_1$-$C_4$)alkyl groups; n is 2; m is 2; $R_7$ is —H or —($C_1$-$C_4$)alkyl.

In another embodiment X is

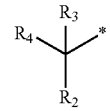

$R_2$ and $R_3$ are independently —H or linear or branched —($C_1$-$C_4$)alkyl; $R_4$ is heteroaryl optionally substituted by one or more —($C_1$-$C_4$)alkyl, wherein the nitrogen atom in the heteroaryl group may be quaternized.

In another embodiment X is

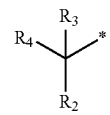

$R_2$ and $R_3$ are independently —H or linear or branched —($C_1$-$C_4$)alkyl; $R_4$ is -heteroarylene-($C_1$-$C_4$)alkylene-$NR_dR_e$ and -heteroarylene-($C_1$-$C_4$)alkylene-$N^+R_aR_bR_c$; $R_d$ and $R_e$ are independently —H or —($C_1$-$C_4$)alkyl; $R_a$ is —($C_1$-$C_4$)alkyl; $R_b$ is —($C_1$-$C_4$)alkyl; $R_c$ is selected from a group consisting of —($C_1$-$C_4$)alkyl, aryl-($C_1$-$C_4$)alkylene- and heteroaryl-($C_1$-$C_4$)alkylene-, wherein said heteroaryl-($C_1$-$C_4$)alkylene may be optionally substituted by one or more —($C_1$-$C_4$)alkyl groups.

In another embodiment X is

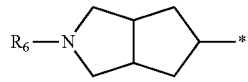

$R_6$ is linear or branched ($C_1$-$C_4$)alkyl-OC(O)—.
In another embodiment X is

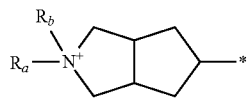

$R_a$ and $R_b$ are independently —($C_1$-$C_4$)alkyl.
In another embodiment X is

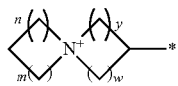

n is 1, m is 2, y is 2, w is 2.

In another embodiment X is

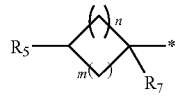

R₅ is —H or selected from —(CH₂)$_t$-heteroaryl and —(CH₂)$_t$—N⁺R$_a$R$_b$R$_c$; t is 1; R$_a$ and R$_b$ are independently —(C₁-C₄)alkyl; R$_c$ is selected from a group consisting of —(C₁-C₄)alkyl, aryl-(C₁-C₄)alkylene- and heteroaryl-(C₁-C₄)alkylene-, wherein said heteroaryl and heteroaryl-(C₁-C₄)alkylene may be optionally substituted by one or more —(C₁-C₄)alkyl groups and wherein the nitrogen atom in the heteroaryl may be quaternized; R₇ is —H or —(C₁-C₄)alkyl; n is 1 or 2; m is 1 or 2.

In another embodiment X is

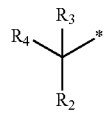

R₂ is —H or linear or branched —(C₁-C₄)alkyl; R₃ is —H; R₄ is

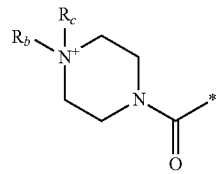

R$_b$ is —(C₁-C₄)alkyl; R$_c$ is selected from a group consisting of —(C₁-C₄)alkyl, aryl-(C₁-C₄)alkylene- and heteroaryl-(C₁-C₄)alkylene-, wherein said heteroaryl-(C₁-C₄)alkylene may be optionally substituted by one or more —(C₁-C₄)alkyl groups.

In another embodiment X is

R$_a$ and R$_b$ are independently —(C₁-C₄)alkyl; R₇ is —H or —(C₁-C₄)alkyl.

In another embodiment X is

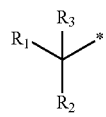

R₂ is —H or linear or branched —(C₁-C₄)alkyl; R₃ is —H; R₁ is

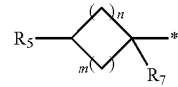

R₅ is —(CH₂)$_t$—N⁺R$_a$R$_b$R$_c$, wherein R$_a$ is —(C₁-C₄)alkyl; R$_b$ is —(C₁-C₄)alkyl; R$_c$ is selected from a group consisting of —(C₁-C₄)alkyl, aryl-(C₁-C₄)alkylene- and heteroaryl-(C₁-C₄)alkylene-, wherein said heteroaryl-(C₁-C₄)alkylene may be optionally substituted by one or more —(C₁-C₄)alkyl groups; R₇ is —H or —(C₁-C₄)alkyl; t is 0; n is 2; m is 2.

In another embodiment X is

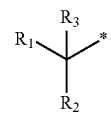

R₂ is —H or linear or branched —(C₁-C₄)alkyl; R₃ is —H; R₁ is

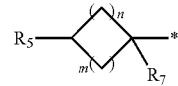

R₅ is —(CH₂)$_t$-heteroaryl, wherein the heteroaryl may be optionally substituted by one or more —(C₁-C₄)alkyl and the nitrogen atom in the heteroaryl may be quaternized; t is 0 or 1; n is 2; m is 2.

In another embodiment X is

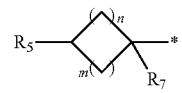

R₅ is —C(O)N(R₁₀)(C₁-C₄)alkylene-N⁺R$_a$R$_b$R$_c$, wherein R$_a$ is —(C₁-C₄)alkyl; R$_b$ is —(C₁-C₄)alkyl; R$_c$ is selected from a group consisting of —(C₁-C₄)alkyl, aryl-(C₁-C₄)alkylene- and heteroaryl-(C₁-C₄)alkylene-, wherein said heteroaryl-(C₁-C₄)alkylene may be optionally substituted by one or more —(C₁-C₄)alkyl groups; R₁₀ is —H or —(C₁-C₄)alkyl; n is 1 or 2; m is 1 or 2; R₇ is —H.

In another embodiment X is

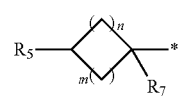

R₅ is —(CH₂)$_t$NHC(O)—(C₁-C₄)alkylene-N⁺R$_a$R$_b$R$_c$, wherein R$_a$ is —(C₁-C₄)alkyl; R$_b$ is —(C₁-C₄)alkyl; R$_c$ is selected from a group consisting of —(C₁-C₄)alkyl, aryl-(C₁-C₄)alkylene- and heteroaryl-(C₁-C₄)alkylene-, wherein said heteroaryl-(C₁-C₄)alkylene may be optionally substituted by one or more —(C₁-C₄)alkyl groups; t is 0 or 1, n is 2, m is 2, R₇ is —H.

In another embodiment X is

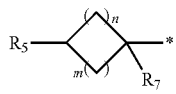

$R_5$ is

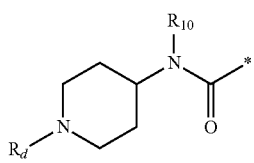

$R_{10}$ is —H, $R_d$ is —$(C_1$-$C_4)$alkyl, n is 2, m is 2, $R_7$ is —H.
In another embodiment X is

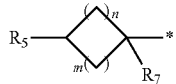

$R_5$ is

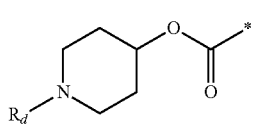

$R_d$ is —$(C_1$-$C_4)$alkyl, n is 2, m is 2, $R_7$ is —H.
In another embodiment X is

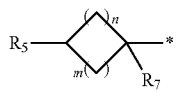

$R_5$ is

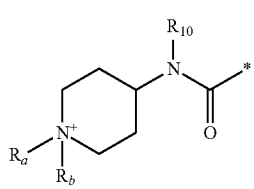

$R_{10}$ is —H, $R_a$ and $R_b$ are independently —$(C_1$-$C_4)$alkyl, n is 1 or 2, m is 1 or 2, $R_7$ is —H.
In another embodiment X is

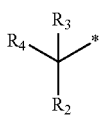

$R_2$ is —H or linear or branched —$(C_1$-$C_4)$alkyl; $R_3$ is —H; $R_4$ is

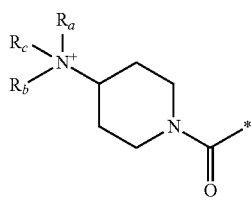

$R_a$ and $R_b$ are independently —$(C_1$-$C_4)$alkyl; $R_c$ is selected from a group consisting of —$(C_1$-$C_4)$alkyl, aryl-$(C_1$-$C_4)$alkylene- and heteroaryl-$(C_1$-$C_4)$alkylene-, wherein said heteroaryl-$(C_1$-$C_4)$alkylene may be optionally substituted by one or more —$(C_1$-$C_4)$alkyl groups.
In another embodiment X is

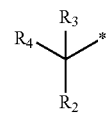

$R_2$ is —H or linear or branched —$(C_1$-$C_4)$alkyl; $R_3$ is —H; $R_4$ is

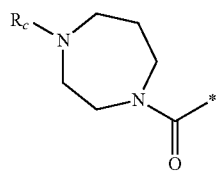

$R_6$ is —$(C_1$-$C_4)$alkyl.
In another embodiment X is

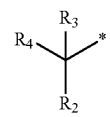

$R_2$ is —H or linear or branched —$(C_1$-$C_4)$alkyl; $R_3$ is —H; $R_4$ is

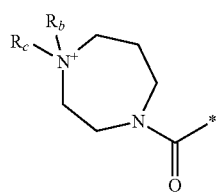

$R_b$ and $R_c$ are independently —$(C_1$-$C_4)$alkyl.
In another embodiment X is

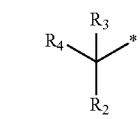

$R_5$ is

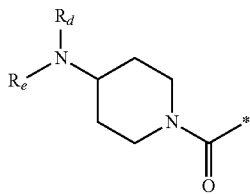

n is 2, m is 2, $R_7$ is —H, $R_d$ and $R_e$ are independently —H or —$(C_1-C_4)$alkyl.

In another embodiment X is

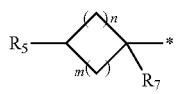

$R_5$ is

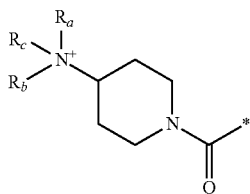

n is 2, m is 2, $R_7$ is —H, $R_a$, $R_b$ and $R_c$ are independently —$(C_1-C_4)$alkyl.

In another embodiment X is

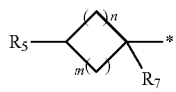

$R_5$ is —C(O)O$(C_1-C_4)$alkylene-N$^+R_aR_bR_c$, —C(O)O$(C_1-C_4)$alkylene-NR$_d$R$_e$, —O—C(O)—$(C_1-C_4)$alkylene-NR$_d$R$_e$, —O—C(O)—$(C_1-C_4)$alkylene-N$^+R_aR_bR_c$, n is 2, m is 2, $R_7$ is —H, $R_a$, $R_b$ and $R_c$ are independently —$(C_1-C_4)$alkyl, $R_d$ and $R_e$ are independently —$(C_1-C_4)$alkyl.

In another embodiment X is

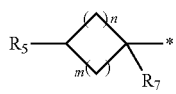

$R_5$ is -heteroaryl-$(CH_2)_t$—N$^+R_aR_bR_c$, n is 1 or 2, m is 1 or 2, $R_7$ is —H, $R_a$, $R_b$ and $R_c$ are independently —$(C_1-C_4)$alkyl, $R_d$ and $R_e$ are independently —$(C_1-C_4)$alkyl.

In another embodiment X is

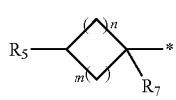

$R_5$ is

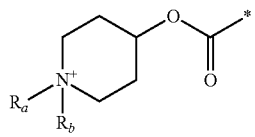

n is 2, m is 2, $R_7$ is —H, $R_a$ and $R_b$ are independently —$(C_1-C_4)$alkyl.

In another embodiment X is

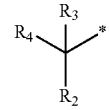

$R_2$ and $R_3$ are independently —H or linear or branched —$(C_1-C_4)$alkyl or $R_2$ and $R_3$ may form together a —$(C_3-C_6)$cycloalkyl; $R_4$ is

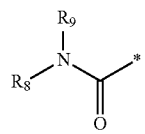

$R_8$ is —H or —$(C_1-C_4)$alkyl; $R_9$ is selected from a group consisting of -heterocycloalkyl, heterocycloalkyl-$(C_1-C_4)$alkylene-, $(C_1-C_4)$alkylene-NR$_d$R$_e$ and $(C_1-C_4)$alkylene-N$^+R_aR_bR_c$, wherein said -heterocycloalkyl or heterocycloalkyl-$(C_1-C_4)$alkylene- may be optionally substituted by one or more —$(C_1-C_4)$alkyl and —the nitrogen atom in the heterocycloalkyl or heterocycloalkyl-$(C_1-C_4)$alkylene- may be quaternized; $R_a$ is —$(C_1-C_4)$alkyl; $R_b$ is —$(C_1-C_4)$alkyl; $R_c$ is selected from a group consisting of —$(C_1-C_4)$alkyl, aryl-$(C_1-C_4)$alkylene- and heteroaryl-$(C_1-C_4)$alkylene-, wherein said heteroaryl-$(C_1-C_4)$alkylene may be optionally substituted by one or more —$(C_1-C_4)$alkyl groups; $R_d$ and $R_e$ are independently —H or —$(C_1-C_4)$alkyl.

In another embodiment X is

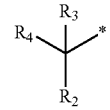

$R_2$ is —H or linear or branched —$(C_1-C_4)$alkyl; $R_3$ is —H; $R_4$ is

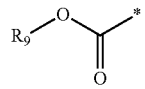

$R_9$ is heterocycloalkyl-$(C_1-C_4)$alkylene- optionally substituted by one or more —$(C_1-C_4)$alkyl and wherein the nitrogen atom in the heterocycloalkyl-$(C_1-C_4)$alkylene- may be quaternized.

In another embodiment, a compound of the invention is selected in the group consisting of

| Ex. | Chemical name |
|---|---|
| 1 | 2'-(4-Cyano-phenyl)-2-methyl-5-oxo-1-(3-trifluoromethyl-phenyl)-2,5-dihydro-1H,2'H-[3,3']bipyrazolyl-4-carboxylic acid ethyl ester |
| 2 | 2'-(4-Cyano-phenyl)-2-methyl-5-oxo-1-(3-trifluoromethyl-phenyl)-2,5-dihydro-1H,2'H-[3,3']bipyrazolyl-4-carboxylic acid (1-methyl-piperidin-4-yl)-amide |
| 3 | 2'-(4-Cyano-phenyl)-2-methyl-5-oxo-1-(3-trifluoromethyl-phenyl)-2,5-dihydro-1H,2'H-[3,3']bipyrazolyl-4-carboxylic acid ethylamide |
| 4 | (3aS,5R,6aR)-5-{[2'-(4-Cyano-phenyl)-2-methyl-5-oxo-1-(3-trifluoromethyl-phenyl)-2,5-dihydro-1H,2'H-[3,3']bipyrazolyl-4-carbonyl]-amino}-hexahydro-cyclopenta[c]pyrrole-2-carboxylic acid tert-butyl ester |
| 5 | 2'-(4-Cyano-phenyl)-2-methyl-5-oxo-1-(3-trifluoromethyl-phenyl)-2,5-dihydro-1H,2'H-[3,3']bipyrazolyl-4-carboxylic acid [(S)-1-(5-dimethylaminomethyl-oxazol-2-yl)-ethyl]-amide |
| 6 | 2'-(4-Cyano-phenyl)-2-methyl-5-oxo-1-(3-trifluoromethyl-phenyl)-2,5-dihydro-1H,2'H-[3,3']bipyrazolyl-4-carboxylic acid [1-(2-dimethylamino-acetyl)-piperidin-4-yl]-amide |
| 7 | 2'-(4-Cyano-phenyl)-2-methyl-5-oxo-1-(3-trifluoromethyl-phenyl)-2,5-dihydro-1H,2'H-[3,3']bipyrazolyl-4-carboxylic acid {(S)-1-[methyl-(1-methyl-piperidin-4-ylmethyl)-carbamoyl]-ethyl}-amide |
| 8 | 2'-(4-Cyano-phenyl)-2-methyl-5-oxo-1-(3-trifluoromethyl-phenyl)-2,5-dihydro-1H,2'H-[3,3']bipyrazolyl-4-carboxylic acid [(S)-1-(5-dimethylaminomethyl-[1,3,4]oxadiazol-2-yl)-ethyl]-amide |
| 9 | 2'-(4-Cyano-phenyl)-2-methyl-5-oxo-1-(3-trifluoromethyl-phenyl)-2,5-dihydro-1H,2'H-[3,3']bipyrazolyl-4-carboxylic acid {1-methyl-1-[methyl-(1-methyl-piperidin-4-ylmethyl)-carbamoyl]-ethyl}-amide |
| 10 | 2'-(4-Cyano-phenyl)-2-methyl-5-oxo-1-(3-trifluoromethyl-phenyl)-2,5-dihydro-1H,2'H-[3,3']bipyrazolyl-4-carboxylic acid [1-(5-dimethylaminomethyl-oxazol-2-yl)-1-methyl-ethyl]-amide |
| 11 | 2'-(4-Cyano-phenyl)-2-methyl-5-oxo-1-(3-trifluoromethyl-phenyl)-2,5-dihydro-1H,2'H-[3,3']bipyrazolyl-4-carboxylic acid [(S)-1-(5-dimethylaminomethyl-oxazol-2-yl)-2-methyl-propyl]-amide |
| 12 | 2'-(Trans-4-cyano-phenyl)-2-methyl-5-oxo-1-(3-trifluoromethyl-phenyl)-2,5-dihydro-1H,2'H-[3,3']bipyrazolyl-4-carboxylic acid [4-(1-methyl-piperidin-4-ylcarbamoyl)-cyclohexyl]-amide |
| 13 | Trans-4-{[2'-(4-cyano-phenyl)-2-methyl-5-oxo-1-(3-trifluoromethyl-phenyl)-2,5-dihydro-1H,2'H-[3,3']bipyrazolyl-4-carbonyl]-amino}-cyclohexanecarboxylic acid 1-methyl-piperidin-4-yl ester |
| 14 | 2'-(Trans-4-cyano-phenyl)-2-methyl-5-oxo-1-(3-trifluoromethyl-phenyl)-2,5-dihydro-1H,2'H-[3,3']bipyrazolyl-4-carboxylic acid [4-(4-dimethylamino-piperidine-1-carbonyl)-cyclohexyl]-amide |
| 15 | Trans-4-{[2'-(4-cyano-phenyl)-2-methyl-5-oxo-1-(3-trifluoromethyl-phenyl)-2,5-dihydro-1H,2'H-[3,3']bipyrazolyl-4-carbonyl]-amino}-cyclohexanecarboxylic acid 2-dimethylamino-ethyl ester |
| 16 | Dimethylamino-acetic acid trans-4-{[2'-(4-cyano-phenyl)-2-methyl-5-oxo-1-(3-trifluoromethyl-phenyl)-2,5-dihydro-1H,2'H-[3,3']bipyrazolyl-4-carbonyl]-amino}-cyclohexyl ester |
| 17 | 2'-(4-Cyano-phenyl)-2-methyl-5-oxo-1-(3-trifluoromethyl-phenyl)-2,5-dihydro-1H,2'H-[3,3']bipyrazolyl-4-carboxylic acid [(S)-1-methyl-2-(4-methyl-[1,4]diazepan-1-yl)-2-oxo-ethyl]-amide |
| 18 | 4-{[2'-(4-Cyano-phenyl)-2-methyl-5-oxo-1-(3-trifluoromethyl-phenyl)-2,5-dihydro-1H,2'H-[3,3']bipyrazolyl-4-carbonyl]-amino}-1,1-dimethyl-piperidinium benzene sulphonate |
| 19 | 4-((S)-1-{[2'-(4-Cyano-phenyl)-2-methyl-5-oxo-1-(3-trifluoromethyl-phenyl)-2,5-dihydro-1H,2'H-[3,3']bipyrazolyl-4-carbonyl]-amino}-ethyl)-1-methyl-pyridinium benzene sulphonate |
| 20 | (3-{[2'-(4-Cyano-phenyl)-2-methyl-5-oxo-1-(3-trifluoromethyl-phenyl)-2,5-dihydro-1H,2'H-[3,3']bipyrazolyl-4-carbonyl]-amino}-propyl)-trimethyl-ammonium benzene sulphonate |
| 21 | (2-{[2'-(4-Cyano-phenyl)-2-methyl-5-oxo-1-(3-trifluoromethyl-phenyl)-2,5-dihydro-1H,2'H-[3,3']bipyrazolyl-4-carbonyl]-amino}-ethyl)-trimethyl-ammonium benzene sulphonate |
| 22 | 8-{[2'-(4-Cyano-phenyl)-2-methyl-5-oxo-1-(3-trifluoromethyl-phenyl)-2,5-dihydro-1H,2'H-[3,3']bipyrazolyl-4-carbonyl]-amino}-5-azonia-spiro[4.5]decane bromide |
| 23 | (3aS,5R,6aR)-5-{[2'-(4-Cyano-phenyl)-2-methyl-5-oxo-1-(3-trifluoromethyl-phenyl)-2,5-dihydro-1H,2'H-[3,3']bipyrazolyl-4-carbonyl]-amino}-2,2-dimethyl-octahydro-cyclopenta[c]pyrrolium benzene sulphonate |
| 24 | (Trans-4-{[2'-(4-cyano-phenyl)-2-methyl-5-oxo-1-(3-trifluoromethyl-phenyl)-2,5-dihydro-1H,2'H-[3,3']bipyrazolyl-4-carbonyl]-amino}-cyclohexylmethyl)-trimethyl-ammonium benzene sulphonate |
| 25 | Benzyl-(trans-4-{[2'-(4-cyano-phenyl)-2-methyl-5-oxo-1-(3-trifluoromethyl-phenyl)-2,5-dihydro-1H,2'H-[3,3']bipyrazolyl-4-carbonyl]-amino}-cyclohexylmethyl)-dimethyl-ammonium bromide |
| 26 | 4-((S)-2-{[2'-(4-Cyano-phenyl)-2-methyl-5-oxo-1-(3-trifluoromethyl-phenyl)-2,5-dihydro-1H,2'H-[3,3']bipyrazolyl-4-carbonyl]-amino}-propionyl)-1,1-dimethyl-piperazin-1-ium benzene sulphonate |
| 27 | 1-Benzyl-4-((S)-2-{[2'-(4-cyano-phenyl)-2-methyl-5-oxo-1-(3-trifluoromethyl-phenyl)-2,5-dihydro-1H,2'H-[3,3']bipyrazolyl-4-carbonyl]-amino}-propionyl)-1-methyl-piperazin-1-ium bromide |

-continued

| Ex. | Chemical name |
|---|---|
| 28 | (1S,3S,5R)-3-{[2'-(4-Cyano-phenyl)-2-methyl-5-oxo-1-(3-trifluoromethyl-phenyl)-2,5-dihydro-1H,2'H-[3,3']bipyrazolyl-4-carbonyl]-amino}-8,8-dimethyl-8-azonia-bicyclo[3.2.1]octane benzene sulphonate |
| 29 | [Trans-4-({[2'-(4-cyano-phenyl)-2-methyl-5-oxo-1-(3-trifluoromethyl-phenyl)-2,5-dihydro-1H,2'H-[3,3']bipyrazolyl-4-carbonyl]-amino}-methyl)-cyclohexyl]-trimethyl-ammonium benzene sulphonate |
| 30 | [2-((S)-1-{[2'-(4-Cyano-phenyl)-2-methyl-5-oxo-1-(3-trifluoromethyl-phenyl)-2,5-dihydro-1H,2'H-[3,3']bipyrazolyl-4-carbonyl]-amino}-ethyl)-oxazol-5-ylmethyl]-trimethyl-ammonium benzene sulphonate |
| 31 | Benzyl-[2-((S)-1-{[2'-(4-cyano-phenyl)-2-methyl-5-oxo-1-(3-trifluoromethyl-phenyl)-2,5-dihydro-1H,2'H-[3,3']bipyrazolyl-4-carbonyl]-amino}-ethyl)-oxazol-5-ylmethyl]-dimethyl-ammonium bromide |
| 32 | [2-((S)-1-{[2'-(4-Cyano-phenyl)-2-methyl-5-oxo-1-(3-trifluoromethyl-phenyl)-2,5-dihydro-1H,2'H-[3,3']bipyrazolyl-4-carbonyl]-amino}-ethyl)-oxazol-5-ylmethyl]-dimethyl-(5-methyl-isoxazol-3-ylmethyl)-ammonium chloride |
| 33 | [2-(4-{[2'-(4-Cyano-phenyl)-2-methyl-5-oxo-1-(3-trifluoromethyl-phenyl)-2,5-dihydro-1H,2'H-[3,3']bipyrazolyl-4-carbonyl]-amino}-piperidin-1-yl)-2-oxo-ethyl]-trimethyl-ammonium benzene sulphonate |
| 34 | (2-{4-[2'-(4-Cyano-phenyl)-2-methyl-5-oxo-1-(3-trifluoromethyl-phenyl)-2,5-dihydro-1H,2'H-[3,3']bipyrazolyl-4-carbonyloxy]-piperidin-1-yl}-2-oxo-ethyl)-trimethyl-ammonium benzene sulphonate |
| 35 | Benzyl-[1-((S)-2-{[2'-(4-cyano-phenyl)-2-methyl-5-oxo-1-(3-trifluoromethyl-phenyl)-2,5-dihydro-1H,2'H-[3,3']bipyrazolyl-4-carbonyl]-amino}-propionyl)-piperidin-4-yl]-dimethyl-ammonium bromide |
| 36 | 4-{[((S)-2-{[2'-(4-Cyano-phenyl)-2-methyl-5-oxo-1-(3-trifluoromethyl-phenyl)-2,5-dihydro-1H,2'H-[3,3']bipyrazolyl-4-carbonyl]-amino}-propionyl)-methyl-amino]-methyl}-1,1-dimethyl-piperidinium benzene sulphonate |
| 37 | [5-((S)-1-{[2'-(4-Cyano-phenyl)-2-methyl-5-oxo-1-(3-trifluoromethyl-phenyl)-2,5-dihydro-1H,2'H-[3,3']bipyrazolyl-4-carbonyl]-amino}-ethyl)-[1,3,4]oxadiazol-2-ylmethyl]-trimethyl-ammonium benzene sulphonate |
| 38 | 4-((S)-2-{[2'-(4-Cyano-phenyl)-2-methyl-5-oxo-1-(3-trifluoromethyl-phenyl)-2,5-dihydro-1H,2'H-[3,3']bipyrazolyl-4-carbonyl]-amino}-propionyloxymethyl)-1,1-dimethyl-piperidinium benzene sulphonate |
| 39 | 4-(4-{[2'-(4-Cyano-phenyl)-2-methyl-5-oxo-1-(3-trifluoromethyl-phenyl)-2,5-dihydro-1H,2'H-[3,3']bipyrazolyl-4-carbonyl]-amino}-piperidine-1-carbonyl)-1,1-dimethyl-piperidinium benzene sulphonate |
| 40 | 4-{[(2-{[2'-(4-Cyano-phenyl)-2-methyl-5-oxo-1-(3-trifluoromethyl-phenyl)-2,5-dihydro-1H,2'H-[3,3']bipyrazolyl-4-carbonyl]-amino}-2-methyl-propionyl)-methyl-amino]-methyl}-1,1-dimethyl-piperidinium benzene sulphonate |
| 41 | [1-((S)-2-{[2'-(4-Cyano-phenyl)-2-methyl-5-oxo-1-(3-trifluoromethyl-phenyl)-2,5-dihydro-1H,2'H-[3,3']bipyrazolyl-4-carbonyl]-amino}-propionyl)-piperidin-4-yl]-trimethyl-ammonium benzene sulphonate |
| 42 | {2-[(Trans-4-{[2'-(4-cyano-phenyl)-2-methyl-5-oxo-1-(3-trifluoromethyl-phenyl)-2,5-dihydro-1H,2'H-[3,3']bipyrazolyl-4-carbonyl]-amino}-cyclohexanecarbonyl)-amino]-ethyl}-trimethyl-ammonium benzene sulphonate |
| 43 | Benzyl-[2-(4-{[2'-(4-cyano-phenyl)-2-methyl-5-oxo-1-(3-trifluoromethyl-phenyl)-2,5-dihydro-1H,2'H-[3,3']bipyrazolyl-4-carbonyl]-amino}-piperidin-1-yl)-2-oxo-ethyl]-dimethyl-ammonium bromide |
| 44 | {2-[((S)-2-{[2'-(4-Cyano-phenyl)-2-methyl-5-oxo-1-(3-trifluoromethyl-phenyl)-2,5-dihydro-1H,2'H-[3,3']bipyrazolyl-4-carbonyl]-amino}-propionyl)-methyl-amino]-ethyl}-trimethyl-ammonium benzene sulphonate |
| 45 | [(Trans-4-{[2'-(4-cyano-phenyl)-2-methyl-5-oxo-1-(3-trifluoromethyl-phenyl)-2,5-dihydro-1H,2'H-[3,3']bipyrazolyl-4-carbonyl]-amino}-cyclohexylcarbamoyl)-methyl]-trimethyl-ammonium benzene sulphonate |
| 46 | (Trans-4-{[2'-(4-cyano-phenyl)-2-methyl-5-oxo-1-(3-trifluoromethyl-phenyl)-2,5-dihydro-1H,2'H-[3,3']bipyrazolyl-4-carbonyl]-amino}-cyclohexylmethyl)-(2,5-dimethyl-2H-pyrazol-3-ylmethyl)-dimethyl-ammonium bromide |
| 47 | (Trans-4-{[2'-(4-cyano-phenyl)-2-methyl-5-oxo-1-(3-trifluoromethyl-phenyl)-2,5-dihydro-1H,2'H-[3,3']bipyrazolyl-4-carbonyl]-amino}-cyclohexylmethyl)-dimethyl-(5-methyl-isoxazol-3-ylmethyl)-ammonium chloride |
| 48 | [2-(1-{[2'-(4-Cyano-phenyl)-2-methyl-5-oxo-1-(3-trifluoromethyl-phenyl)-2,5-dihydro-1H,2'H-[3,3']bipyrazolyl-4-carbonyl]-amino}-1-methyl-ethyl)-oxazol-5-ylmethyl]-trimethyl-ammonium benzene sulphonate |
| 49 | 4-((S)-2-{[2'-(4-Cyano-phenyl)-2-methyl-5-oxo-1-(3-trifluoromethyl-phenyl)-2,5-dihydro-1H,2'H-[3,3']bipyrazolyl-4-carbonyl]-amino}-propionyl)-1-methyl-1-(5-methyl-isoxazol-3-ylmethyl)-piperazin-1-ium chloride |
| 50 | [2-(4-{[2'-(4-Cyano-phenyl)-2-methyl-5-oxo-1-(3-trifluoromethyl-phenyl)-2,5-dihydro-1H,2'H-[3,3']bipyrazolyl-4-carbonyl]-amino}-piperidin-1-yl)-2-oxo-ethyl]-dimethyl-(5-methyl-isoxazol-3-ylmethyl)-ammonium chloride |
| 51 | {2-[(Trans-3-{[2'-(4-cyano-phenyl)-2-methyl-5-oxo-1-(3-trifluoromethyl-phenyl)-2,5-dihydro-1H,2'H-[3,3']bipyrazolyl-4-carbonyl]-amino}-cyclobutanecarbonyl)-amino]-ethyl}-trimethyl-ammonium benzene sulphonate |
| 52 | {2-[2-((S)-1-{[2'-(4-Cyano-phenyl)-2-methyl-5-oxo-1-(3-trifluoromethyl-phenyl)-2,5-dihydro-1H,2'H-[3,3']bipyrazolyl-4-carbonyl]-amino}-ethyl)-oxazol-5-yl]-ethyl}-trimethyl-ammonium benzene sulphonate |

| Ex. | Chemical name |
|---|---|
| 53 | [2-((S)-1-{[2'-(4-Cyano-phenyl)-2-methyl-5-oxo-1-(3-trifluoromethyl-phenyl)-2,5-dihydro-1H,2'H-[3,3']bipyrazolyl-4-carbonyl]-amino}-2-methyl-propyl)-oxazol-5-ylmethyl]-trimethyl-ammonium benzene sulphonate |
| 54 | {[(Trans-4-{[2'-(4-cyano-phenyl)-2-methyl-5-oxo-1-(3-trifluoromethyl-phenyl)-2,5-dihydro-1H,2'H-[3,3']bipyrazolyl-4-carbonyl]-amino}-cyclohexylmethyl)-carbamoyl]-methyl}-trimethyl-ammonium benzene sulphonate |
| 55 | 4-[(Trans-3-{[2'-(4-cyano-phenyl)-2-methyl-5-oxo-1-(3-trifluoromethyl-phenyl)-2,5-dihydro-1H,2'H-[3,3']bipyrazolyl-4-carbonyl]-amino}-cyclobutanecarbonyl)-amino]-1,1-dimethyl-piperidinium benzene sulphonate |
| 56 | 4-[((S)-2-{[2'-(4-Cyano-phenyl)-2-methyl-5-oxo-1-(3-trifluoromethyl-phenyl)-2,5-dihydro-1H,2'H-[3,3']bipyrazolyl-4-carbonyl]-amino}-propionyl)-methyl-amino]-1,1-dimethyl-piperidinium benzene sulphonate |
| 57 | {2-[(1-{[2'-(4-Cyano-phenyl)-2-methyl-5-oxo-1-(3-trifluoromethyl-phenyl)-2,5-dihydro-1H,2'H-[3,3']bipyrazolyl-4-carbonyl]-amino}-cyclopentanecarbonyl)-amino]-ethyl}-trimethyl-ammonium benzene sulphonate |
| 58 | 4-[(4-{[2'-(4-Cyano-phenyl)-2-methyl-5-oxo-1-(3-trifluoromethyl-phenyl)-2,5-dihydro-1H,2'H-[3,3']bipyrazolyl-4-carbonyl]-amino}-cyclohexanecarbonyl)-amino]-1,1-dimethyl-piperidinium benzene sulphonate |
| 59 | 4-(Trans-4-{[2'-(4-cyano-phenyl)-2-methyl-5-oxo-1-(3-trifluoromethyl-phenyl)-2,5-dihydro-1H,2'H-[3,3']bipyrazolyl-4-carbonyl]-amino}-cyclohexanecarbonyloxy)-1,1-dimethyl-piperidinium benzene sulphonate |
| 60 | [1-(4-{[2'-(4-Cyano-phenyl)-2-methyl-5-oxo-1-(3-trifluoromethyl-phenyl)-2,5-dihydro-1H,2'H-[3,3']bipyrazolyl-4-carbonyl]-amino}-cyclohexanecarbonyl)-piperidin-4-yl]-trimethyl-ammonium benzene sulphonate |
| 61 | {2-[(1-{[2'-(4-Cyano-phenyl)-2-methyl-5-oxo-1-(3-trifluoromethyl-phenyl)-2,5-dihydro-1H,2'H-[3,3']bipyrazolyl-4-carbonyl]-amino}-cyclopentanecarbonyl)-methyl-amino]-ethyl}-trimethyl-ammonium benzene sulphonate |
| 62 | (Trans-4-{[2'-(4-cyano-phenyl)-2-methyl-5-oxo-1-(3-trifluoromethyl-phenyl)-2,5-dihydro-1H,2'H-[3,3']bipyrazolyl-4-carbonyl]-amino}-cyclohexyloxycarbonylmethyl)-trimethyl-ammonium benzene sulphonate |
| 63 | 3-(4-{[2'-(4-Cyano-phenyl)-2-methyl-5-oxo-1-(3-trifluoromethyl-phenyl)-2,5-dihydro-1H,2'H-[3,3']bipyrazolyl-4-carbonyl]-amino}-piperidin-1-yl)-3-oxo-propyl)-trimethyl-ammonium benzene sulphonate |
| 64 | [2-(4-{[2'-(4-Cyano-phenyl)-2-methyl-5-oxo-1-(3-trifluoromethyl-phenyl)-2,5-dihydro-1H,2'H-[3,3']bipyrazolyl-4-carbonyl]-amino}-4-methyl-piperidin-1-yl)-2-oxo-ethyl]-trimethyl-ammonium benzene sulphonate |
| 65 | [2-(Trans-4-{[2'-(4-cyano-phenyl)-2-methyl-5-oxo-1-(3-trifluoromethyl-phenyl)-2,5-dihydro-1H,2'H-[3,3']bipyrazolyl-4-carbonyl]-amino}-cyclohexanecarbonyloxy)-ethyl]-trimethyl-ammonium benzene sulphonate |
| 66 | 4-((S)-2-{[2'-(4-Cyano-phenyl)-2-methyl-5-oxo-1-(3-trifluoromethyl-phenyl)-2,5-dihydro-1H,2'H-[3,3']bipyrazolyl-4-carbonyl]-amino}-propionyl)-1,1-dimethyl-[1,4]diazepan-1-ium benzene sulphonate |
| 67 | [2-(Trans-4-{[2'-(4-Cyano-phenyl)-2-methyl-5-oxo-1-(3-trifluoromethyl-phenyl)-2,5-dihydro-1H,2'H-[3,3']bipyrazolyl-4-carbonyl]-amino}-cyclohexyl)-oxazol-5-ylmethyl]-trimethyl-ammonium benzene sulphonate |
| 68 | [2-(Trans-3-{[2'-(4-cyano-phenyl)-2-methyl-5-oxo-1-(3-trifluoromethyl-phenyl)-2,5-dihydro-1H,2'H-[3,3']bipyrazolyl-4-carbonyl]-amino}-cyclobutyl)-oxazol-5-ylmethyl]-trimethyl-ammonium benzene sulphonate |
| 69 | 1-(4-{[2'-(4-Cyano-phenyl)-2-methyl-5-oxo-1-(3-trifluoromethyl-phenyl)-2,5-dihydro-1H,2'H-[3,3']bipyrazolyl-4-carbonyl]-amino}-cyclohexylmethyl)-pyridinium bromide |
| 70 | 1-(4-{[2'-(4-Cyano-phenyl)-2-methyl-5-oxo-1-(3-trifluoromethyl-phenyl)-2,5-dihydro-1H,2'H-[3,3']bipyrazolyl-4-carbonyl]-amino}-cyclohexylmethyl)-3-methyl-3H-imidazol-1-ium bromide |
| 71 | 2'-(4-Cyano-phenyl)-2-ethyl-5-oxo-1-(3-trifluoromethyl-phenyl)-2,5-dihydro-1H,2'H-[3,3']bipyrazolyl-4-carboxylic acid ethyl ester |
| 72 | 5-[1-(4-Cyano-phenyl)-1H-imidazol-2-yl]-1-methyl-3-oxo-2-(3-trifluoromethyl-phenyl)-2,3-dihydro-1H-pyrazole-4-carboxylic acid cyclopentyl-amide |

The therapeutic utility of the present compounds is pertinent to any disease that is known to be at least partially mediated by the action of human neutrophil elastase. For example, the present compounds can be beneficial in the treatment of chronic obstructive pulmonary disease (COPD), cystic fibrosis (CF), bronchiectasis, acute respiratory distress syndrome (ARDS), pulmonary emphysema, pneumonia and lung fibrosis.

Compounds of the present invention are useful for treatment of inflammatory respiratory disorders, for example asthma (mild, moderate or severe), steroid resistant asthma, bronchitis, chronic obstructive pulmonary disease (COPD), cystic fibrosis (CF), pulmonary edema, pulmonary embolism, pneumonia, pulmonary sarcoidosis, pulmonary emphysema, silicosis, pulmonary fibrosis, pulmonary hypertension, respiratory failure, acute respiratory distress syndrome (ARDS), emphysema, chronic bronchitis, tuberculosis, aspergillosis and other fungal infections, hypersensitivity pneumonitis, vasculitic and thrombotic disorders of the lung vasculature, antiitussive activity including treatment of chronic cough associated with inflammatory and secretory conditions of the airways, infection due to respiratory syncytial virus, influenza, coronavirus (including severe acute respiratory syndrome, SARS) and adenovirus, bronchiectasis and lung cancer.

The present invention is also concerned with pharmaceutical formulations comprising, as an active ingredient, a compound of the invention. Other compounds can be combined with compounds of the present invention for the prevention and treatment of inflammatory diseases of the lung. Thus the invention is also concerned with pharmaceutical compositions for preventing and treating inflammatory diseases of the lung comprising a therapeutically effective amount of a compound of the invention and one or more other therapeutic agents.

Suitable therapeutic agents for a combination therapy with compounds of the invention include: (1) a corticosteroid, for example budesonide, beclomethasone, beclomethasone (e.g., as the mono or the dipropionate ester), flunisolide, fluticasone (e.g. as the propionate or furoate ester), Ciclesonide, mometasone (e.g. as the furoate ester), mometasone desonide, rofleponide, hydrocortisone, prednisone, prednisolone, methyl prednisolone, naflocort, deflazacort, halopredone acetate, fluocinolone acetonide, fluocinonide, clocortolone, tipredane, prednicarbate, alclometasone dipropionate, halometasone, rimexolone, deprodone propionate, triamcinolone, betamethasone, fludrocortisone, desoxycorticosterone, rofleponide, etiprednol dicloacetate and the like. Steroid drugs can additionally include steroids in clinical or pre-clinical development for respiratory diseases such as GW-685698, GW-799943, GSK 870086, QAE397, NCX-1010, NCX-1020, NO-dexamethasone, PL-2146, NS-126 (formerly ST-126). Steroid drugs can also additionally include next generation molecules in development with reduced side effect profiles such as selective glucocorticoid receptor agonists (SEGRAs), including ZK-216348 and AZD5423; (2) a β2-adrenoreceptor agonist, such as albuterol, bambuterol, terbutaline, fenoterol, formoterol, formoterol fumarate, salmeterol, salmeterol xinafoate, arformoterol, arfomoterol tartrate, indacaterol (QAB-149), carmoterol, BI 1744 CL, GSK159797 (milveterol), GSK59790, GSK159802, GSK642444 (vilanterol), GSK678007, GSK96108, clenbuterol, procaterol, bitolterol, LAS100977 (abediterol), BI1744CL (olodaterol) and brodxaterol; (3) a leukotriene modulator, for example montelukast, zafirlukast or pranlukast; (4) anticholinergic agents, for example selective muscarinic-3 (M3) receptor antagonists such as ipratropium bromide, tiotropium, tiotropium bromide (Spiriva®), glycopyrronium bromide, aclidinium bromide, LAS34273, GSK656398, GSK233705, GSK 573719 (umeclidinium), LAS35201, QAT370 and oxytropium bromide; (5) phosphodiesterase-IV (PDE-IV) inhibitors, for example roflumilast, cilomilast or theophylline; (6) an antitussive agent, such as codeine or dextramorphan; and (7) a non-steroidal anti-inflammatory agent (NSAID), for example ibuprofen or ketoprofen; (8) a mucolytic, for example N acetyl cysteine or fudostein; (9) an expectorant/mucokinetic modulator, for example ambroxol, hypertonic solutions (e.g. saline or mannitol) or surfactant; (10) a peptide mucolytic, for example recombinant human deoxyribonuclease I (dornase-alfa and rhDNase) or helicidin; (11) antibiotics, for example azithromycin, tobramycin and aztreonam; (12) p38 Mitogen Activated Protein (MAP) kinase inhibitors, such as GSK 856553 and GSK 681323; (13) inhibitors of Janus Kinases (JAK) such as CP-690550 or GLPG0634; (14) Spleen Tyrosine Kinase (SYK) inhibitors such as R406, R343 or PRT062607; (15) inhibitors of delta and/or gamma isoforms of Phosphatidylinositol 3-kinase (PI3K).; (16) anti-retroviral agents such as ribavirin, zanamivir or laninamivir; and (17) PPAR-γ agonists such as pioglitazone and rosiglitazone.

In one aspect, the present invention concerns the use of inhaled administration of compounds of the invention in combination with other anti-inflammatory drugs and bronchodilator drug combinations (i.e. triple combination product), including but not limited to salmeterol xinafoate/fluticasone propionate (Advair/Seretide®), vilanterol/fluticasone furoate (BREO ELLIPTA™), formoterol fumarate/budesonide (Symbicort®), formoterol fumarate/mometasone furoate, formoterol fumarate/beclometasone dipropionate (Foster®), formoterol fumarate/fluticasone propionate (FlutiForm®), Indacaterol/mometasone furoate, Indacaterol/QAE-397, GSK159797/GSK 685698, GSK159802/GSK 685698, GSK642444/GSK 685698, formoterol fumarate/ciclesonide, arformoterol tartrate/ciclesonide.

In another aspect, the present invention concerns the use of inhaled administration of compounds of the invention in combination with other bronchodilator drug combinations, particularly β$_2$ agonist/M$_3$ antagonist combinations (i.e. triple combination product), including but not limited to salmeterol xinafoate/tiotropium bromide, formoterol fumarate/tiotropium bromide, formoterol fumarate/glycopyrrolate (PT003), BI 1744 CL/tiotropium bromide, indacaterol/NVA237, indacterol/QAT-370, formoterol/LAS34273, umeclidinium/vilanterol (Anoro™), GSK159797/GSK 573719, GSK159802/GSK 573719, GSK642444/GSK 573719, GSK159797/GSK 233705, GSK159802/GSK 233705, GSK642444/GSK 233705.

The weight ratio of the first and second active ingredients can be varied and will depend upon the effective dose of each ingredient. Generally, an effective dose of each will be used.

The magnitude of prophylactic or therapeutic dose of a compound of the present invention will, of course, vary with the nature of the severity of the condition to be treated and with the particular compound and its route of administration, and will generally be determined by clinical trial as required in the pharmaceutical art. It will also vary according to the age, weight and response of the individual patient. In general, the daily dose range will lie within the range of from about 0.001 mg to about 100 mg per kg body weight of a mammal, preferably 0.01 mg to about 50 mg per kg, and most preferably 0.1 to 10 mg per kg, in single or divided doses. On the other hand, it can be necessary to use dosages outside these limits in some cases.

Another aspect of the present invention concerns pharmaceutical compositions which comprise a compound of the invention and a pharmaceutically acceptable carrier. The pharmaceutical compositions of the present invention comprise a compound of the present invention as an active ingredient or a pharmaceutically acceptable salt thereof, and can also contain a pharmaceutically acceptable carrier and optionally other therapeutic ingredients.

Any suitable route of administration can be employed for providing a mammal, especially a human, with an effective dosage of a compound of the invention. In therapeutic use, the active compound can be administered by any convenient, suitable or effective route. Suitable routes of administration are known, and include oral, intravenous, rectal, parenteral, topical, ocular, nasal, buccal and pulmonary (by inhalation).

Compositions suitable for administration by inhalation are known, and can include carriers and/or diluents that are known for use in such compositions. The composition can contain 0.01-99% by weight of active compound. Preferably, a unit dose comprises the active compound in an amount of 1 µg to 10 mg.

The most suitable dosage level can be determined by any known suitable method. It will be understood, however, that the specific amount for any particular patient will depend upon a variety of factors, including the activity of the specific compound that is used, the age, body weight, diet, general health and sex of the patient, time of administration, the route of administration, the rate of excretion, the use of any other drugs, and the severity of the disease to be treated.

For delivery by inhalation, the active compound is preferably in the form of microparticles. They can be prepared by a variety of techniques, including spray-drying, freeze-drying and micronization.

By way of example, a composition of the invention can be prepared as a suspension for delivery from a nebulizer or as an aerosol in a liquid propellant, for example for use in a pressurised metered dose inhaler (PMDI). Propellants suitable for use in a PMDI are known and include CFC-12, HFA-134a, HFA-227, HCFC-22 (CCl2F2) and HFA-152 (CH4F2 and isobutane).

In a preferred embodiment, a composition is in dry powder form, for delivery using a dry powder inhaler (DPI). Many types of DPI are known.

Microparticles for delivery by administration can be formulated with excipients that aid delivery and release. For example, in a dry powder formulation, microparticles can be formulated with large carrier particles that aid flow from the DPI into the lung. Suitable carrier particles are known, and include lactose particles; they can have a mass median aerodynamic diameter of greater than 90 µm.

In the case of an aerosol-based formulation, a preferred composition is:

| | |
|---|---|
| Compound of the present invention | 24 mg/canister |
| Lecithin, NF Liq. Conc. | 1.2 mg/canister |
| Trichlorofluoromethane, NF | 4.025 g/canister |
| Dichlorodifluoromethane, NF | 12.15 g/canister. |

The compounds of the present invention can be used in combination with other drugs that are used in the treatment/prevention/suppression or amelioration of the diseases or conditions for which present compounds are useful. Such other drugs can be administered, by a route and in an amount commonly used therefore, contemporaneously or sequentially with a compound of the invention. When a compound of the invention is used contemporaneously with one or more other drugs, a pharmaceutical composition containing such other drugs in addition to the compound of the invention is preferred. Accordingly, the pharmaceutical compositions of the present invention include those that also contain one or more other active ingredients, in addition to a compound of the invention.

The agents of the present invention can be administered in inhaled form. Aerosol generation can be carried out using, for example, pressure-driven jet atomizers or ultrasonic atomizers, preferably using propellant-driven metered aerosols or propellant-free administration of micronized active compounds from, for example, inhalation capsules or other "dry powder" delivery systems.

The active compounds can be dosed as described depending on the inhaler system used. In addition to the active compounds, the administration forms can additionally contain excipients, such as, for example, propellants (e.g. Frigen in the case of metered aerosols), surface-active substances, emulsifiers, stabilizers, preservatives, flavorings, fillers (e.g. lactose in the case of powder inhalers) or, if appropriate, further active compounds.

For the purposes of inhalation, a large number of systems are available with which aerosols of optimum particle size can be generated and administered, using an inhalation technique which is appropriate for the patient. In addition to the use of adaptors (spacers, expanders) and pear-shaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®, Rotadisk®, Turbohaler® or the inhalers for example as described EP-A-0505321).

Procedure for the Preparation of Compounds of Formula (I)

The present invention further provides a process for the preparation of a compound of formula (I) or a pharmaceutically acceptable salt or quaternary salt thereof as defined above. Compounds of the invention (I) may be prepared according to routes illustrated below in Scheme A.

The skilled person may introduce, where appropriate, suitable variations to the conditions specifically described in the experimental in order to adapt the synthetic routes to the provision of further compounds of the invention. Such variations may include, but are not limited to, use of appropriate starting materials to generate different compounds, changes in the solvent and temperature of reactions, replacements of reagents with analogous chemical role, introduction or removal of protection/deprotection stages of functional groups sensitive to reaction conditions and reagents.

Also, introduction or removal of specific synthetic steps oriented to further functionalization of the chemical scaffold may be contemplated and is included within the scope of the present invention. Processes which can be used and are described and reported in the Examples and Schemes, should not be viewed as limiting the scope of the synthetic methods available for the preparation of the compounds of the invention.

Compounds used as starting materials or intermediates may be commercially available, their preparation may be specifically described in the literature, or they may be prepared according to known methods. In some instances, procedures for the preparation of intermediates or starting materials may be also provided in the experimental.

The process described is particularly advantageous as it is susceptible of being properly modulated, through any proper known variant, so as to obtain any of the desired compounds of the invention. Such variants are comprised within the scope of the present invention.

From all of the above, it should be clear that any of the described groups may be present as such or in any properly protected form.

In particular, functional groups present in the intermediate and compounds and which could generate unwanted side reaction and by-products, need to be properly protected before the alkylation, acylation, coupling or sulfonylation takes place. Likewise, subsequent deprotection of those same protected groups may follow upon completion of the said reactions.

In the present invention, unless otherwise indicated, the term "protecting group" designates a protective group adapted to preserve the function of the group it is bound to. Typically, protective groups are used to preserve amino, hydroxyl, or carboxyl functions. Appropriate protecting groups may thus include, for example, benzyl, benzyloxycarbonyl, t-butoxycarbonyl, alkyl or benzyl esters or the like, which are well known (see, for a general reference, T. W. Green; Protective Groups in Organic Synthesis (Wiley, N.Y. 1981), which is incorporated herein by reference in its entirety).

Likewise, selective protection and deprotection of any of the said groups, for instance including carbonyl, hydroxyl or amino groups, may be accomplished according to very well-known methods commonly employed in organic synthetic chemistry.

From all of the above, it should be clear that the above process, comprehensive of any variant thereof for the preparation of suitable compounds of the invention, may be conveniently modified so that to adapt the reaction conditions to the specific needs, for instance by choosing appropriate condensing agents, solvents and protective groups, as the case may be.

In the following Scheme, for compounds of formula (I) to (XI), unless otherwise indicated, groups A, W, X and Z have the same meanings as described for compounds of formula (I) above.

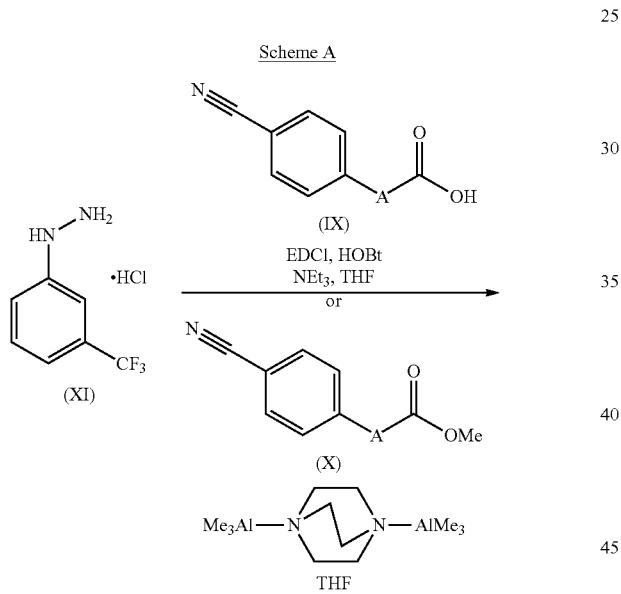

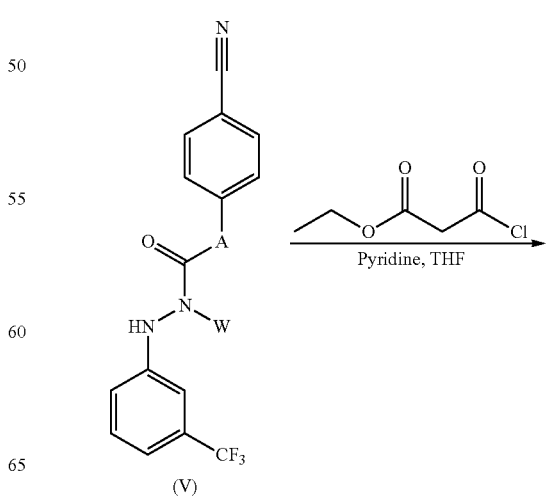

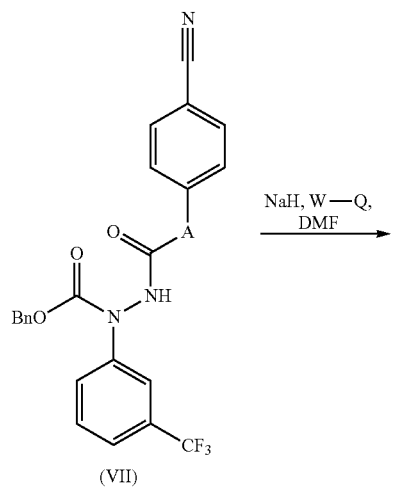

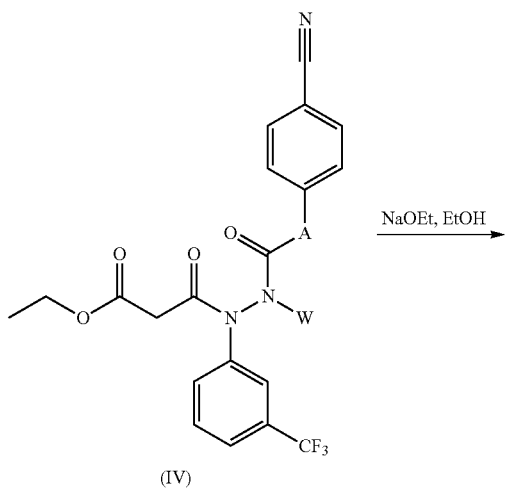

(IV)

↓ NaOEt, EtOH

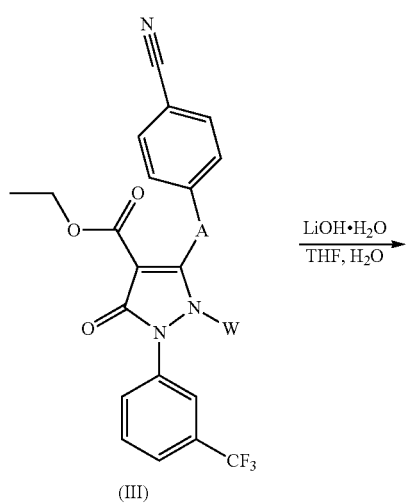

(III)

↓ LiOH·H₂O, THF, H₂O

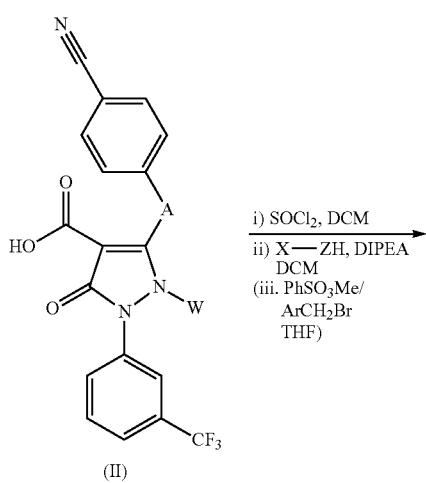

(II)

i) SOCl₂, DCM
ii) X—ZH, DIPEA DCM
(iii. PhSO₃Me/ ArCH₂Br THF)

→

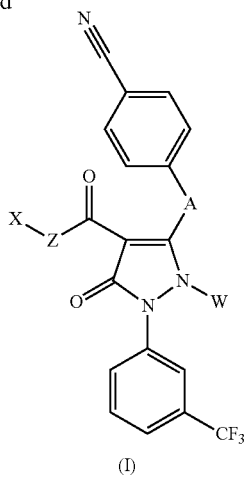

(I)

Compounds of formula (I) in Scheme A may be prepared from a compound of formula (II) by amide coupling with a compound of formula X-ZH. This may be done using an appropriate coupling reagent such as CDI in a suitable solvent such as THF at an appropriate temperature between 0° C. and the boiling point of the mixture. Alternatively a reagent such as thionyl chloride in a solvent such as DCM could be used to form an intermediate acid chloride which can then react with the compound of formula X-ZH in an appropriate solvent like DCM in the presence of a suitable base such as DIPEA at a temperature between 0° C. and the boiling point of the mixture.

In the instances where compounds of formula (I) contain a quaternary ammonium moiety then a quaternization step may also be used. This can be carried out by reaction with an alkylating agent such as methyl benzenesulphonate or benzyl bromide in a solvent such as THF at an appropriate temperature between ambient and the boiling point of the solvent.

Compounds of formula (II) may be synthesized from compounds of formula (III) by hydrolysis using suitable conditions such as lithium hydroxide in a mixture of water and THF at an appropriate temperature between 0° C. and the boiling point of the mixture.

Compounds of formula (III) may be prepared from compounds of formula (IV) by reaction with a suitable base such as sodium ethoxide in an appropriate solvent such as ethanol at a temperature between 0° C. and the boiling point of the mixture.

Compounds of formula (IV) may be prepared from compounds of formula (V) by reaction with ethyl malonyl chloride in the presence of a suitable base such as pyridine in a solvent such as THF at an appropriate temperature between 0° C. and the boiling point of the solvent.

Compounds of formula (V) may be synthesized from compounds of formula (VI) by deprotection using a technique such as hydrogenolysis for example with hydrogen gas in the presence of a catalyst such as palladium on activated carbon in a suitable solvent such as ethanol at an appropriate temperature between 0° C. and the boiling point of the solvent.

Compounds of formula (VI) may be synthesized from compounds of formula (VII) by reaction with a compound W-Q (wherein Q is a suitable leaving group, for example bromide, iodide or mesylate) in the presence of a base such as sodium hydride in an appropriate solvent such as DMF at a suitable temperature between 0° C. and the boiling point of the solvent.

Compounds of formula (VII) may be prepared from compounds of formula (VIII) by using a suitable protection reagent such as benzyl chloroformate in the presence of a base such as triethylamine in an appropriate solvent such as THF at a suitable temperature between 0° C. and the boiling point of the solvent.

Compounds of formula (VIII) may be prepared from a compound of formula (XI) by coupling with a compound of formula (IX) using reagents such as EDCI and HOBt in the presence of a base such as triethylamine in a suitable solvent such as THF at an appropriate temperature between 0° C. and the boiling point of the solvent. An alternative may be condensation of a compound of formula (XI) with a compound of formula (X) using a reagent such as bis(trimethylaluminum)-1,4-diazabicyclo[2.2.2]-octane in a suitable solvent such as THF at an appropriate temperature between 0° C. and the boiling point of the solvent.

Other features of the invention will become apparent in the course of the following descriptions of exemplary embodiments which are given for illustration of the invention and are not intended to be limiting thereof.

EXAMPLES

Analytical LC-MS Conditions
LC-MS Method 1

The Waters ZQ quadrupole mass spectrometer with a C18-reverse-phase column (30×4.6 mm Phenomenex Luna 3 µm particle size), elution with A: water+0.1% formic acid; B: MeCN+0.1% formic acid. Gradient:

| Gradient - Time | flow (mL/min) | % A | % B |
| --- | --- | --- | --- |
| 0.00 | 2.0 | 95 | 5 |
| 0.30 | 2.0 | 95 | 5 |
| 4.30 | 2.0 | 5 | 95 |
| 5.30 | 2.0 | 5 | 95 |
| 5.80 | 2.0 | 95 | 5 |
| 6.00 | 2.0 | 95 | 5 |

Detection—MS, UV (200 µl/min split to the ESI source with in-line HP1100 PDA detector)
MS ionization method—Electrospray (positive and negative ion)
LC-MS Method 2

Waters Micromass ZMD quadrupole mass spectrometer with a C18-reverse-phase column (30×4.6 mm Phenomenex Luna 3 µm particle size), elution with A: water+0.1% formic acid; B: MeCN+0.1% formic acid. Gradient:

| Gradient - Time | flow(mL/min) | % A | % B |
| --- | --- | --- | --- |
| 0.00 | 2.0 | 95 | 5 |
| 0.50 | 2.0 | 95 | 5 |
| 4.50 | 2.0 | 5 | 95 |
| 5.50 | 2.0 | 5 | 95 |
| 6.00 | 2.0 | 95 | 5 |

Detection—MS, ELS, UV (200 µl split to MS with in-line UV detector)
MS ionization method—Electrospray (positive and negative ion)
LC-MS Method 3

Waters Micromass ZQ2000 mass spectrometer with a C18-reverse-phase column (100×2.1 mm Acquity BEH with 1.7 µm particle size) maintained at 40° C., elution with A: water+0.1% formic acid; B: MeCN+0.1% formic acid. Alternatively, where specified, a C18-reverse-phase (100×2.1 mm Acquity UPLC BEH Shield 1.7 µm particle size) column was used.

Gradient:

| Gradient - Time | flow (mL/min) | % A | % B |
| --- | --- | --- | --- |
| 0.00 | 0.4 | 95 | 5 |
| 0.40 | 0.4 | 95 | 5 |
| 6.00 | 0.4 | 5 | 95 |
| 6.80 | 0.4 | 5 | 95 |
| 7.00 | 0.4 | 95 | 5 |
| 8.00 | 0.4 | 95 | 5 |

Detection—MS, UV PDA
MS ionization method—Electrospray (positive/negative ion).
LC-MS Method U2

Acquity H-Class (quaternary pump/PDA detector) plus QDa Mass Spectrometer with an Acquity UPLC BEH C18-reverse-phase column (1.7 µm particle size, 50×2.1 mm at 50° C.), elution with A: water+0.1% formic acid; B: MeCN+0.1% formic acid.

Gradient:

| Gradient - Time | flow (mL/min) | % A | % B |
| --- | --- | --- | --- |
| 0.00 | 1.0 | 97 | 3 |
| 1.50 | 1.0 | 1 | 99 |
| 1.90 | 1.0 | 1 | 99 |
| 2.00 | 1.0 | 97 | 3 |
| 2.50 | 1.0 | 97 | 3 |

Detection—MS, UV
MS ionization method—Electrospray (positive and negative ion).
LC-MS Method 7

HP1100 (quaternary pump/PDA detector) plus ZQ Mass Spectrometer with a Phenomenex Luna C18(2) 3µ, 30×4.6 mm column, elution with A: water+0.1% formic acid; B: MeCN+0.1% formic acid.

Gradient:

| Gradient - Time | flow | % A | % B |
| --- | --- | --- | --- |
| 0.00 | 2.0 | 95 | 5 |
| 0.30 | 2.0 | 95 | 5 |
| 4.30 | 2.0 | 5 | 95 |
| 5.30 | 2.0 | 5 | 95 |
| 5.80 | 2.0 | 95 | 5 |
| 6.00 | 2.0 | 95 | 5 |

Detection—MS, UV
MS ionization method—Electrospray (positive and negative ion)
Abbreviations Used in the Experimental Section:
DCM Dichloromethane
DIPEA Di-isopropylethylamine
DMAP 4-(Dimethylamino)pyridine
DMF N,N-dimethylformamide
DMSO Dimethylsulphoxide
EDCI 1-Ethyl-3-(3-dimethylaminopropyl)carbodiimide hydrochloride
Et$_2$O Diethyl ether
EtOAc Ethyl acetate
h Hour
HOBt 1-Hydroxybenzotriazole hydrate
HPLC High performance liquid chromatography
IMS Industrial methylated spirits
LC-MS Liquid chromatography-mass spectrometry
MeCN Acetonitrile
MDAP Mass Directed Automatic Purification Min Minutes
NBS N-Bromosuccinimide
Rt Retention time
RT Room temperature
THF Tetrahydrofuran In the procedures that follow, some of the starting materials are identified through an "Intermediate" or "Example" number. The starting material may not necessarily have been prepared from the batch referred to.

When reference is made to the use of a "similar" or "analogous" procedure such a procedure may involve minor variations, for example reaction temperature, reagent/solvent amount, reaction time, work-up conditions or chromatographic purification conditions.

The invention will now be further described by the following examples.

Example 1

2'-(4-Cyano-phenyl)-2-methyl-5-oxo-1-(3-trifluoromethyl-phenyl)-2,5-dihydro-1H,2'H-[3,3']bipyrazolyl-4-carboxylic acid ethyl ester Intermediate A

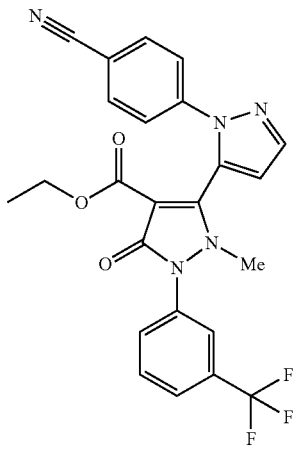 [SMILES: CCOC(=O)c1c(-c2ccnn2-c2ccc(C#N)cc2)n(C)n(-c2cccc(C(F)(F)F)c2)c1=O]

2-(4-Cyano-phenyl)-2H-pyrazole-3-carboxylic acid

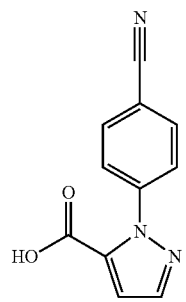 [SMILES: N#Cc1ccc(-n2nccc2C(=O)O)cc1]

A mechanically stirred solution of 2,2,6,6-tetramethylpiperidine (42.5 mL, 35.57 g, 0.252 mol) in dry THF (100 mL) was cooled to −40° C. and n-butyllithium (2.5M solution in hexanes, 96 mL, 0.24 mol) was added at such a rate that the temperature remained below −30° C. The solution was then stirred for 40 min at around −30° C. and finally cooled to −73° C. A solution of 4-pyrazol-1-yl-benzonitrile (33.84 g, 0.20 mmol) in anhydrous THF (250 mL) was added slowly, keeping the temperature below −65° C. A yellow precipitate formed and the resulting slurry was stirred between −65° C. and −73° C. for 60 min. Carbon dioxide pellets (approximately 100 g, 2.27 mol) were then added to the reaction mixture over 5 min, giving an initial exotherm to −50° C., followed by re-cooling to −70° C. The resulting slurry was allowed to warm slowly to +10° C. over 1.5 hr. The suspension was then poured into vigorously stirred 10% w/w aqueous citric acid solution and EtOAc (500 mL) and 1M hydrochloric acid (300 mL) added to give a two-phase solution with an aqueous layer at pH 3. The aqueous layer was separated and further extracted with EtOAc (2×200 mL). The combined organic extracts were washed with 1M hydrochloric acid (200 mL), saturated brine (100 mL), dried over $Na_2SO_4$, and the solvents evaporated to give the crude acid as a yellow solid. This was re-dissolved in 0.5M aqueous sodium hydroxide (600 mL) and the solution washed with DCM (2×150 mL) to give a colorless aqueous solution. This was acidified to pH 1 by the addition of conc. HCl, resulting in the formation of a white precipitate, which was collected by filtration, washed with water (50 mL) and dried in vacuo at 50° C./10 mbar over phosphorus pentoxide to give Intermediate A as a white solid; 34.42 g, 80% yield.
LCMS (Method U2): Rt=1.16 min, m/z 214 [M+H]+

Intermediate B 2-(4-Cyano-phenyl)-2H-pyrazole-3-carboxylic acid N'-(3-trifluoromethyl-phenyl)-hydrazide

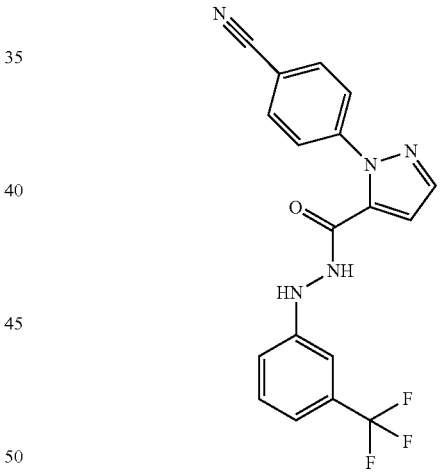

HOBt (11.60 g, 75.72 mmol) was added at RT to a vigorously stirred, slightly cloudy, solution of Intermediate A (12.60 g, 59.10 mmol) in a mixture of dry DCM (125 mL) and dry THF (190 mL). EDCI (14.70 g, 76.76 mmol) was then added, followed by $Et_3N$ (19.0 mL, 136.3 mmol) to give a thick slurry. A suspension of 3-(trifluoromethyl) phenylhydrazine hydrochloride (13.20 g, 62.09 mmol) in dry THF (50 mL) was then added and the resulting slurry stirred at RT for 20 hr. The mixture was poured into water (1 L) with vigorous stirring, and the resulting suspension stirred at RT for 30 min. The suspended solid was collected by filtration through a porosity-3 glass sinter filter funnel, the filter cake washed with water (50 mL) and sucked dry. The solid was then vacuum dried at 45° C./10 mbar over phosphorus pentoxide in a vacuum oven, to give Intermediate B as an off-white solid; 14.76 g, 67% yield.
LCMS (Method 7): Rt=3.18 min, m/z 372 [M+H]+

Intermediate C

N'-[2-(4-Cyano-phenyl)-2H-pyrazole-3-carbonyl]-N-(3-trifluoromethyl-phenyl)-hydrazinecarboxylic acid benzyl ester

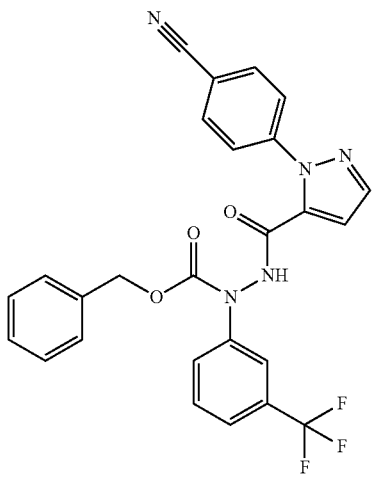 [SMILES: N#Cc1ccc(-n2nccc2C(=O)NN(C(=O)OCc2ccccc2)c2cccc(C(F)(F)F)c2)cc1]

A slightly cloudy solution of Intermediate B (7.50 g, 20.20 mmol) and Et₃N (7.40 mL, 5.37 g, 53.09 mmol) in dry THF (225 mL) was placed in a slightly chilled water bath at approximately 20° C. Benzyl chloroformate (3.50 mL, 4.18 g, 24.53 mmol) was added via syringe, at such a rate as to maintain the reaction mixture temperature below 26° C. After complete addition, the mixture was allowed to reach ambient temperature and was stirred for 22 hr. EtOAc (500 mL) was added, and the resulting solution washed with water (2×100 mL), saturated brine (100 mL), dried over Na₂SO₄ and the solvents evaporated to give the crude product as an orange gum. This was purified by column chromatography on silica gel (200 g cartridge, 0-10% EtOAc in DCM gradient eluent) to give Intermediate C as an off-white foam; 8.53 g, 83% yield.

LCMS (Method U2): Rt=2.08 min, m/z 506 [M+H]+

Intermediate D

N'-[2-(4-Cyano-phenyl)-2H-pyrazole-3-carbonyl]-N'-methyl-N-(3-trifluoromethyl-phenyl)-hydrazinecarboxylic acid benzyl ester

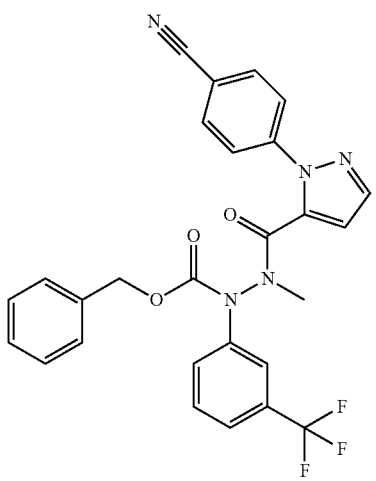 [SMILES: CN(C(=O)c1ccnn1-c1ccc(C#N)cc1)N(C(=O)OCc1ccccc1)c1cccc(C(F)(F)F)c1]

A solution of Intermediate C (8.53 g, 16.88 mmol) in dry DMF (85 mL) was placed in a slightly chilled water bath at approximately 20° C. Sodium hydride (60% dispersion in mineral oil, 0.88 g, 22.0 mmol) was added in four approximately equal portions over 20 min, a vigorous gas evolution and precipitate formation being noted with each addition. The resulting suspension was stirred for 1 hr, then iodomethane (1.20 mL, 2.74 g, 19.28 mmol) was added via syringe, and the resulting mixture stirred for 2 hr. Water (200 mL), and EtOAc (500 mL) were added, and the mixture stirred at RT until gas evolution ceased. The organic layer was separated and washed with water (2×100 mL), saturated brine (100 mL), dried over Na2SO4, filtered and the solvent evaporated to give the crude product as an orange gum. This was purified by column chromatography on silica gel (200 g cartridge, 0-10% EtOAc in DCM gradient eluent) to give pure Intermediate D as a colourless glass/gum; 5.95 g, 67%. In addition, fractions containing Intermediate D with close-running impurities were isolated, re-combined and evaporated to give a quantity of impure product; 1.70 g. This was re-purified by repeat column chromatography on silica gel (80 g cartridge, 0-10% EtOAc in DCM gradient eluent), which allowed the isolation of a second crop of pure Intermediate D as a colourless glass; 0.54 g, 6% yield. Total 6.49 g, 73% yield.

LCMS (Method 7): Rt=3.92 min, m/z 520 [M+H]+

Intermediate E 2-(4-Cyano-phenyl)-2H-pyrazole-3-carboxylic acid N-methyl-N'-(3-trifluoromethyl-phenyl)-hydrazide

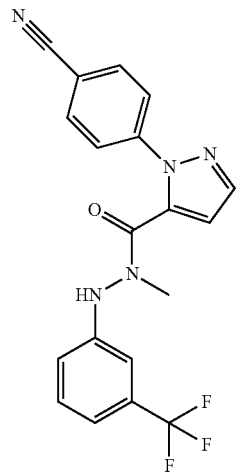 [SMILES: CN(Nc1cccc(C(F)(F)F)c1)C(=O)c1ccnn1-c1ccc(C#N)cc1]

A solution of Intermediate D (5.90 g, 11.36 mmol) in IMS (150 mL) was degassed by evacuation to approximately 400 mbar followed by re-filling with dry argon. This was repeated twice. The resulting degassed solution was charged to a clean reaction vessel containing palladium on activated charcoal catalyst (10% w/w Pd, 0.36 g, 0.34 mmol) and the mixture placed under a hydrogen atmosphere with a hydrogen balloon via an evacuation, hydrogen refill sequence. The mixture was stirred for 3 h then the hydrogen atmosphere was discharged and replace with argon using an evacuation/argon refill procedure. The catalyst was removed by filtration through Celite®, the filter cake being rinsed with extra IMS (50 mL) under a flow of nitrogen. The resulting solution was evaporated to give the crude product as a white solid. This was purified by column chromatography on silica gel (200 g cartridge, 0-20% EtOAc in DCM gradient eluent) to give Intermediate E as a white solid; 2.93 g, 66% yield.

LCMS (Method U2): Rt=1.71 min, m/z 386 [M+H]+

Intermediate F

3-[N'-[2-(4-Cyano-phenyl)-2H-pyrazole-3-carbonyl]-N'-methyl-N-(3-trifluoromethyl-phenyl)-hydrazino]-3-oxo-propionic acid ethyl ester

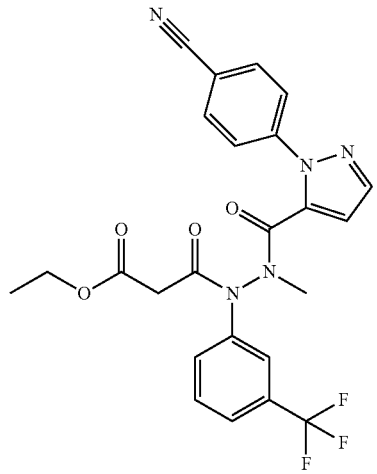 [SMILES: CCOC(=O)CC(=O)N(c1cccc(C(F)(F)F)c1)N(C)C(=O)c1ccnn1-c1ccc(C#N)cc1]

A solution of Intermediate E (13.09 g, 33.97 mmol), pyridine (3.35 mL, 3.28 g, 37.34 mmol) and catalytic DMAP (41 mg, 0.336 mmol) in dry THF (260 mL) was treated with ethyl malonyl chloride (4.78 mL, 5.62 g, 37.34 mmol) and the resulting solution warmed to 50° C. under reflux for 3 hr. Further portions of pyridine (3.35 mL, 3.28 g, 37.34 mmol) and ethyl malonyl chloride (4.78 mL, 5.62 g, 37.34 mmol) were added, and heating continued for a further 15 hr. Third portions of pyridine (3.35 mL, 3.28 g, 37.34 mmol) and ethyl malonyl chloride (4.78 mL, 5.62 g, 37.34 mmol) were then added and heating continued for a final 4 hr. The mixture was cooled to RT and solvents evaporated. The resulting orange gum was purified by column chromatography on silica gel (300 g cartridge, 0-20% EtOAc in DCM gradient eluent) giving Intermediate F as a yellow glass after vacuum drying; 14.47 g, 85% yield.

LCMS (Method U2): Rt=1.74 min, m/z 522 [M+Na]+

2'-(4-Cyano-phenyl)-2-methyl-5-oxo-1-(3-trifluoromethyl-phenyl)-2,5-dihydro-1H,2'H-[3,3']bipyrazolyl-4-carboxylic acid ethyl ester Solid sodium ethoxide (2.02 g, 29.68 mmol) was added to a solution of Intermediate F (7.43 g, 14.88 mmol) in absolute ethanol (120 mL) and the solution stirred at RT for 24 hr. The resulting mixture was concentrated in vacuo to approximately 40 mL and the residue diluted with EtOAc (300 mL). The solution was washed sequentially with 10% w/w aqueous citric acid solution (50 mL) and saturated brine, dried over Na₂SO₄, filtered and the solvents evaporated to give a yellow gum. This was purified by column chromatography on silica gel (200 g cartridge, 0-80% EtOAc in DCM gradient eluent) to give the title compound as a white solid; 5.48 g, 76% yield.

LCMS (Method 3): Rt=4.20 min, m/z 482.2 [M+H]+

$^1$H NMR (400 MHz, d6-DMSO): δ 8.06 (1H, d J=1.9 Hz), 7.98 (2H, d J=8.8 Hz), 7.89-7.81 (2H, m), 7.79-7.75 (2H, m), 7.66 (2H, d J=8.8 Hz), 7.09 (1H, d J=1.9 Hz), 3.84 (1H, dq J=10.8 Hz and 7.1 Hz), 3.72 (1H, dq J=10.8 Hz and 7.1 Hz), 3.28 (3H, s) 0.89 (3H, t J=7.1 Hz).

Intermediate G

2'-(4-Cyano-phenyl)-2-methyl-5-oxo-1-(3-trifluoromethyl-phenyl)-2,5-dihydro-1H,2'H-[3,3']bipyrazolyl-4-carboxylic acid

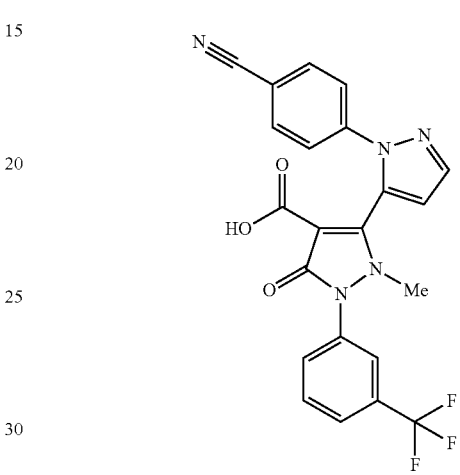

Lithium hydroxide monohydrate (1.01 g, 24.07 mmol) was added to a stirred solution of Pyr-INT8 (5.48 g, 11.38 mmol) in a mixture of THF (140 mL) and water (30 mL) and the resulting cloudy solution stirred at RT for 15 hr. The reaction mixture was concentrated in vacuo to remove THF and the residue partitioned between EtOAc (300 mL) and 10% w/w aqueous citric acid solution (150 mL). The acidic aqueous layer (pH 2-3) was separated and further extracted with EtOAc (2×100 mL). The organic layers were combined, washed with saturated brine (100 mL), dried over Na2SO4, filtered and evaporated to give a yellow gum/glass. This was purified by column chromatography on silica gel (200 g cartridge, 0-5% methanol in DCM gradient eluent) to give Pyr-INT9 as a white solid; 4.43 g, 85% yield.

LCMS (Method U2): Rt=1.29 min, m/z 454 [M+H]+

$^1$H NMR (400 MHz, CD₃OD): δ 7.97 (1H, d, J=1.8 Hz), 7.89-7.80 (5H, m), 7.76-7.73 (1H, m), 7.66-7.63 (2H, m), 7.03 (1H, d, J=1.8 Hz), 3.36 (3H, s).

Intermediate H (S)-1-(5-Dimethylaminomethyl-[1,3,4]oxadiazol-2-yl)-ethylamine TFA salt

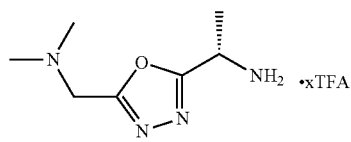

Intermediate H1

{(S)-2-[N'-(2-Dimethylamino-acetyl)-hydrazino]-1-methyl-2-oxo-ethyl}-carbamic acid tert-butyl ester

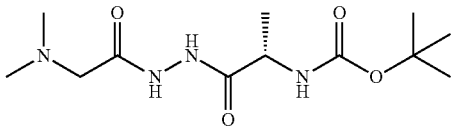 [SMILES: C[C@H](NC(=O)OC(C)(C)C)C(=O)NNC(=O)CN(C)C]

A solution of Boc-Alanine (1 g, 5.3 mmol) was formed in DCM (40 mL). EDC hydrochloride (1.02 g, 5.3 mmol) was added followed by 1-hydroxybenzotriazole hydrate (716 mg, 5.3 mmol) and the mixture stirred for 5 mins. N,N-diisopropylethylamine (1.85 mL, 10.6 mmol) was added giving a yellow solution. Girard's Reagent D (1.1 g, 5.8 mmol) was added and the mixture stirred for 24 h. The mixture was partitioned between DCM and sat. aqueous sodium bicarbonate. The organic phase was isolated using a phase separation cartridge and evaporated. Purification by flash column chromatography (40 g Si cartridge) eluting with a gradient of 0-10% (2N NH3 in MeOH) in DCM gave Intermediate H1 as a colourless gum (870 mg, 57%).

$^1$H NMR (400 MHz, CDCl$_3$): δ 8.63 (1H, br s), 5.00-4.89 (1H, m), 4.34-4.22 (1H, m), 3.08 (2H, s), 2.34 (6H, s), 1.46 (9H, s), 1.41 (3H, d, J=7.1 Hz).

Intermediate H2

[(S)-1-(5-Dimethylaminomethyl-[1,3,4]oxadiazol-2-yl)-ethyl]-carbamic acid tert-butyl ester

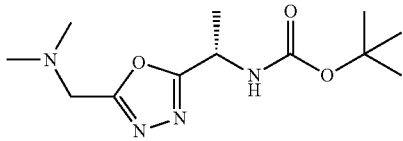 [SMILES: C[C@H](NC(=O)OC(C)(C)C)c1nnc(CN(C)C)o1]

A solution of Intermediate H1 (288 mg, 1 mmol) was formed in DCM (10 mL). Burgess Reagent (357 mg, 1.5 mmol) was added and the mixture stirred over night at ambient temperature. The mixture was partitioned between water and DCM. The organic phase was isolated using a phase separation cartridge and evaporated. Purification by flash column chromatography (12 g Si cartridge) eluting with a gradient of 0-10% (2N NH3 in MeOH) in DCM gave Intermediate H2 as a colourless oil (260 mg, 96%).

$^1$H NMR (400 MHz, CDCl$_3$): δ 5.09 (2H, br s), 3.75 (2H, s), 2.35 (6H, s), 1.59 (3H, m, partially obscured by water peak), 1.45 (9H, s).

(S)-1-(5-Dimethylaminomethyl-[1,3,4]oxadiazol-2-yl)-ethylamine TFA salt

Intermediate H2 (230 mg, 0.85 mmol) was dissolved in DCM (6 mL). Trifluoroacetic acid (2 mL) was added and the mixture stirred for 2.5 h at ambient temperature. Evaporation gave Intermediate H containing ~3 eq of TFA (530 mg, quant).

$^1$H NMR (400 MHz, d6-DMSO): δ 8.93 (3H, br s), 4.95-4.86 (1H, m), 4.77 (2H, s), 2.90 (6H, s), 1.61 (3H, d, J=7.0).

Intermediate I (S)-1-(5-Dimethylaminomethyl-oxazol-2-yl)-ethylamine TFA salt

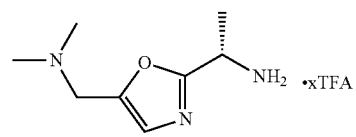

Intermediate I1

((S)-1-Prop-2-ynylcarbamoyl-ethyl)-carbamic acid tert-butyl ester

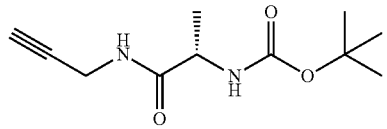 [SMILES: C#CCNC(=O)[C@H](C)NC(=O)OC(C)(C)C]

A solution of Boc-alanine (1 g, 5.3 mmol) was formed in DCM (40 mL). EDC hydrochloride (1.02 g, 5.3 mmol) was added followed by 1-hydroxybenzotriazole hydrate (716 mg, 5.3 mmol) and the mixture stirred for 5 mins. Propargyl amine (407 μL, 6.4 mmol) was added and the mixture stirred for 27 h at ambient temperature. The mixture was partitioned between DCM and water. The organic phase was isolated using a phase separation cartridge and evaporated. Purification by flash column chromatography (40 g Si cartridge) eluting with a gradient of 0-100% EtOAc in DCM gave Intermediate I1 as a white solid (1.04 g, 87%).

$^1$H NMR (400 MHz, CDCl$_3$): δ 6.39 (1H, br s), 4.89 (1H, br s), 4.19-4.09 (1H, m), 4.09-4.00 (2H, m), 2.22 (1H, t, J=2.5 Hz), 1.45 (9H, s), 1.36 (3H, d, J=7.1 Hz).

Intermediate I2

[(S)-1-(5-Bromomethyl-oxazol-2-yl)-ethyl]-carbamic acid tert-butyl ester

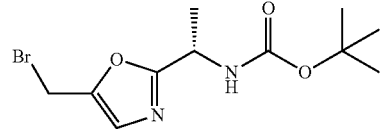 [SMILES: C[C@H](NC(=O)OC(C)(C)C)c1ncc(CBr)o1]

A solution of Intermediate D1 (500 mg, 2.21 mmol) was formed in chloroform (10 mL). Gold (III) chloride (7 mg, 0.022 mmol) was added and the mixture stirred at ambient temperature for 4 hours before cooling to 0° C. 2,6-Lutadine (260 mg, 2.43 mmol) was added followed by bromine (350 mg, 2.21 mmol) in chloroform (2 mL). The mixture was allowed to warm to RT overnight. The mixture was diluted with DCM and washed with an aqueous sodium thiosulphate solution, sat. aqueous sodium bicarbonate solution, brine and then dried over MgSO$_4$. Purification by flash column chromatography (24 g Si cartridge) eluting with a gradient of 0-100% EtOAc in cyclohexane gave Intermediate I2 as a colourless oil (320 mg, 47%).

$^1$H NMR (400 MHz, CDCl$_3$): δ 6.99 (1H, s), 5.10 (1H, br s), 4.95 (1H, br s), 4.46 (2H, s), 1.54 (3H, d, partially obscured by water), 1.45 (9H, s).

Intermediate I3

[(S)-1-(5-Dimethylaminomethyl-oxazol-2-yl)-ethyl]-carbamic acid tert-butyl ester

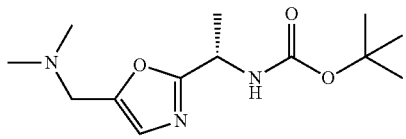 [SMILES: C[C@H](NC(=O)OC(C)(C)C)c1ncc(CN(C)C)o1]

Intermediate I2 (320 mg, 1.04 mmol) was dissolved in a solution of 2N NH$_3$ in THF and stirred at ambient temperature for 1 hour. The mixture was filtered through celite to remove the white precipitate and the filtrate was evaporated. Purification by flash column chromatography (12 g Si cartridge) eluting with a gradient of 0-100% EtOAc in cyclohexane gave Intermediate I3 as a yellow oil (200 mg, 73%).

$^1$H NMR (400 MHz, CDCl$_3$): δ 6.85 (1H, s), 5.17 (1H, br s), 4.93 (1H, br s), 3.50 (2H, s), 2.27 (6H, s), 1.52 (3H, d, J=6.9 Hz), 1.44 (9H, s).

(S)-1-(5-Dimethylaminomethyl-oxazol-2-yl)-ethyl-amine TFA salt

Intermediate I3 (200 mg, 0.76 mmol) was dissolved in DCM (6 mL). Trifluoroacetic acid (2 mL) was added and the mixture stirred for 2 h at ambient temperature. Evaporation gave Intermediate I containing ~4 eq of TFA (490 mg, quant).

$^1$H NMR (400 MHz, d6-DMSO): δ 8.75 (3H, br s), 7.46 (1H, s), 4.71 (1H, br s), 4.50 (2H, s), 2.79 (6H, s), 1.56 (3H, d, J=6.9 Hz).

Intermediate J (S)-1-(5-Dimethylaminomethyl-oxazol-2-yl)-2-methyl-propylamine TFA salt

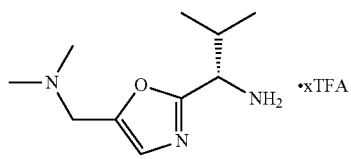

Intermediate J was synthesised from Boc-valine using a similar procedure to that for Intermediate I.

$^1$H NMR (400 MHz, d6-DMSO): δ 8.77 (3H, br s), 7.49 (1H, s), 4.52 (2H, s), 4.46, (1H, s), 2.78 (6H, s), 2.31-2.16 (1H, m), 1.01 (3H, d, J=6.8 Hz), 0.87 (3H, d, J=6.8 Hz).

Intermediate K 1-(5-Dimethylaminomethyl-oxazol-2-yl)-1-methyl-ethylamine TFA salt

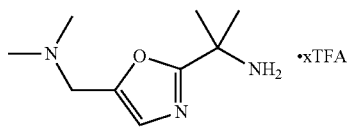

Intermediate K was synthesized from Boc-2-amino-2-methyl-propionic acid using a similar procedure to that for Intermediate I.

$^1$H NMR (400 MHz, d6-DMSO): δ 8.88 (3H, br s), 7.47 (1H, s), 4.51 (2H, s), 2.79 (6H, s), 1.66 (6H, s).

Intermediate L (S)-1-[5-(2-Dimethylamino-ethyl)-oxazol-2-yl]-ethylamine

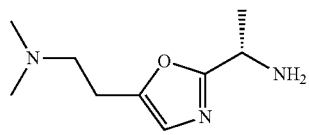

Intermediate L1

[(S)-1-(5-Cyanomethyl-oxazol-2-yl)-ethyl]-carbamic acid tert-butyl ester

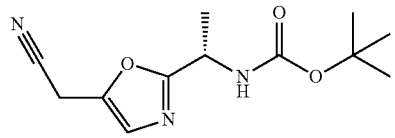 [SMILES: C[C@H](NC(=O)OC(C)(C)C)c1ncc(CC#N)o1]

To Intermediate I2 (970 mg, 3.18 mmol) in DMF (10 mL) was added NaCN (310 mg, 6.36 mmol, 2 eq). The reaction mixture was warmed to 70° C. for two hours, then partitioned (water 150 mL/EtOAc×3). Combined EtOAc extracts were dried (MgSO$_4$) and evaporated. Column chromatography on 40 g silica eluting with 0-100% EtOAc in cyclohexane, produced 110 mg of Intermediate L1 at ca. 90% purity.

$^1$H NMR (300 MHz, CDCl$_3$): δ 6.68 (1H, s), 5.01-4.78 (1H, m), 3.80 (2H, d, J=1.05 Hz), 1.48 (3H, d, J=14.37 Hz), 1.45 (9H, s).

Intermediate L2

{(S)-1-[5-(2-Amino-ethyl)-oxazol-2-yl]-ethyl}-carbamic acid tert-butyl ester

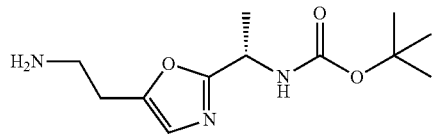 [SMILES: C[C@H](NC(=O)OC(C)(C)C)c1ncc(CCN)o1]

Intermediate L1 (110 mg) in MeOH (50 mL) was passed over solid supported rhodium on carbon at 80 bar/70° C. at 1 ml per minute in an H-cube, for two passes. The resulting product was evaporated to dryness giving impure Intermediate L2 which was used directly in the next step.

LCMS (Method U2): Rt=0.66 min, m/z=256.1 [M+H]+.

Intermediate L3

{(S)-1-[5-(2-Dimethylamino-ethyl)-oxazol-2-yl]-ethyl}-carbamic acid tert-butyl ester

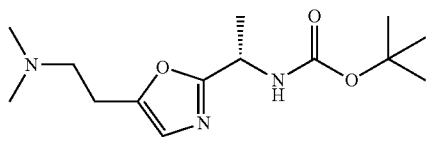 [SMILES: C[C@H](NC(=O)OC(C)(C)C)c1ncc(CCN(C)C)o1]

A solution of the crude Intermediate L2 from the previous step and formaldehyde (210 mg, ca. 3 eq), 37% aqueous soln. was dissolved in DCM (20 mL) and cooled (−10° C., salt/ice bath) for 20 mins before sodium triacetoxyborohydride (480 mg, ca. 5 eq) was added at −10° C. This mixture was left stirring overnight to warm to +20° C. The mixture was partitioned (DCM×3/satd. NaHCO$_3$), the combined DCM layers were dried (MgSO$_4$) and evaporated. (ca. 80% pure, 28 mg, 12% yield over 2 steps).

$^1$H NMR (300 MHz, CDCl$_3$): δ 6.69 (1H, s), 4.91 (1H, br s), 2.80 (2H, t, J=7.72 Hz), 2.57 (2H, t, J=8.13 Hz), 2.27 (6H, s), 1.50 (3H, d, J=6.93 Hz), 1.45 (9H, s).

(S)-1-[5-(2-Dimethylamino-ethyl)-oxazol-2-yl]-ethylamine

Intermediate L3 was dissolved in DCM (2 mL) and TFA (1 mL) was added. The reaction mixture was left at 20° C. for 1 h then evaporated to dryness and loaded onto SCX-2 ion exchange resin eluting with 10% MeOH in DCM followed by 2M NH$_3$ in MeOH. The ammonia solution was evaporated to dryness to yield 17 mg of the title compound at ~80% purity.

$^1$H NMR (300 MHz, CDCl$_3$): δ 6.69 (1H, s), 4.12 (1H, q, J=6.87 Hz), 2.82 (1H, t, J=7.67 Hz), 2.61 (2H, t, J=8.15 Hz), 2.30 (6H, s), 1.49 (3H, d, J=6.83 Hz)

Intermediate M

Trans-4-(5-dimethylaminomethyl-oxazol-2-yl)-cyclohexylamine hydrochloride salt

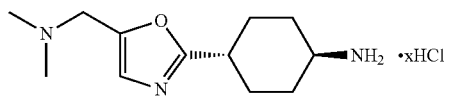 [SMILES: CN(C)Cc1cnc([C@H]2CC[C@H](N)CC2)o1]

Intermediate M was synthesized from trans-4-tert-butoxycarbonylamino-cyclohexanecarboxylic acid using a similar procedure to that for Intermediate I.

$^1$H NMR (400 MHz, d6-DMSO): δ 8.27 (3H, br.s), 7.28 (1H, s), 6.02 (1H, br.s) 4.40 (2H, d), 3.01 (1H, m), 2.74 (2H, s), 2.69 (6H, d), 2.09 (4H,m), 1.51 (4H, m)

Intermediate N

Trans-3-(5-Dimethylaminomethyl-oxazol-2-yl)-cyclobutylamine hydrochloride salt

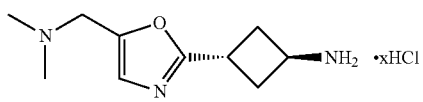

Intermediate N was synthesized from trans-3-tert-Butoxycarbonylamino-cyclobutanecarboxylic acid using a similar procedure to that for Intermediate I.

$^1$H NMR (400 MHz, d6-DMSO): δ 8.66 (2H, br.s), 7.34 (1H, s), 6.70 (1H, br.s) 4.42 (2H, d), 3.84 (2H, m), 2.71 (6H, d), 2.60 (4H, t), 1.59 (2H,s)

The following compounds were prepared from the starting materials using analogous procedures to that described for Intermediate I1 and Intermediate I.

| Interm. | Structure | Starting materials | | Data |
|---|---|---|---|---|
| O | 4-Trans-amino-cyclohexanecarboxylic acid (1-methyl-piperidin-4-yl)-amide TFA salt | 1-Methyl-piperidin-4-ylamine | 4-Trans-tert-butoxy-carbonyl-amino-cyclo-hexane-carboxylic acid | $^1$H NMR (400 MHz, d6-DMSO): δ 10.56 (1H, br s), 8.04-7.95 (4H, m), 3.73-3.65 (5H, m), 3.57 (3H, s), 3.52-3.44 (2H, m), 3.38-3.32 (2H, m), 3.26-3.20 (1H, m), 3.09-2.90 (3H, m), 2.72-2.66 (5H, m). |

-continued

| Interm. | Structure | Starting materials | | Data |
|---|---|---|---|---|
| P | 4-Amino-cyclohexanecarboxylic acid 1-methyl-piperidin-4-yl ester | 1-Methyl-piperidin-4-ol | 4-Trans-tert-butoxy-carbonyl-amino-cyclo-hexane-carboxylic acid | $^1$H NMR (400 MHz, CDCl$_3$): δ 4.81-4.73 (1H, m), 2.73-2.58 (3H, m), 2.30-2.17 (6H, m), 2.13 (2h, br s), 2.02-1.84 (6H, m), 1.74-1.65 (2H, m), 1.53-1.41 (2H, m), 1.19-1.08 (2H, m). |
| Q | (4-Trans-amino-cyclohexyl)-(4-dimethylamino-piperidin-1-yl)-methanone | Dimethyl-piperidin-4-yl-amine | 4-Trans-tert-butoxy-carbonyl-amino-cyclo-hexane-carboxylic acid | $^1$H NMR (400 MHz, CDCl$_3$): δ 4.64 (1H, d, J = 13.4 Hz), 3.94 (1H, d, J = 13.4 Hz), 3.06-2.98 (1H, m), 2.76-2.67 (1H, m), 2.60-2.51 (1H, m), 2.47-2.30 (2H, m), 2.29 (6H, s), 1.96-1.56 (8H, m), 1.45-1.31 (2H, m), 1.19-1.05 (2H, m). |
| R | 4-Trans-amino-cyclohexane-carboxylic acid 2-dimethylamino-ethyl ester | 2-Dimethyl-amino-ethanol | 4-Trans-tert-butoxy-carbonyl-amino-cyclo-hexane-carboxylic acid | $^1$H NMR (400 MHz, CDCl$_3$): δ 4.16 (2H, t, J = 5.7 Hz), 2.71-2.62 (1H, m), 2.55 (2H, t, J = 5.7 Hz), 2.31-2.23 (7H, m), 2.02-1.88 (4H, m), 1.53-1.43 (2H, m), 1.16-1.05 (2H, m). |

-continued

| Interm. | Structure | Starting materials | | Data |
|---|---|---|---|---|
| S | Dimethylamino-acetic acid 4-amino-cyclohexyl ester | (4-Hydroxy-cyclohexyl)-carbamic acid tert-butyl ester | Dimethyl-amino-acetic acid | ¹H NMR (400 MHz, CDCl₃): δ 4.80-4.72 (1H, m), 3.14 (2H, s), 2.95-2.74 (3H, m), 2.34 (6H, s), 2.04-1.89 (4H, m), 1.50-1.40 (2H, m), 1.34-1.23 (2H, m). |
| T | (S)-2-Amino-propionic acid 1-methyl-piperidin-4-ylmethyl ester | (1-Methyl-piperidin-4-yl)-methanol | (S)-2-tert-Butoxycarbonyl-amino-propionic acid | LCMS (Method U2) Rt = 0.16 min, m/z = 201 [M + H]+. |
| U | (4-Amino-piperidin-1-yl)-(1-methyl-piperidin-4-yl)-methanone | Piperidin-4-yl-carbamic acid tert-butyl ester | 1-Methyl-piperidine-4-carboxylic acid | LCMS (Method U2) Rt = 0.18 min, m/z = 226 [M + H]+. |
| V | 4-Trans-amino-cyclohexane-carboxylic acid (2-dimethyl-amino-ethyl)-amide TFA salt | N,N-Dimethyl-ethylene-diamine | 4-Trans-tert-butoxy-carbonyl-aminocyclo-hexane-carboxylic acid | ¹H NMR (400 MHz, d6-DMSO): δ 9.72 (1H, br s), 8.11 (1H, m), 7.88 (3H, br s), 3.42-3.37 (2H, m), 3.17-3.10 (3H, m), 2.81 (6H, d, J = 5 Hz), 2.13-2.02 (1H, m), 2.02-1.95 (2H, m), 1.88-1.80 (2H, m), 1.49-1.22 (4H, m). |

-continued

| Interm. | Structure | Starting materials | | Data |
|---|---|---|---|---|
| W | 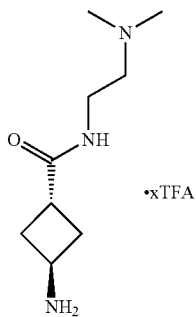<br>3-Trans-amino-cyclobutane-carboxylic acid (2-dimethyl-amino-ethyl)-amide TFA salt | N,N-Dimethyl-ethylene-diamine | 3-Trans-tert-butoxy-carbonyl-amino-cyclo-butane-carboxylic acid | $^1$H NMR (400 MHz, d6-DMSO): δ 8.14 (1H, m), 8.03 (3H, br s), 3.81-3.72 (1H, m), 3.41-3.37 (2H, m), 3.15-3.10 (2H, m), 3.07-2.99 (1H, m), 2.81 (6H, d, J = 4.7 Hz), 2.41-2.34 (2H, m), 2.30-2.22 (2H, m). |
| X | 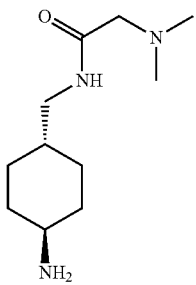<br>N-(Trans-4-amino-cyclohexyl-methyl)-2-dimethylamino-acetamide | (Trans-4-amino-methyl-cyclo-hexyl)-carbamic acid tert-butyl ester | Dimethyl-amino-acetic acid | $^1$H NMR (400 MHz, CDCl$_3$): δ 5.67 (1H, m), 4.46 (1H, br s), 3.76-3.69 (1H, m), 3.35 (1H, br s), 3.23-3.17 (1H, m), 3.05-3.00 (1H, m), 2.80 (6H, s), 2.05-1.99 (2H, m), 1.83-1.77 (2H, m), 1.61 (1H, br s), 1.22-0.97 (4H, m). |
| Y | 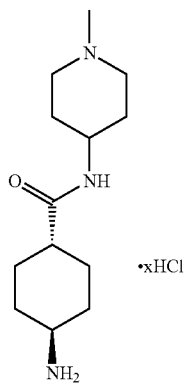<br>Trans-3-amino-cyclobutanecarboxylic acid (1-methyl-piperidin-4-yl)-amide hydrochloride salt | 1-Methyl-piperidin-4-ylamine | Trans-3-tert-butoxy-carbonyl-amino-cyclobutane-carboxylic acid | $^1$H NMR (400 MHz, CD$_3$OD): δ 4.00-3.87 (2H, m), 3.66 (3H, s), 3.58-3.51 (2H, m), 3.16-3.08 (2H, m), 2.90-2.87 (1H, m), 2.59-2.51 (2H, m), 2.43-2.35 (2H, m), 2.17-2.11 (2H, m), 2.05-2.98 (1H, m), 1.80-1.68 (2H, m). |
| Z | 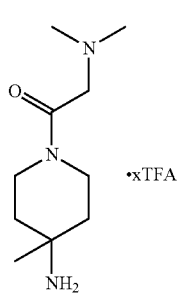<br>1-(4-Amino-4-methyl-piperidin-1-yl)-2-dimethylamino-ethanone TFA salt | (4-Methyl-piperidin-4-yl)-carbamic acid tert-butyl ester | Dimethyl-amino-acetic acid | LCMS (Method U1)<br>Rt = 0.11 min,<br>m/z = 200 [M + H]+. |

Example 2

2'-(4-Cyano-phenyl)-2-methyl-5-oxo-1-(3-trifluoromethyl-phenyl)-2,5-dihydro-1H,2'H-[3,3']bipyrazolyl-4-carboxylic acid (1-methyl-piperidin-4-yl)-amide

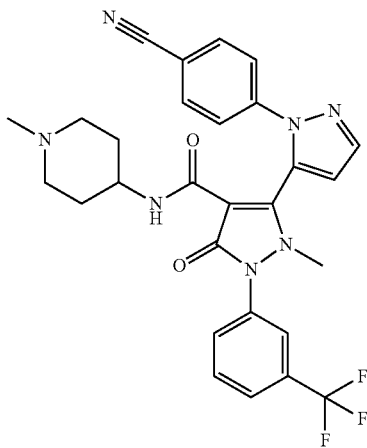 [SMILES: CN1CCC(NC(=O)c2c(-c3ccnn3-c3ccc(C#N)cc3)n(C)n(-c3cccc(C(F)(F)F)c3)c2=O)CC1]

Intermediate G (60 mg, 0.132 mmol), 4-amino-1-methylpiperidine (27 mg, 0.237 mmol) and DIPEA (51.6 mg, 0.40 mmol) were stirred in dry DMF (2 ml) at RT as HATU (76 mg, 0.20 mmol) was added. After stirring for 1 h the mixture was combined with a smaller scale reaction mixture (0.18× scale) for workup. EtOAc and aqueous sodium bicarbonate solution were added, which gave initially a 2 phase system with suspended solids. Further portions of EtOAc and also DCM were added until almost all solids had dissolved (total organic volume ca. 50 ml). The organic phase was separated, washed with water and brine, dried ($Na_2SO_4$), filtered and evaporated. The product was purified on a 5 g silica SPE cartridge eluting with 10% MeOH in DCM to afford the title compound as a white solid (66 mg, 77%).

LCMS (Method 3): Rt=3.20 min, m/z 550.3 [M+H]+

$^1$H NMR (400 MHz, d6-DMSO): δ 8.06-8.01 (2H, m), 7.94-7.80 (6H, m), 7.61 (2H, d J=8.8 Hz), 7.04 (1H, d J=1.9 Hz), 3.50-3.36 (1H, m), 3.29 (3H, s), 2.66-2.52 (2H, m), 2.28-2.04 (5H, m), 1.72-1.63 (1H, m), 1.54-1.45 (1H, m), 1.40-1.28 (1H, m), 1.26-1.12 (1H, m).

The following compounds were prepared by analogous procedures to that used in Examples 2. In the table below where rotameric signals have been identified in the NMR spectrum these have been labelled by *.

| Ex. | Structure | Amine | 1H NMR | LC-MS Method 3 |
|---|---|---|---|---|
| 3 | (structure shown) | Ethylamine | $^1$H NMR (400 MHz, d6-DMSO): δ 8.07-8.01 (2H, m), 7.93 (2H, d, J = 8.8 Hz), 7.91-7.77 (4H, m), 7.62 (2H, d, J = 8.8 Hz), 7.03 (1H, d, J = 1.9 Hz), 3.24 (3H, s), 3.08-2.92 (2H, m), 0.86 (3H, t J = 7.2 Hz). | Rt = 4.27 min, m/z = 481.2 [M + H]. |
| 4 | (structure shown) | (3aR,5R,6aS)-5-Aminohexahydrocyclopenta[c]pyrrole-2-carboxylic acid tert-butyl ester | $^1$H NMR (400 MHz, CDCl$_3$): δ 8.33 (1H, d J = 7.5 Hz), 7.92 (1H, d J = 1.9 Hz), 7.76 (2H, d J = 8.7 Hz), 7.70-7.58 (4H, m), 7.46-7.41 (1H, m), 7.37 (1H, s), 6.92 (1H, d J = 1.9 Hz), 4.27-4.14 (1H, m), 3.48-3.40 (2H, m), 3.24 (2H, br s), 2.99 (3H, s), 2.63-2.51 (2H, m), 2.37-2.20 (2H, m), 1.45 (9H, s), 1.36-1.20 (2H, m). | Rt = 5.05 min, m/z = 662.4 [M + H]+ |

| Ex. | Structure | Amine | 1H NMR | LC-MS Method 3 |
|---|---|---|---|---|
| 5 | 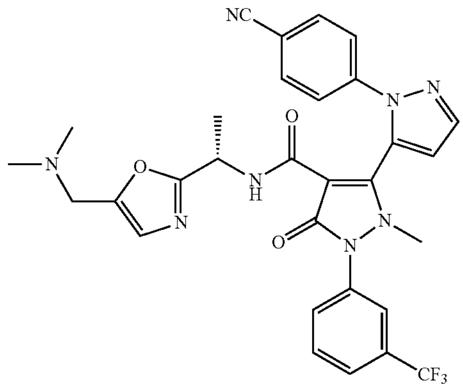 | Intermediate I | ¹H NMR (400 MHz, CDCl₃): δ 9.01-8.90 (1H*, 2xd J = 7.8 and 7.7 Hz), 7.94-7.90 (1H, m), 7.79-7.72 (2H, m), 7.70-7.58 (4H, m), 7.48-7.40 (1H, m), 7.38 (1H, s), 6.95-6.91 (1H*, 2xd J = 1.8 Hz), 6.86 (1H, s), 5.28-5.18 (1H, m), 3.54-3.42 (2H, m), 3.02-2.96 (3H*, 2xs), 2.26 (6H, s), 1.61-1.46 (3H*, 2xd J = 6.9 Hz) | Rt = 3.24 min, m/z = 605.3 [M + H]⁺ |
| 6 | 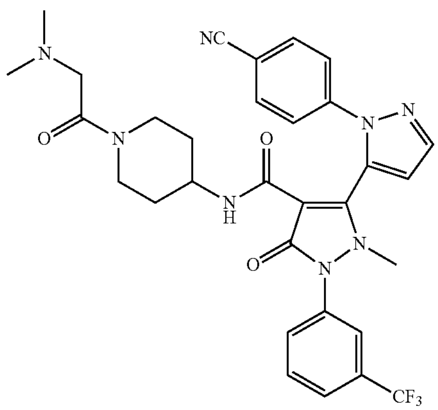 [SMILES: CN(C)CC(=O)N1CCC(NC(=O)c2c(-c3ccnn3-c3ccc(C#N)cc3)n(C)n(-c3cccc(C(F)(F)F)c3)c2=O)CC1] | 1-(4-Amino-piperidin-1-yl)-2-dimethyl-amino-ethanone | ¹H NMR (400 MHz, CDCl₃): δ 8.35-8.25 (1H, m), 7.94-7.92 (1H*, 2xs), 7.79-7.73 (2H, m), 7.72-7.58 (4H, m), 7.49-7.36 (2H, m), 6.93-6.90 (1H*, 2xs), 4.38-4.28 (1H, m), 4.06-3.92 (2H, m), 3.20-3.10 (2H, m), 3.08-2.98 (4H, m), 2.92-2.81 (1H, m), 2.26 (6H, m), 2.00-1.80 (2H, m), 1.50-1.29 (2H, m). | Rt = 3.21 min, m/z = 621.4 [M + H]+ |
| 7 | 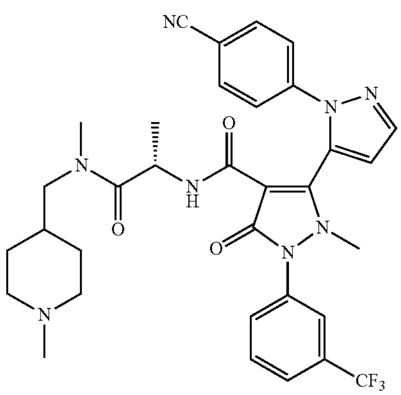 [SMILES: C[C@H](NC(=O)c1c(-c2ccnn2-c2ccc(C#N)cc2)n(C)n(-c2cccc(C(F)(F)F)c2)c1=O)C(=O)N(C)CC1CCN(C)CC1] | (S)-2-Amino-N-methyl-N-(1-methyl-piperidin-4-ylmethyl)-propion-amide | ¹H NMR (400 MHz, d6-DMSO): δ 8.62-8.50 (1H, m), 8.04-8.00 (1H, m), 7.96-7.78 (6H, m), 7.65-7.57 (2H, m), 7.07-7.02 (1H, m), 4.66-4.52 (1H, m), 3.28 (2H, d, J = 11.56 Hz), 3.24-3.14 (1H, m), 3.11-2.96 (1H, m), 2.76 (1H, d, J = 5.93 Hz), 2.71-2.62 (1H, m), 2.18-2.05 (3H, m), 1.82-1.65 (2H, m), 1.56-1.32 (3H, m), 1.06 (3H, t, J = 6.23 Hz), 0.93-0.85 (2H, m). | Rt = 3.19 min, m/z = 649.3 [M + H]+ |
| 8 | 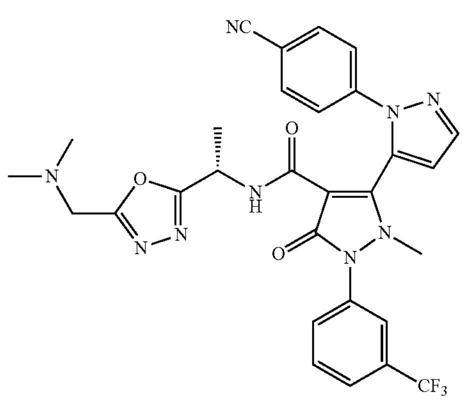 [SMILES: C[C@H](NC(=O)c1c(-c2ccnn2-c2ccc(C#N)cc2)n(C)n(-c2cccc(C(F)(F)F)c2)c1=O)c1nnc(CN(C)C)o1] | Intermediate H | ¹H NMR (400 MHz, d6-DMSO): δ 8.64 (1H, t, J = 8.16 Hz), 8.02 (1H, t, J = 7.69 Hz), 7.95 (1H, d, J = 8.79 Hz), 7.93-7.81 (5H, m), 7.61 (2H, q, J= 8.77 Hz), 7.03 (1H, t, J = 2.00 Hz), 5.04 (1H, q, J = 6.99 Hz), 3.65 (2H, d, J = 8.46 Hz), 3.30 (3H, d, J = 5.11 Hz), 2.17 (6H, d, J = 10.61 Hz), 1.38 (3H, d, J = 6.98 Hz), 1.31 (3H, d, J = 6.98 Hz). | Rt = 3.18 min, m/z = 606.2 [M + H]+ |

-continued

| Ex. | Structure | Amine | 1H NMR | LC-MS Method 3 |
|---|---|---|---|---|
| 9 | 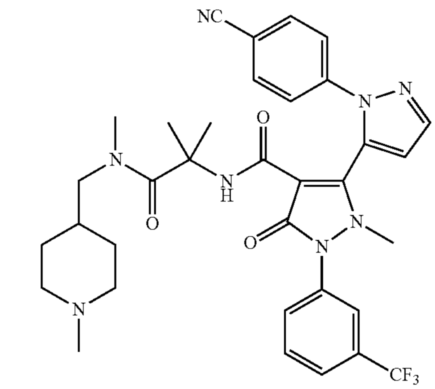 [SMILES: CN1CCC(CN(C)C(=O)C(C)(C)NC(=O)c2c(-c3ccnn3-c3ccc(C#N)cc3)n(C)n(-c3cccc(C(F)(F)F)c3)c2=O)CC1] | 2-Amino-2,N-dimethyl-N-(1-methyl-piperidin-4-ylmethyl)-propion-amide | ¹H NMR (400 MHz, d6-DMSO): δ 8.44 (1H, s), 8.02 (1H, d, J = 1.86 Hz), 7.96-7.83 (6H, m), 7.59 (2H, d, J = 8.75 Hz), 7.02 (1H, d, J = 1.85 Hz), 3.34 (2H, s), 2.73-2.60 (6H, m), 2.09 (4H, s), 1.79-1.60 (3H, m), 1.52-1.34 (3H, m), 1.20 (6H, d), 1.13-0.94 (2H, m). | Rt = 3.32 min, m/z = 663.3 [M + H]+ |
| 10 | 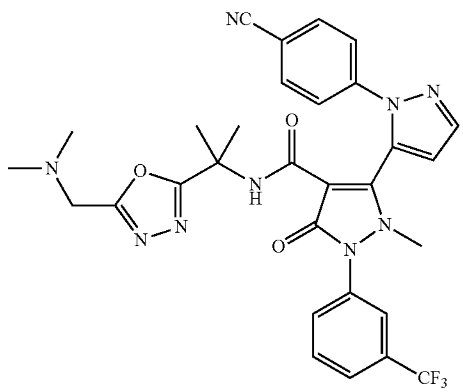 [SMILES: CN(C)Cc1nnc(C(C)(C)NC(=O)c2c(-c3ccnn3-c3ccc(C#N)cc3)n(C)n(-c3cccc(C(F)(F)F)c3)c2=O)o1] | Intermediate K | ¹H NMR (400 MHz, d6-DMSO): δ 8.64 (1H, s), 7.99 (1H, d, J = 1.86 Hz), 7.94-7.82 (6H, m), 7.55 (2H, d, J = 8.78 Hz), 7.00 (1H, d, J = 1.87 Hz), 6.80 (1H, s), 3.35 (2H, d, J = 1.5 Hz), 3.31 (3H, s), 2.06 (6H, s), 1.38 (6H, d, J = 8.29 Hz). | Rt = 3.32 min, m/z = 619.2 [M + H]+ |
| 11 | 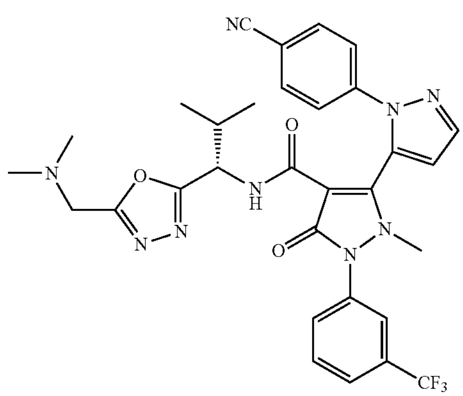 [SMILES: CC(C)[C@H](NC(=O)c1c(-c2ccnn2-c2ccc(C#N)cc2)n(C)n(-c2cccc(C(F)(F)F)c2)c1=O)c1nnc(CN(C)C)o1] | Intermediate J | ¹H NMR (400 MHz, d6-DMSO): δ 8.66 (1H, dd, J = 9.16 and 3.56 Hz), 8.02 (1H, t, J = 1.89 Hz), 7.96 (1H, s), 7.95-7.84 (4H, m), 7.81 (1H, d, J = 8.82 Hz), 7.52 (2H, dd, J = 18 and 8.81 Hz), 7.05 (1H, dd, J = 4.07 and 1.87 Hz), 6.89 (1H, d, J = 6.28 Hz), 4.74-4.62 (1H, m), 3.46 (1H, s), 3.40 (3H, s), 3.30 (1H, s), 2.12 (3H, s), 2.07 (3H, s), 0.79 (1H, t, J = 3.18 Hz), 0.76 (2H, dd, J = 16.4 and 6.80 Hz), 0.59 (4H, dd, J = 16.4 and 6.78 Hz). | Rt = 3.46 min, m/z = 633.2 [M + H]+ |
| 12 | 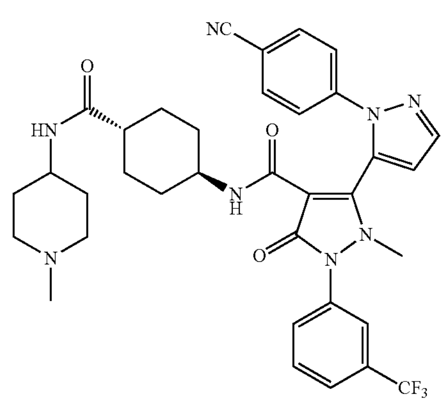 [SMILES: CN1CCC(NC(=O)[C@H]2CC[C@H](NC(=O)c3c(-c4ccnn4-c4ccc(C#N)cc4)n(C)n(-c4cccc(C(F)(F)F)c4)c3=O)CC2)CC1] | Intermediate O | ¹H NMR (400 MHz, d6-DMSO): δ 8.02 (1H, d, J = 1.86 Hz), 7.95-7.77 (7H, m), 7.61 (2H, d, J = 8.77 Hz), 7.56 (1H, d, J = 7.74 Hz), 7.03 (1H, d, J = 1.86 Hz), 3.49-3.36 (1H, m), 3.26 (3H, s), 2.71-2.60 (2H, m), 2.12 (3H, s), 1.98 (1H, dt, J = 3.34 and 11.98 Hz), 1.89 (2H, t, J = 11.09 Hz), 1.73 (1H, d, J = 12.39 Hz), 1.68-1.50 (5H, m), 1.42-1.20 (5H, m), 1.12-0.99 (1H, m), 0.99-0.78 (1H, m). | Rt = 3.29 min, m/z = 675.3 [M + H]+ |

| Ex. | Structure | Amine | 1H NMR | LC-MS Method 3 |
|---|---|---|---|---|
| 13 | 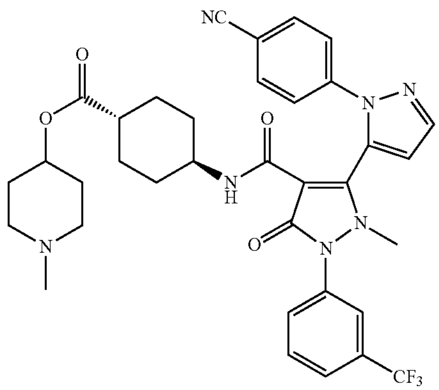 [SMILES: CN1CCC(OC(=O)[C@H]2CC[C@H](NC(=O)c3c(-c4ccnn4-c4ccc(C#N)cc4)n(C)n(-c4cccc(C(F)(F)F)c4)c3=O)CC2)CC1] | Intermediate P | $^1$H NMR (400 MHz, d6-DMSO): δ 8.02 (1H, d, J = 1.86 Hz), 7.98-7.77 (7H, m), 7.61 (2H, d, J = 8.82 Hz), 7.03 (1H, d, J = 1.87 Hz), 4.68-4.53 (1H, m), 3.41-3.27 (2H, m), 3.31 (3H, s), 2.49-2.41 (1H, m), 2.87-2.06 (3H, m), 2.13 (3H, s), 1.87-1.67 (5H, m), 1.60-1.46 (3H, m), 1.40-1.24 (2H, m), 1.20-1.07 (1H, m), 1.07-0.93 (1H, m). | Rt = 3.51 min, m/z = 676.2 [M + H]+ |
| 14 | 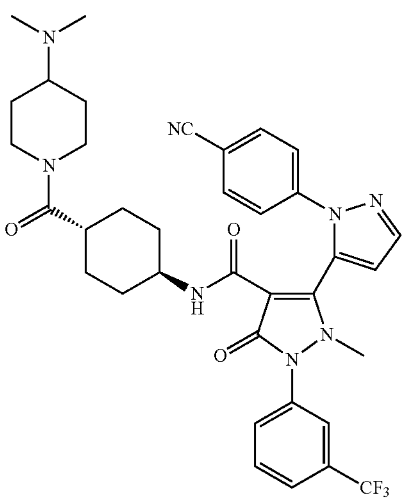 [SMILES: CN(C)C1CCN(C(=O)[C@H]2CC[C@H](NC(=O)c3c(-c4ccnn4-c4ccc(C#N)cc4)n(C)n(-c4cccc(C(F)(F)F)c4)c3=O)CC2)CC1] | Intermediate Q | $^1$H NMR (400 MHz, d6-DMSO): δ 8.02 (1H, d, J = 1.86 Hz), 7.98-7.77 (7H, m), 7.62 (2H, d, J = 8.79 Hz), 7.03 (1H, d, J = 1.87 Hz), 4.32 (1H, d, J = 12.31 Hz), 3.90 (1H, d, J = 13 Hz), 3.43-3.32 (2H, m), 3.26 (3H, s), 2.96 (1H, t, J = 12.6 Hz), 2.60-2.52 (1H, m), 2.33-2.20 (1H, tt, J = 3.56 and 10.87 Hz), 1.73 (3H, d, J = 9.11 Hz), 1.57 (3H, t, J = 14.78 Hz), 1.41-0.96 (6H, m). | Rt = 3.29 min, m/z = 689.2 [M + H]+ |
| 15 | 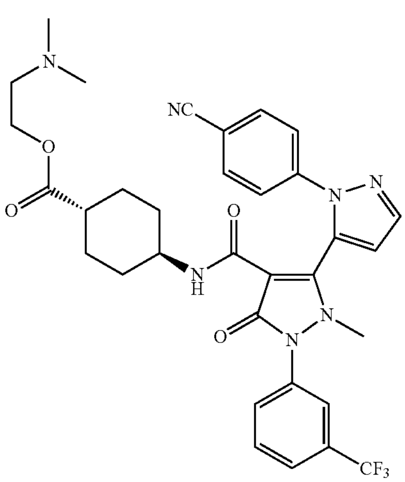 [SMILES: CN(C)CCOC(=O)[C@H]1CC[C@H](NC(=O)c2c(-c3ccnn3-c3ccc(C#N)cc3)n(C)n(-c3cccc(C(F)(F)F)c3)c2=O)CC1] | Intermediate R | $^1$H NMR (400 MHz, d6-DMSO): δ 8.02 (1H, d, J = 1.83 Hz), 7.98-7.77 (7H, m), 7.61 (2H, d, J = 8.59 Hz), 7.03 (1H, d, J = 1.83 Hz), 4.09 (2H, t, J = 5.64 Hz), 3.41-3.32 (3H, m), 3.27 (3H, s), 2.54 (12H, s), 2.30-2.23 (1H, m), 2.23 (6H, s), 1.89-1.77 (2H, m), 1.77-1.67 (1H, m), 1.59-1.48 (1H, m), 1.40-1.25 (2H, m), 1.20-1.07 (1H, m), 1.07-0.93 (1H, m). | Rt = 3.38 min, m/z = 650.3 [M + H]+ |

| Ex. | Structure | Amine | 1H NMR | LC-MS Method 3 |
|---|---|---|---|---|
| 16 | 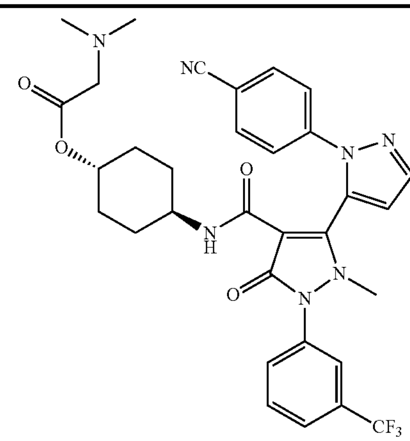 | Intermediate S | ¹H NMR (400 MHz, d6-DMSO): δ 8.02 (1H, d, J = 1.86 Hz), 8.00 (1H, d, J = 7.66 Hz), 7.96-7.79 (6H, m), 7.61 (2H, d, J = 8.73 Hz), 7.03 (1H, d, J = 1.85 Hz), 4.68-4.58 (1H, m), 3.49-3.38 (1H, m), 3.28 (6H, s), 3.10 (2H, s), 2.21 (6H, s), 1.87-1.65 (3H, m), 1.60-1.48 (1H, m), 1.44-1.30 (2H, m), 1.30-1.73 (1H, m), 1.73-1.02 (1H, m). | Rt = 3.41 min, m/z = 636.2 [M + H]+ |
| 17 | 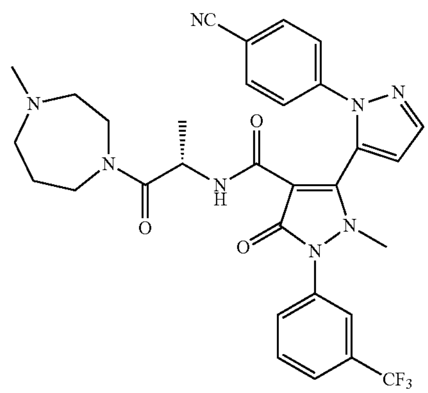 [SMILES: C[C@H](NC(=O)c1c(-c2ccnn2-c2ccc(C#N)cc2)n(C)n(-c2cccc(C(F)(F)F)c2)c1=O)C(=O)N1CCCN(C)CC1] | (S)-2-Amino-1-(4-methyl-[1,4]diazepan-1-yl)-propan-1-one | ¹H NMR (400 MHz, d6-DMSO): δ 8.60 (0.5H, q, J = 2.96 and 7.53 Hz)*, 8.54 (0.5H, q, J = 5.89 and 8.03 Hz), 8.02 (1H, t, J = 1.42 Hz), 7.96-7.80 (6H, m), 7.64-7.56 (2H, m), 7.06-7.03 (1H, m), 4.64-4.53 (1H, m), 3.64-3.39 (4H, m), 3.32-3.29 (3H, m), 2.55-2.29 (4H, m), 2.25 (1.5H, d, J = 8.17 Hz), 2.19 (1.5H, d, J = 6.28 Hz)*, 1.79-1.58 (2H, m), 1.07 (1.5H, q, J = 1.62 and 6.68 Hz)*, 0.90 (1.5H, q, J = 2.96 and 6.66 Hz)*. | Rt = 3.10 min, m/z = 621.2 [M + H]+ |

Example 18

4-{[2'-(4-Cyano-phenyl)-2-methyl-5-oxo-1-(3-trifluoromethyl-phenyl)-2,5-dihydro-1H,2'H-[3,3']bipyrazolyl-4-carbonyl]-amino}-1,1-dimethyl-piperidinium benzene sulphonate

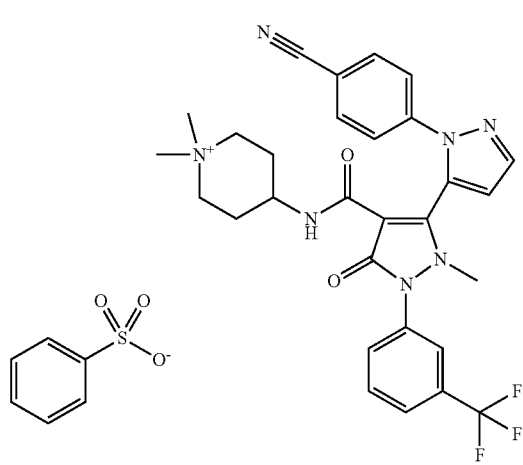 [SMILES: O=S(=O)([O-])c1ccccc1 ; Cn1c(-c2ccnn2-c2ccc(C#N)cc2)c(C(=O)NC2CC[N+](C)(C)CC2)c(=O)n1-c1cccc(C(F)(F)F)c1]

Example 2 (56 mg, 0.102 mmol) was stirred in DCM (4 ml) and 1 drop of methanol was added to give a clear solution. Methyl benzenesulphonate (17.5 mg, 0.102 mmol) was added and the mixture was stirred at RT overnight. The volume was reduced to ca. 1 ml by evaporation, THF (0.5 ml) added and the mixture heated at 50° C. for 4 h. After standing for a further 10 days at RT the mixture was partitioned between DCM and water and the separated aqueous phase was freeze dried to afford the title compound (36 mg, 49%).

LCMS (Method 3): Rt=3.22 min, m/z 564.3 [M]+

¹H NMR (400 MHz, d6-DMSO): δ 8.11 (1H, d, J=7.8 Hz), 8.03 (1H, d, J=1.9 Hz), 7.94-7.79 (6H, m), 7.63-7.57 (4H, m), 7.34-7.28 (3H, m), 7.05 (1H, d, J=1.9 Hz), 3.73-3.62 (1H, m), 3.43-3.25 (6H, m), 3.05 (6H, s), 1.92-1.52 (5H, m).

The following compounds were prepared by analogous procedures to that used in Examples 2 and 18. In the table below where rotameric signals have been identified in the NMR spectrum these have been labelled by *.

| Ex | Structure | Amine | Quat. reagent | 1H NMR | LC-MS Method 3 |
|---|---|---|---|---|---|
| 19 | 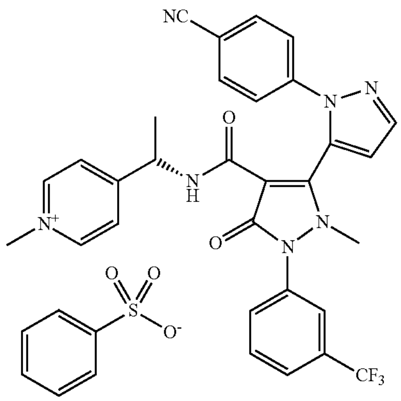 | (S)-1-Pyridin-4-yl-ethylamine | Methyl-benzene-sulphonate | ¹H NMR (400 MHz, d6-DMSO): δ 8.86 (1H, d J = 6.6 Hz), 8.81 (1H, d J = 6.6 Hz), 8.70-8.65 (1H, m), 8.02-7.98 (1H, m), 7.97-7.78 (8H, m), 7.63-7.56 (3H, m), 7.51 (1H, d J = 8.8 Hz), 7.34-7.26 (3H, m), 7.05 (0.5H*, d J = 1.8 Hz), 7.00 (0.5H*, d J = 1.9 Hz), 4.97-4.83 (1H, m), 4.34 (1.5H*, s), 3.34 (1.5H*, s), 3.34 (3H, s), 1.38-1.30 (3H, m). | Rt = 3.22 min, m/z = 564.3 [M]+ |
| 20 | 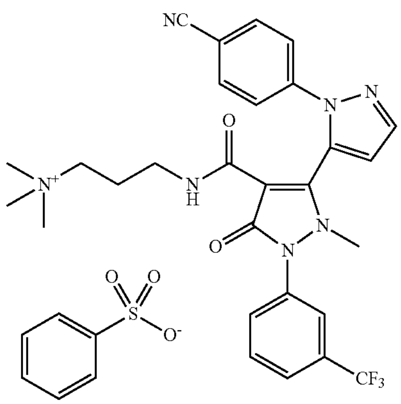 [SMILES: Cn1c(-c2ccnn2-c2ccc(C#N)cc2)c(C(=O)NCCC[N+](C)(C)C)c(=O)n1-c1cccc(C(F)(F)F)c1 ; O=S(=O)([O-])c1ccccc1] | N,N-Dimethyl-1,3-diamino-propane | Methyl-benzene-sulphonate | ¹H NMR (400 MHz, d6-DMSO): δ 8.21 (1H, t, J = 6.0 Hz), 8.03 (1H, d J = 1.9 Hz), 7.96-7.78 (6H, m), 7.63 (2H, d J = 8.8 Hz), 7.61-7.57 (2H, m), 7.34-7.26 (3H, m), 7.04 (1H, d J = 1.9 Hz), 3.29 (3H, s), 3.18-3.11 (2H, m), 3.10-3.02 (2H, m), 2.98 (9H, s), 1.74-1.63 (2H, m). | Rt = 3.19 min, m/z = 552.4 [M]+ |
| 21 | 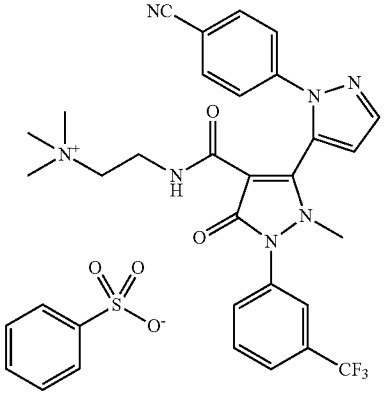 [SMILES: O=S(=O)([O-])c1ccccc1 ; Cn1c(-c2ccnn2-c2ccc(C#N)cc2)c(C(=O)NCC[N+](C)(C)C)c(=O)n1-c1cccc(C(F)(F)F)c1] | N,N-Dimethyl-1,2-diamino-ethane | Methyl-benzene-sulphonate | ¹H NMR (400 MHz, d6-DMSO): δ 8.35 (1H, t J = 6.0 Hz), 8.04 (1H, d J = 1.9 Hz), 7.97-7.79 (6H, m), 7.64 (2H, d J = 8.8 Hz), 7.61-7.57 (2H, m), 7.34-7.26 (3H, m), 7.05 (1H, d J = 1.9 Hz), 3.50-3.38 (2H, m), 3.32 (3H, m), 3.25-3.10 (2H, m), 2.99 (9H, s). | Rt = 3.18 min, m/z = 538.3 [M]+ |

-continued

| Ex | Structure | Amine | Quat. reagent | 1H NMR | LC-MS Method 3 |
|---|---|---|---|---|---|
| 22 | 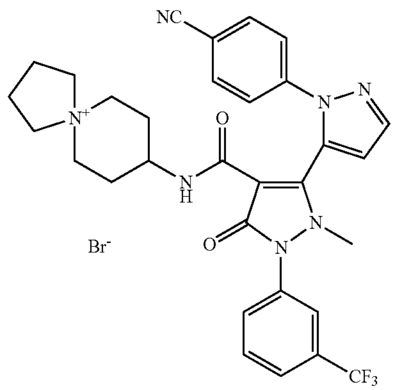 [SMILES: Cn1c(-c2ccnn2-c2ccc(C#N)cc2)c(C(=O)NC2CC[N+]3(CCCC3)CC2)c(=O)n1-c1cccc(C(F)(F)F)c1 ; [Br-]] | 4-Amino-piperidine-1-carboxylic acid tert-butyl ester | 1,4-dibromo-butane | ¹H NMR (400 MHz, CDCl₃): δ 8.44 (1H, d J = 6.9 Hz), 7.94 (1H, d J = 1.9 Hz), 7.78 (2H, d J = 8.8 Hz), 7.72-7.66 (2H, m), 7.62 (2H, d J = 8.8 Hz), 7.58-7.54 (1H, m), 7.45 (1H, s), 6.96 (1H, d J = 1.9 Hz), 4.12-4.02 (1H, m), 4.02-3.92 (1H, m), 3.91-3.59 (7H, m), 3.09 (3H, s), 2.34-1.84 (8H, m). | Rt = 3.26 min, m/z = 590.4 [M]+ |
| 23 | 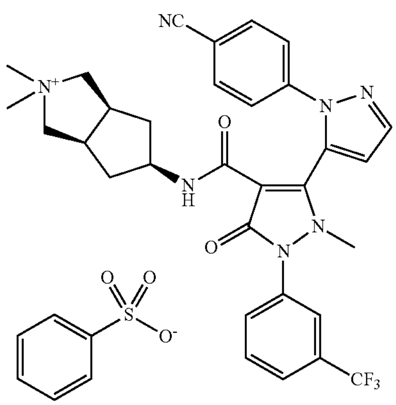 [SMILES: Cn1c(-c2ccnn2-c2ccc(C#N)cc2)c(C(=O)N[C@@H]2C[C@@H]3C[N+](C)(C)C[C@@H]3C2)c(=O)n1-c1cccc(C(F)(F)F)c1 ; O=S(=O)([O-])c1ccccc1] | (3aS,5R,6aR)-2-Methyl-octahydro-cyclopenta-[c]pyrrol-5-ylamine | Methyl-benzene-sul-phonate | ¹H NMR (400 MHz, CDCl₃): δ 8.49 (1H, d J = 6.7 Hz), 7.92 (1H, d J = 1.9 Hz), 7.91-7.86 (2H, m), 7.80 (2H, d J = 8.8 Hz), 7.72-7.67 (2H, m), 7.65 (2H, d J = 8.8 Hz), 7.55-7.51 (1H, m), 7.42 (1H, s), 7.36-7.29 (3H, m), 6.93 (1H, d J = 1.9 Hz), 4.37-4.28 (1H, m), 4.16-4.07 (1H, m), 4.06-3.98 (1H, m), 3.54-3.41 (5H, m), 3.37 (3H, s), 3.14-3.04 (5H, m), 2.16-2.06 (2H, m), 1.84-1.75 (1H, m), 1.69-1.60 (1H, m). | Rt = 3.25 min, m/z = 590.4 [M]+ |
| 24 | 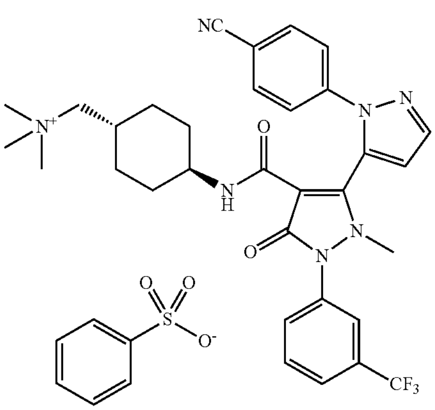 [SMILES: Cn1c(-c2ccnn2-c2ccc(C#N)cc2)c(C(=O)N[C@H]2CC[C@H](C[N+](C)(C)C)CC2)c(=O)n1-c1cccc(C(F)(F)F)c1 ; O=S(=O)([O-])c1ccccc1] | Trans-4-dimethyl-amino-methyl-cyclohexyl-amine | Methyl-benzene-sul-phonate | ¹H NMR (400 MHz, CDCl₃): δ 8.11 (1H, d J = 7.8 Hz), 8.00 (1H, d J = 1.9 Hz), 7.88-7.83 (2H, m), 7.75 (2H, d J = 8.8 Hz), 7.71-7.64 (2H, m), 7.61 (2H, d J = 8.8 Hz), 7.48-7.43 (1H, m), 7.40 (1H, s), 7.38-7.30 (3H, m), 6.90 (1H, d J = 1.9 Hz), 3.68-3.56 (1H, m), 3.38-3.22 (11H, m), 3.01 (3H, s), 2.00-1.92 (1H, m), 1.92-1.82 (3H, m), 1.80-1.70 (1H, m), 1.32-1.10 (4H, m). | Rt = 3.36 min, m/z = 606.4 [M]+ |

-continued

| Ex | Structure | Amine | Quat. reagent | 1H NMR | LC-MS Method 3 |
|---|---|---|---|---|---|
| 25 | 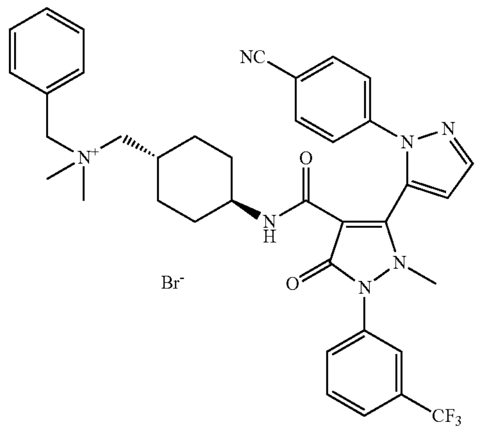 [SMILES: Cn1c(-c2ccnn2-c2ccc(C#N)cc2)c(C(=O)N[C@H]2CC[C@H](C[N+](C)(C)Cc3ccccc3)CC2)c(=O)n1-c1cccc(C(F)(F)F)c1 ; [Br-]] | Trans-4-dimethyl-amino-methyl-cyclohexyl-amine | Benzyl bromide | $^1$H NMR (400 MHz, CDCl$_3$): δ 8.12 (1H, d J = 7.8 Hz), 7.92 (1H, d J = 1.9 Hz), 7.75 (2H, d J = 8.8 Hz), 7.70-7.63 (4H, m), 7.61 (2H, d J = 8.8 Hz), 7.51-7.38 (5H, m), 6.91 (1H, d J = 1.9 Hz), 5.06 (1H, d J = 12.7 Hz), 5.04 (1H, d J = 12.7 Hz), 3.70-3.55 (2H, m), 3.43 (1H, dd J = 13.2 and 3.5 Hz), 3.28 (3H, s), 3.26 (3H, s), 3.02 (3H, s), 2.04-1.84 (5H, m), 1.40-1.19 (4H, m). | Rt = 3.79 min, m/z = 682.4 [M]+ |
| 26 | 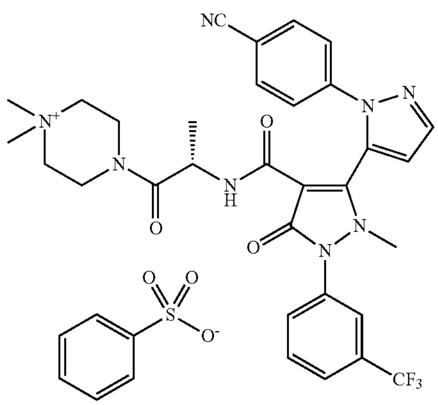 [SMILES: C[C@H](NC(=O)c1c(-c2ccnn2-c2ccc(C#N)cc2)n(C)n(-c2cccc(C(F)(F)F)c2)c1=O)C(=O)N1CC[N+](C)(C)CC1 ; O=S(=O)([O-])c1ccccc1] | (S)-2-Amino-1-(4-methyl-piperazin-1-yl)-propan-1-one | Methyl-benzene-sul-phonate | $^1$H NMR (400 MHz, CDCl$_3$): δ 9.20-8.75 (1H*, m), 7.93-7.85 (1H*, m), 7.80-7.36 (10 H, m), 7.35-7.25 (3H, m), 7.00-6.86 (1H*, m), 4.96-4.64 (1H*, m), 4.08-3.92 (1H, m) 3.84-3.14 (13 H, m), 3.10-2.94 (3H*, m), 1.38-1.06 (3H, m). | Rt = 3.22 min, m/z = 621.4 [M]+ |
| 27 | 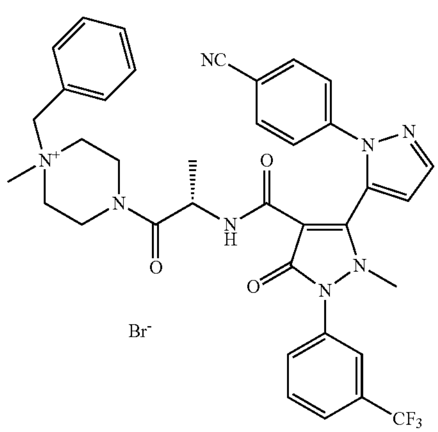 [SMILES: C[C@H](NC(=O)c1c(-c2ccnn2-c2ccc(C#N)cc2)n(C)n(-c2cccc(C(F)(F)F)c2)c1=O)C(=O)N1CC[N+](C)(Cc2ccccc2)CC1 ; [Br-]] | (S)-2-Amino-1-(4-methyl-piperazin-1-yl)-propan-1-one | Benzyl bromide | $^1$H NMR (400 MHz, CDCl$_3$): δ 8.96-8.68 (1H*, m), 7.92-7.30 (14H, m), 7.17-6.88 (1H*, m), 5.40-4.70 (3H*, m), 4.54-3.22 (11H, m), 3.21-2.90 (3H*, m), 1.38-1.12 (3H, m). | Rt = 3.52 min, m/z = 697.4 [M]+ |

-continued

| Ex | Structure | Amine | Quat. reagent | 1H NMR | LC-MS Method 3 |
|---|---|---|---|---|---|
| 28 | 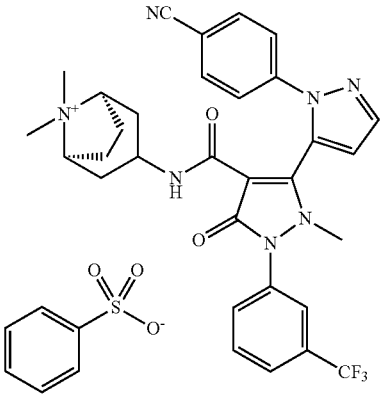 [SMILES: O=S(=O)([O-])c1ccccc1 ; Cn1c(-c2ccnn2-c2ccc(C#N)cc2)c(C(=O)NC2C[C@H]3CC[C@@H](C2)[N+]3(C)C)c(=O)n1-c1cccc(C(F)(F)F)c1] | (1S,3S,5R)-8-Methyl-8-aza-bicyclo[3.2.1]oct-3-ylamine | Methyl-benzene-sul-phonate | $^1$H NMR (400 MHz, d6-DMSO): δ 8.16 (1H, d J = 7.5 Hz), 8.04-8.02 (1H, m), 7.96-7.78 (6H, m), 7.64-7.56 (4H, m), 7.34-7.25 (3H, m), 7.06-7.00 (1H*, 2x d J = 1.9 Hz), 3.96-3.85 (1H, m), 3.80 (2H, s), 3.32 (3H, s), 3.28-3.23 (3H*, 2xs), 2.96 (3H, s), 2.32-1.86 (6H, m), 1.62-1.52 (2H, m). | Rt = 3.24 min, m/z = 590.4 [M]+ |
| 29 | 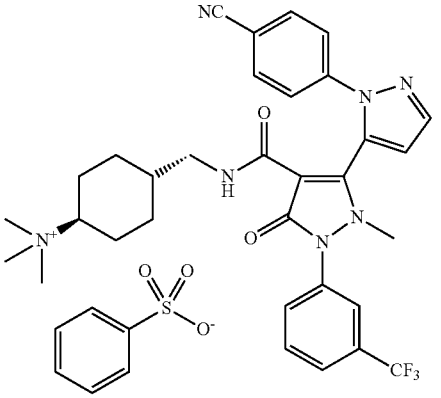 | (Trans-4-amino-methyl-cyclo-hexyl)-dimethyl-amine | Methyl-benzene-sul-phonate | $^1$H NMR (400 MHz, d6-DMSO): δ 8.13 (1H, t J = 6.1 Hz), 8.03 (1H, d J = 1.8 Hz), 7.96-7.81 (6H, m), 7.64-7.56 (4H, m), 7.34-7.26 (3H, m), 7.04 (1H, d J = 1.8 Hz), 3.34 (3H, s), 3.27-3.16 (1H, m), 3.04-2.97 (10 H, m), 2.82-2.74 (1H, m), 2.14-2.05 (2H, m), 1.66-1.58 (1H, m), 1.57-1.48 (1H, m), 1.43-1.30 (2H, m), 1.28-1.15 (1H, m), 0.88-0.72 (2H, m). | Rt = 3.28 min, m/z = 606.4 [M]+ |
| 30 | 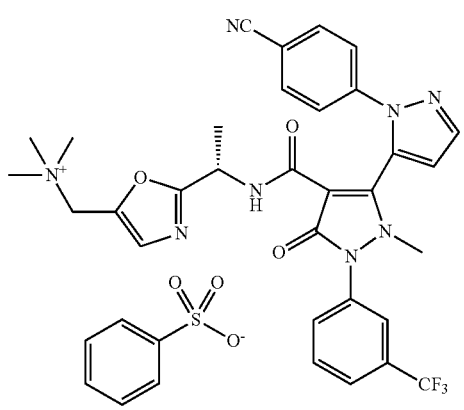 [SMILES: C[C@H](NC(=O)c1c(-c2ccnn2-c2ccc(C#N)cc2)n(C)n(-c2cccc(C(F)(F)F)c2)c1=O)c1ncc(C[N+](C)(C)C)o1 ; O=S(=O)([O-])c1ccccc1] | See Ex 5 | Methyl-benzene-sul-phonate | $^1$H NMR (400 MHz, CDCl$_3$): δ 8.97-8.78 (1H*, 2xd J = 7.5 and 7.3 Hz), 7.92-7.84 (3H, m), 7.78-7.72 (2H, m), 7.70-7.61 (2H, m), 7.60-7.55 (2H, m), 7.53-7.30 (6H, m), 7.01-6.91 (1H*, 2xd J = 1.9 Hz), 5.19-5.09 (1H, m), 4.99-4.83 (2H, m), 3.26, (9H, s), 3.09-3.01 (3H*, 2xs), 1.57-1.50 (3H, m). | Rt = 3.24 min, m/z = 619.4 [M]+ |

-continued

| Ex | Structure | Amine | Quat. reagent | 1H NMR | LC-MS Method 3 |
|---|---|---|---|---|---|
| 31 | 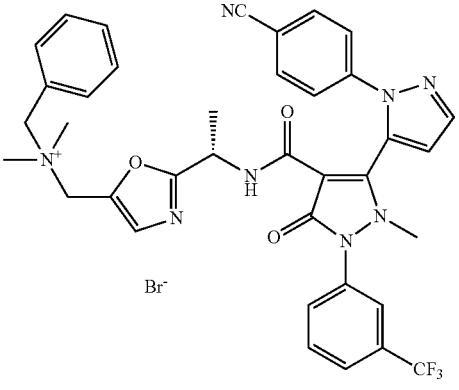 [SMILES: C[C@H](NC(=O)c1c(-c2ccnn2-c2ccc(C#N)cc2)n(C)n(-c2cccc(C(F)(F)F)c2)c1=O)c1ncc(C[N+](C)(C)Cc2ccccc2)o1 ; [Br-]] | See Ex 5 | Benzyl bromide | ¹H NMR (400 MHz, CDCl₃): δ 9.00-8.79 (1H*, 2xd J = 7.5 and 7.3 Hz), 7.92-7.80 (1H*, 2xd J = 1.9 Hz), 7.78-7.72 (2H, m), 7.72-7.60 (4H, m), 7.59-7.38 (8H, m), 6.99-6.93 (1H*, d J = 1.9 Hz), 5.28-4.96 (5H, m), 3.24-3.14 (6H, m), 3.12-3.00 (3H*, 2xs), 1.61-1.55 (3H*, 2xd J = 7.0 Hz). | Rt = 3.06 min, m/z = 695.4 [M]+ |
| 32 | 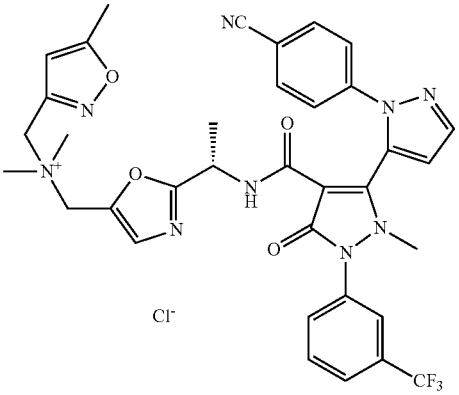 [SMILES: Cc1cc(C[N+](C)(C)Cc2cnc([C@H](C)NC(=O)c3c(-c4ccnn4-c4ccc(C#N)cc4)n(C)n(-c4cccc(C(F)(F)F)c4)c3=O)o2)no1 ; [Cl-]] | See Ex 5 | 3-Chloromethyl-5-methyl-isoxazole | ¹H NMR (400 MHz, CDCl₃): δ 8.97-8.79 (1H*, 2xd J = 7.5 and 7.2 Hz), 7.94-7.90 (1H*, 2x d J = 1.9 Hz), 7.80-7.74 (2H, m), 7.73-7.65 (2H, m), 7.58 (2H, d J = 8.6 Hz), 7.56-7.42 (3H, m), 7.02-6.94 (1H*, 2xd J = 1.9 Hz), 6.68 (1H, s), 5.24-5.02 (5H, m), 3.38-3.30 (6H*, 2xs), 3.12-3.03 (3H*, 2xs), 2.50-2.45 (3H*, 2xs), 1.61-1.53 (3H, m). | Rt = 3.47 min, m/z = 700.4 [M]+ |
| 33 | 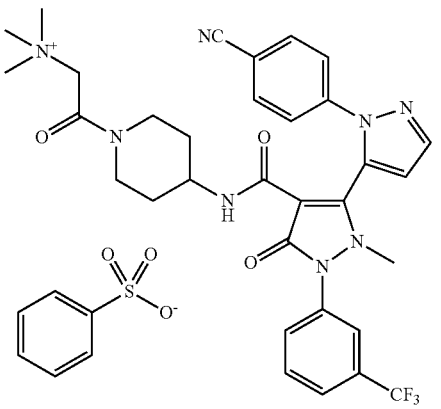 [SMILES: Cn1c(-c2ccnn2-c2ccc(C#N)cc2)c(C(=O)NC2CCN(C(=O)C[N+](C)(C)C)CC2)c(=O)n1-c1cccc(C(F)(F)F)c1 ; O=S(=O)([O-])c1ccccc1] | See Ex 6 | Methylbenzene-sulphonate | ¹H NMR (400 MHz, CDCl₃): δ 8.32-8.26 (1H, m), 7.93 (1H, d J = 1.9 Hz), 7.87-7.73 (4H, m), 7.70-7.64 (2H, m), 7.63-7.58 (2H, m), 7.48-7.30 (5H, m), 6.93-6.90 (1H, m), 5.00-4.74 (2H, m), 4.20-4.10 (1H, m), 4.00-3.89 (1H, m), 3.86-3.68 (1H, m), 3.50 (9H, s), 3.22-3.11 (1H, m), 3.04-2.90 (4H, m), 1.96-1.79 (2H, m), 1.58-1.33 (2H, m). | Rt = 3.28 min, m/z = 635.4 [M]+ |

| Ex | Structure | Amine | Quat. reagent | 1H NMR | LC-MS Method 3 |
|---|---|---|---|---|---|
| 34 | 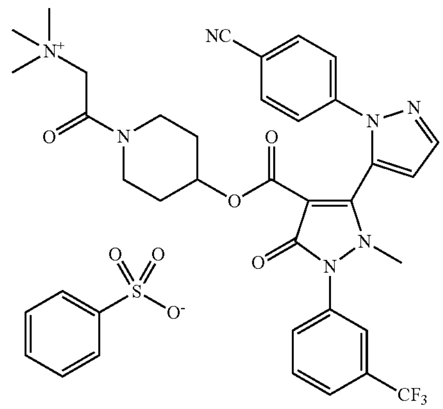 [SMILES: Cn1c(-c2ccnn2-c2ccc(C#N)cc2)c(C(=O)OC2CCN(C(=O)C[N+](C)(C)C)CC2)c(=O)n1-c1cccc(C(F)(F)F)c1 ; O=S(=O)([O-])c1ccccc1] | 2-Dimethyl-amino-1-(4-hydroxy-piperidin-1-yl)-ethanone | Methyl-benzene-sulphonate | $^1$H NMR (400 MHz, d6-DMSO): δ 8.07 (1H, t, J = 1.5 Hz) 8.02-7.96 (2H, m), 7.89-7.80 (2H, m), 7.78-7.73 (2H, m), 7.72-7.65 (2H, m), 7.61-7.57 (2H, m), 7.35-7.27 (3H, m), 7.13-7.10 (1H, m), 4.76 (1H, br. s), 4.45-4.38 (2H, m), 3.57-3.41 (1H, br. m), 3.38-3.13 (3H, m), 3.25 (3H, s), 3.21 (9H, s), 1.76-1.10 (4H, m). | Rt = 3.25 min, m/z = 636.5 [M]+ |
| 35 | 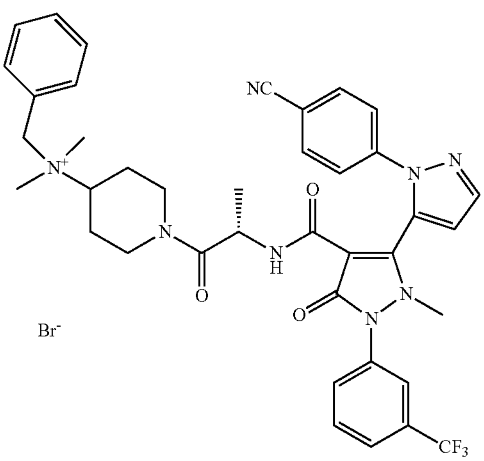 [SMILES: C[C@H](NC(=O)c1c(-c2ccnn2-c2ccc(C#N)cc2)n(C)n(-c2cccc(C(F)(F)F)c2)c1=O)C(=O)N1CCC([N+](C)(C)Cc2ccccc2)CC1 ; [Br-]] | (S)-2-Amino-1-(4-dimethyl-amino-piperidin-1-yl)-propan-1-one | Benzyl bromide | $^1$H NMR (400 MHz, d6-DMSO): δ 8.54 (1H, d, J = 7.9 Hz), 7.96 (1H, s), 7.89 (2H, d, J = 8.5 Hz), 7.86-7.80 (2H, m), 7.80-7.70 (2H, m), 7.62 (2H, d, J = 8.5 Hz), 7.59-7.46 (5H, m), 6.99 (1H, d, J = 1.9 Hz), 4.70 (1H, quin, J = 7.2 Hz), 4.52-4.44 (2H, m), 3.26 (1H, br s), 3.30-3.15 (3H, m), 2.95-2.81 (6H, m), 2.35-2.20 (2H, m), 1.83-1.61 (2H, m), 1.22-0.97 (total 3H, 2 x m,). Some signals obscured by water. | Rt = 3.49 min, m/z = 725.4 [M]+ |
| 36 | 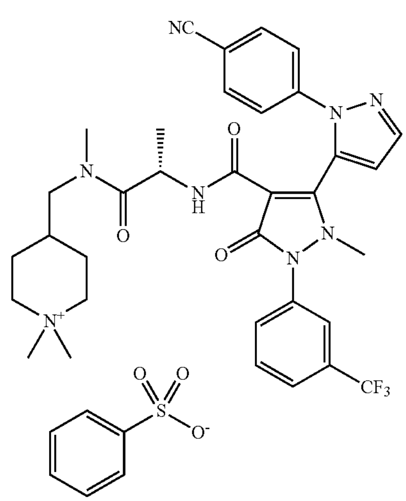 [SMILES: C[C@H](NC(=O)c1c(-c2ccnn2-c2ccc(C#N)cc2)n(C)n(-c2cccc(C(F)(F)F)c2)c1=O)C(=O)N(C)CC1CC[N+](C)(C)CC1 ; O=S(=O)([O-])c1ccccc1] | See Ex 7 | Methyl-benzene-sulphonate | $^1$H NMR (400 MHz, d6-DMSO): δ 8.62 (0.2H, d, J = 7.07 Hz)*, 8.56 (0.6H, q, J = 7.20 Hz)*, 8.49 (0.2H, d, J = 8.20 Hz)*, 8.03 (qH, d, J = 1.84 Hz), 7.96-7.77 (6H, m), 7.64-7.55 (4H, m), 7.35-7.25 (3H, m), 7.07-7.01 (1H, m), 3.47-3.34 (5H, m), 3.30-3.08 (5H, m), 3.08-2.96 (5H, m), 2.77 (1H, d, J = 8.64 Hz), 1.91-1.71 (2H, m), 1.71-1.45 (4H, m), 1.09 (3H, t, J = 6.70 Hz), 0.92 (1H, d, J = 6.75 Hz). | Rt = 3.21 min, m/z = 663.4 [M]+ |

-continued

| Ex | Structure | Amine | Quat. reagent | 1H NMR | LC-MS Method 3 |
|---|---|---|---|---|---|
| 37 | (structure) | See Ex 8 | Methyl-benzene-sulphonate | ¹H NMR (400 MHz, d6-DMSO): δ 8.72 (1H, m), 8.03 (1H, dd, J = 1.87 and 5.44 Hz), 7.98-7.80 (6H, m), 7.65-7.56 (4H, m), 7.35-7.25 (3H, m), 7.04 (1H, dd, J = 1.87 and 4.17 Hz), 5.07 (1H, m), 4.92 (2H, d, J = 8.02 Hz), 3.34 (3H, s), 3.14 (9H, d, J = 4.10 Hz), 1.36 (3H, m). | Rt = 3.18 min, m/z = 620.2 [M]+ |
| 38 | (structure) | Intermediate T | Methyl-benzene-sulphonate | ¹H NMR (400 MHz, d6-DMSO): δ 8.53-8.45 (2H, m), 8.03 (1H, dd, J = 4.78 and 1.86 Hz), 7.96-7.80 (6H, m), 7.64-7.56 (2H, m), 7.04 (1H, dd, J = 3.54 and 1.87 Hz), 4.20 (1H, t, J = 7.05 Hz), 4.05-3.90 (2H, m), 3.37 (6H, s), 3.31 (2H, d, J = 10.94 Hz), 3.08 (2H, d, J = 6.73 Hz), 2.99 (3H, d, J = 10.63 Hz), 1.91-1.52 (5H, m), 1.20 (1.5H, d, J = 7.14 Hz), 1.13 (1.5H, d, J = 7.14 Hz). | Rt = 3.64 min, m/z = 650.3 [M]+ |
| 39 | (structure) | Intermediate U | Methyl-benzene-sulphonate | ¹H NMR (400 MHz, d6-DMSO): δ 8.08 (1H, d, J = 7.48 Hz), 8.03 (1H, d, J = 1.86 Hz), 7.95-7.78 (6H, m), 7.65-7.55 (4H, m), 7.35-7.25 (3H, m), 7.05 (1H, d, J = J = 1.86 Hz), 4.07-3.92 (1H, m), 3.67 (2H, br s), 3.45 (1H, br s), 3.42 (3H, br s), 3.21-3.05 (4H, m), 3.02 (3H, s), 2.93-2.76 (2H, m), 2.03-1.84 (2H, m), 1.84-1.61 (4H, m), 1.61-1.41 (1H, m), 1.37-1.10 (3H, m), 1.06-0.92 (1H, m). | Rt = 3.20 min, m/z = 675.4 [M]+ |

| Ex | Structure | Amine | Quat. reagent | 1H NMR | LC-MS Method 3 |
|---|---|---|---|---|---|
| 40 | 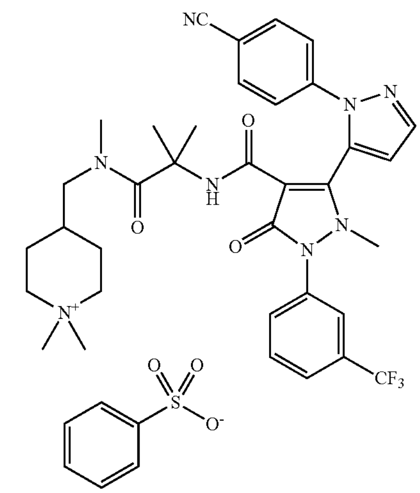 [SMILES: CN(CC1CC[N+](C)(C)CC1)C(=O)C(C)(C)NC(=O)c1c(-c2ccnn2-c2ccc(C#N)cc2)n(C)n(-c2cccc(C(F)(F)F)c2)c1=O ; O=S(=O)([O-])c1ccccc1] | See Ex 9 | Methyl-benzene-sulphonate | ¹H NMR (400 MHz, d6-DMSO): δ 8.44 (1H, s), 8.05 (1H, d, J = 1.85 Hz), 7.97-7.83 (6H, m), 7.64-7.56 (4H, m), 7.34-7.25 (3H, m), 7.03 (1H, d, J = 1.84 Hz), 3.34 (2H, s), 3.23-3.10 (2H, m), 3.07 (3H, s), 2.97 (3H, s), 2.83 (1H, br s), 2.75 (3H, s), 1.69-1.38 (6H, m), 1.27 (3H, s), 1.14 (3H, s). | Rt = 3.32 min, m/z = 677.3 [M]+ |
| 41 | 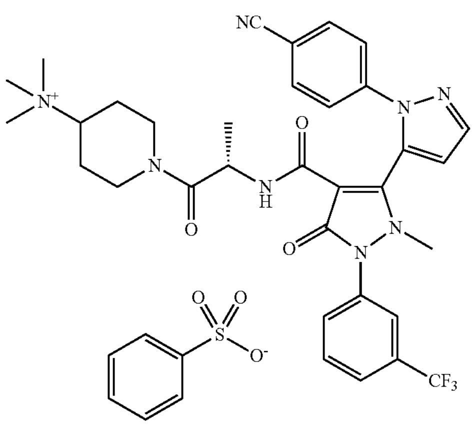 [SMILES: C[C@H](NC(=O)c1c(-c2ccnn2-c2ccc(C#N)cc2)n(C)n(-c2cccc(C(F)(F)F)c2)c1=O)C(=O)N1CCC([N+](C)(C)C)CC1 ; O=S(=O)([O-])c1ccccc1] | (S)-2-Amino-1-(4-dimethyl-amino-piperidin-1-yl)-propan-1-one | Methyl-benzene-sulphonate | ¹H NMR (400 MHz, d6-DMSO): δ 8.71-8.49 (3H, m), 8.03-8.01 (1H, d), 7.96-7.77 (6H, m), 7.65-7.56 (4H, m), 7.36-7.25 (3H, m), 7.08-7.03 (1H, d), 4.68-4.57 (1H, t), 4.56-4.43 (1H, m), 3.99-3.87 (1H, m), 3.57-3.47 (1H, d), 3.35-3.27 (1H, m), 3.05-2.91 (9H, m), 2.18-2.01 (3H, m), 1.65-1.37 (3H, m), 1.12-1.06 (1H, d), 0.95-0.86 (2H, q) | Rt = 3.33 min, m/z = 649.3 [M]+ |
| 42 | 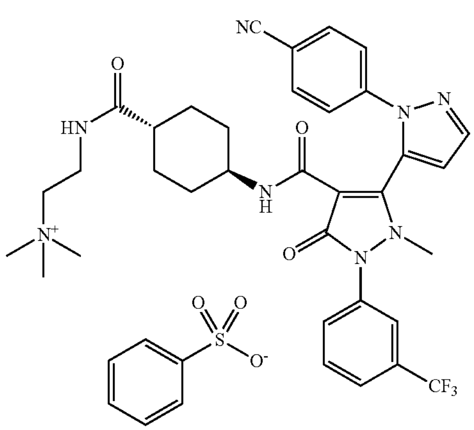 [SMILES: Cn1c(-c2ccnn2-c2ccc(C#N)cc2)c(C(=O)N[C@H]2CC[C@H](C(=O)NCC[N+](C)(C)C)CC2)c(=O)n1-c1cccc(C(F)(F)F)c1 ; O=S(=O)([O-])c1ccccc1] | Intermediate V | Methyl-benzene-sulphonate | ¹H NMR (400 MHz, d6-DMSO): δ 8.07-8.01 (2H, d + t), 7.95-7.78 (8H, m), 7.64-7.57 (4H, m), 7.34-7.27 (3H, m), 7.04-7.02 (1H, d), 3.47-3.40 (2H, q), 3.36-3.26 (2H, q), 3.10-3.03 (9H, s), 2.77-2.69 (1H, br.s), 2.08-1.98 (1H, d. of t.), 1.77-1.65 (3H, m), 1.59-1.52 (1H, br.d), 1.39-1.26 (2H, m), 1.14-1.02 (1H, br.q), 1.02-0.90 (1H, br.q) | Rt = 3.38 min, m/z = 663.3 [M]+ |

-continued

| Ex | Structure | Amine | Quat. reagent | 1H NMR | LC-MS Method 3 |
|---|---|---|---|---|---|
| 43 | 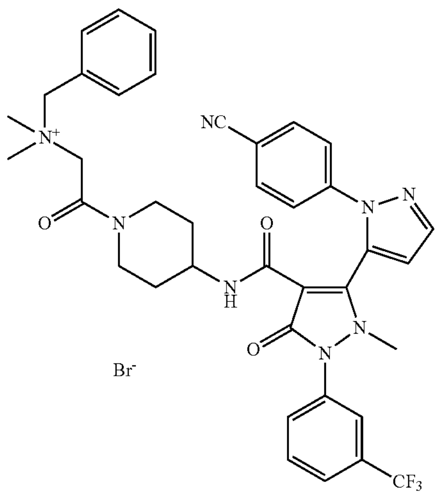 [SMILES: Cn1c(-c2ccnn2-c2ccc(C#N)cc2)c(C(=O)NC2CCN(C(=O)C[N+](C)(C)Cc3ccccc3)CC2)c(=O)n1-c1cccc(C(F)(F)F)c1 ; [Br-]] | 1-(4-Amino-piperidin-1-yl)-2-dimethyl-amino-ethanone | Benzyl bromide | ¹H NMR (400 MHz, d6-DMSO): δ 8.15-8.08 (1H, q), 8.05-8.02 (1H, d), 7.96-7.81 (5H, m), 7.65-7.59 (2H, d. of d), 7.58-7.42 (5H, m), 7.06-7.04 (1H, t), 4.84-4.71 (2H, q), 4.33-4.18 (2H, m), 4.13-3.98 (1H, br.q), 3.75-3.64 (1H, br.s), 3.53-3.44 (1H, br.d), 3.21-3.03 (6H, m), 2.99-2.86 (1H, br.q), 1.78-1.64 (1H, br.q), 1.60-1.48 (1H, br.t), 1.31-1.19 (1H, br.s), 1.18-1.06 (1H, br.s) | Rt = 3.70 min, m/z = 711.2 [M]+ |
| 44 | 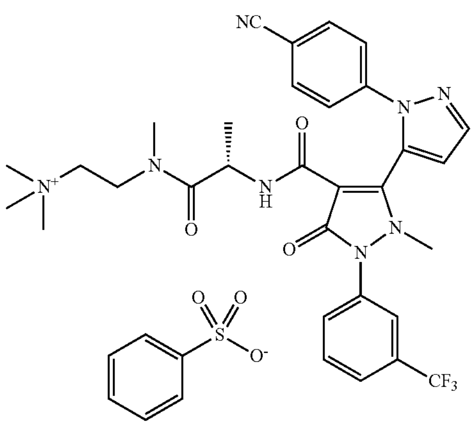 [SMILES: C[C@H](NC(=O)c1c(-c2ccnn2-c2ccc(C#N)cc2)n(C)n(-c2cccc(C(F)(F)F)c2)c1=O)C(=O)N(C)CC[N+](C)(C)C ; O=S(=O)([O-])c1ccccc1] | (S)-2-Amino-N-(2-dimethyl-amino-ethyl)-N-methyl-propion-amide | Methyl-benzene-sul-phonate | ¹H NMR (400 MHz, d6-DMSO): δ 8.59-8.52 (1H, m), 8.04-8.02 (1H, m), 7.95-7.78 (6H, m), 7.64-7.57 (4H, m), 7.34-7.27 (3H, m), 7.05-7.02 (1H, m), 4.63-4.54 (1H, m), 3.68-3.63 (1H, br.t), 3.42-3.35 (2H, m), 3.29-3.27 (1H, s), 3.10-3.01 (9H, d), 3.00-2.96 (1H, s), 2.95-2.90 (1H, s), 1.11-1.07 (1H, d), 0.95-0.90 (1H, d) | Rt = 3.24 min, m/z = 623.2 [M]+ |
| 45 | 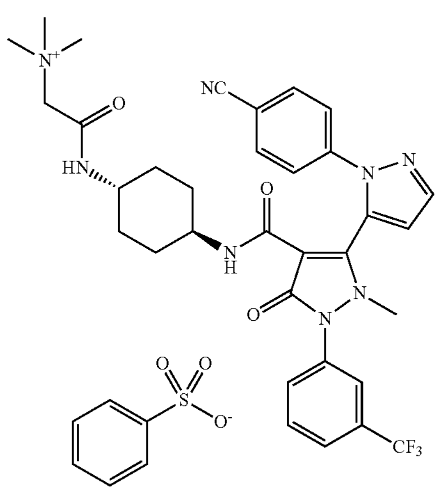 [SMILES: Cn1c(-c2ccnn2-c2ccc(C#N)cc2)c(C(=O)N[C@H]2CC[C@H](NC(=O)C[N+](C)(C)C)CC2)c(=O)n1-c1cccc(C(F)(F)F)c1 ; O=S(=O)([O-])c1ccccc1] | N-(Trans-4-amino-cyclohexyl)-2-dimethyl-amino-acetamide | Methyl-benzene-sul-phonate | ¹H NMR (400 MHz, d6-DMSO): δ 8.40-8.36 (1H, d) 8.03-8.01 (1H, d), 7.98-7.79 (7H, m), 7.64-7.57 (4H, m), 7.34-7.28 (3H, m), 7.04-7.02 (1H, d), 4.01-3.98 (2H, s), 3.58-3.48 (1H, br. s), 3.43-3.33 (1H, br. s), 3.20-3.15 (9H, s), 1.78-1.69 (3H, br), 1.55-1.49 (1H, br. d), 1.25-1.11 (3H, m.), 1.11-0.98 (2H, q) | Rt = 3.39 min. m/z = 649.3 [M]+ |

-continued

| Ex | Structure | Amine | Quat. reagent | 1H NMR | LC-MS Method 3 |
|---|---|---|---|---|---|
| 46 | 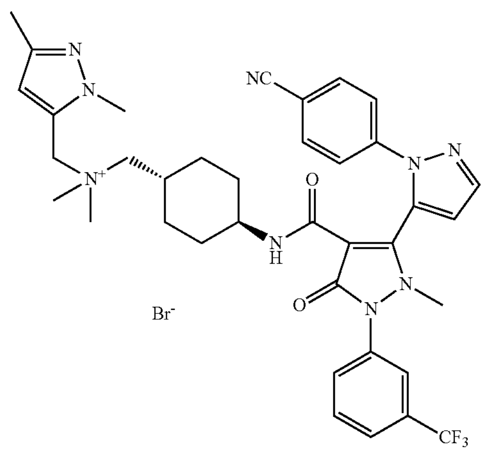 [SMILES: Cc1cc(C[N+](C)(C)C[C@H]2CC[C@H](NC(=O)c3c(-c4ccnn4-c4ccc(C#N)cc4)n(C)n(-c4cccc(C(F)(F)F)c4)c3=O)CC2)n(C)n1 ; [Br-]] | Trans-4-dimethyl-amino-methyl-cyclohexyl-amine | 5-Bromo-methyl-1,3-dimethyl-1H-pyrazole | $^1$H NMR (400 MHz, CDCl$_3$): δ 8.12 (1H, d, J = 7.8 Hz), 7.92 (1H, d, J = 1.9 Hz), 7.78-7.72 (2H, m), 7.71-7.63 (2H, d, m), 7.63-7.56 (2H, m), 7.47-7.42 (1H, m), 7.42-7.37 (1H, m), 6.90 (1H, d, J = 1.9 Hz), 6.26 (1H, s), 5.32-5.20 (2H, m), 4.13 (3H, s), 3.75-3.60 (2H, m), 3.54-3.51 (1H, m), 3.31 (6H, d, J = 9.8 Hz), 3.03 (3H, s), 2.25 (3H, s), 2.06-1.85 (4H, m), 1.43 (1H, s), 1.37-1.18 (4H, m). | Rt = 3.57 min, m/z = 700 [M]+ |
| 47 | 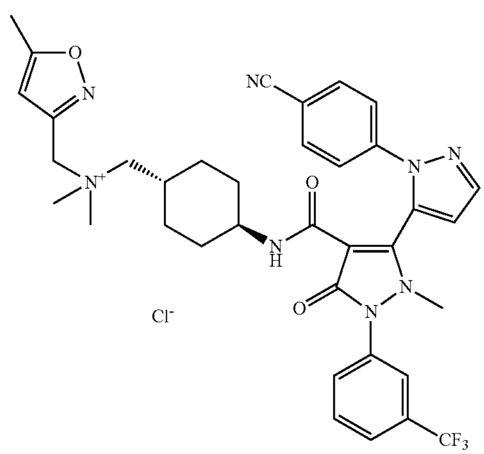 [SMILES: Cc1cc(C[N+](C)(C)C[C@H]2CC[C@H](NC(=O)c3c(-c4ccnn4-c4ccc(C#N)cc4)n(C)n(-c4cccc(C(F)(F)F)c4)c3=O)CC2)no1 ; [Cl-]] | Trans-4-dimethyl-amino-methyl-cyclohexyl-amine | 3-Chloro-methyl-5-methyl-isoxazole | $^1$H NMR (400 MHz, CDCl$_3$): δ 8.15 (1H, d, J = 7.3 Hz), 7.92 (1H, d, J = 1.9 Hz), 7.79-7.73 (2H, m), 7.71-7.64 (2H, m), 7.63-7.58 (2H, m), 7.48-7.43 (1H, m), 7.41-7.38 (1H, m), 6.90 (1H, d, J = 1.9 Hz), 6.80 (1H, s), 5.30-5.20 (2H, m), 3.78-3.72 (2H, m), 3.71-6.63 (1H, m), 3.58-3.50 (1H, m), 3.44-3.37 (6H, m), 3.03 (3H, s), 2.47 (3H, s), 2.08-1.88 (4H, m), 1.88-1.82 (2H, m), 1.40-1.20 (4H, m). | Rt = 3.68 min, m/z = 687 [M]+ |
| 48 | 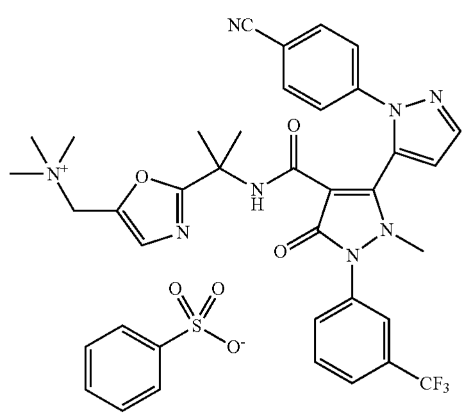 [SMILES: Cn1c(-c2ccnn2-c2ccc(C#N)cc2)c(C(=O)NC(C)(C)c2ncc(C[N+](C)(C)C)o2)c(=O)n1-c1cccc(C(F)(F)F)c1 ; O=S(=O)([O-])c1ccccc1] | See Ex 10 | Methyl-benzene-sul-phonate | $^1$H NMR (400 MHz, d6-DMSO): δ 8.65 (1H, s), 7.98 (1H, d, J = 1.85 Hz), 7.96-7.82 (6H, m), 7.62-7.56 (2H, m), 7.53 (2H, d, J = 8.73 Hz), 7.34-7.27 (4H, m), 7.00 (1H, d, J = 1.85 Hz), 4.62 (2H, s), 3.36 (3H, s), 2.93 (9H, s), 1.41 (6H, d). | Rt = 3.35 min, m/z = 633.2 [M]+ |

-continued

| Ex | Structure | Amine | Quat. reagent | 1H NMR | LC-MS Method 3 |
|---|---|---|---|---|---|
| 49 | 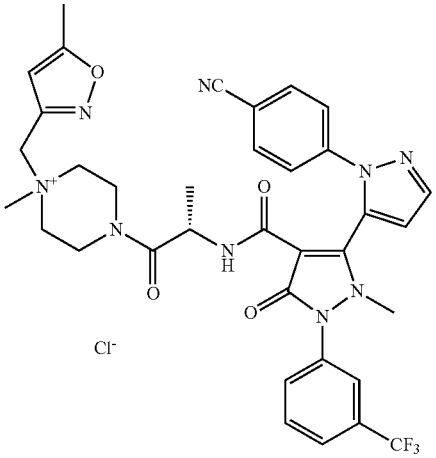 [SMILES: Cc1cc(C[N+]2(C)CCN(C(=O)[C@H](C)NC(=O)c3c(-c4ccnn4-c4ccc(C#N)cc4)n(C)n(-c4cccc(C(F)(F)F)c4)c3=O)CC2)no1 ; [Cl-]] | (S)-2-Amino-1-(4-methyl-piperazin-1-yl)-propan-1-one | 3-Chloro-methyl-5-methyl-isoxazole | ¹H NMR (400 MHz, DMSO-d₆): δ 8.61-8.52 (1H, m), 7.98 (1H, d, J = 1.9 Hz), 7.93-7.70 (6H, m), 7.65-7.58 (2H, m), 6.99 (1H, s), 6.53-6.47 (1H, m), 4.86-4.68 (3H, m), 4.08-3.93 (2H, m), 3.79-3.63 (2H, m), 3.56-3.43 (4H, m), 3.25 (1H, s), 3.21-3.11 (4H, m), 3.11-3.03 (3H, m) 1.28-1.34 (2H, m), 1.07-1.99 (2H, m). | Rt = 3.48 min, m/z = 702 [M]+ |
| 50 | 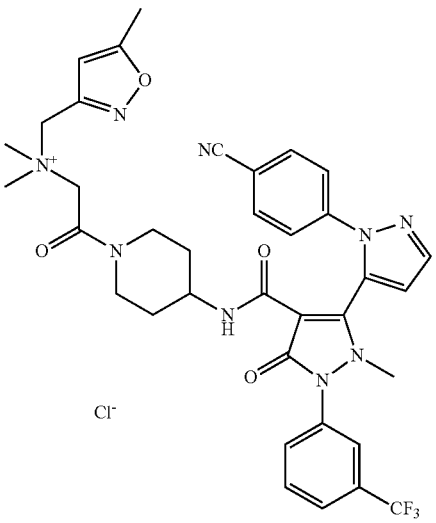 [SMILES: Cc1cc(C[N+](C)(C)CC(=O)N2CCC(NC(=O)c3c(-c4ccnn4-c4ccc(C#N)cc4)n(C)n(-c4cccc(C(F)(F)F)c4)c3=O)CC2)no1 ; [Cl-]] | 1-(4-Amino-piperidin-1-yl)-2-dimethyl-amino-ethanone | 3-Chloro-methyl-5-methyl-isoxazole | ¹H NMR (400 MHz, DMSO-d₆): δ 8.14-8.07 (1H, d. of d), 8.04-8.01 (1H, d), 7.95-7.80 (6H, m), 7.64-7.59 (2H, q), 7.06-7.0291H, m), 6.45-6.42 (1H, d), 4.94-4.83 (2H, q), 4.47-4.36 (2H, q), 4.10-3.95 (1H, m), 3.75-3.64 (1H, br. s), 3.52-3.43 (1H, br.d), 3.28-3.22 (6H, m), 3.14-3.03 (1H, br.t), 2.96-2.84 (1H, br.q), 2.46-2.43 (1H, s), 1.76-1.66 (1H, br.s), 1.59-1.49 (1H, br.t), 1.31-1.15 (2H, m) 1.13-1.02 (1H, br.q). | Rt = 3.51 min, m/z = 716.3 [M]+ |
| 51 | 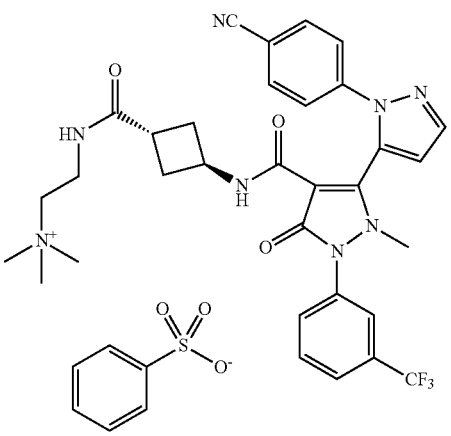 [SMILES: Cn1c(-c2ccnn2-c2ccc(C#N)cc2)c(C(=O)N[C@H]2C[C@H](C(=O)NCC[N+](C)(C)C)C2)c(=O)n1-c1cccc(C(F)(F)F)c1 ; O=S(=O)([O-])c1ccccc1] | Intermediate W | Methyl-benzene-sul-phonate | ¹H NMR (400 MHz, DMSO-d₆): δ 8.26 (1H, d, J = 7.8 Hz), 8.08 (1H, t, 5.6 Hz), 8.02 (1H, d, J = 1.8 Hz), 7.95-7.77 (6H, m), 7.64-7.56 (4H, m), 7.35-7.25 (3H, m), 7.03 1H, d, 1.9 Hz), 4.22 (1H, sext, J = 7.9 Hz), 3.50-3.42 (2H, m), 3.37-3.30 (2H, m), 3.28 (3H, s), 3.08 (9H, s), 2.86-2.77 (1H, m), 2.30-2.17 (2H, m), 2.01 (1H, q, J = 9.5 Hz), 1.91 (1H, q, J = 9.5 Hz). | Rt = 3.28 min, m/z = 635 [M]+ |

| Ex | Structure | Amine | Quat. reagent | 1H NMR | LC-MS Method 3 |
|---|---|---|---|---|---|
| 52 | 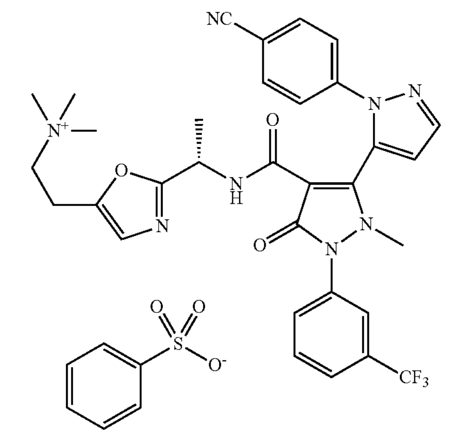 [SMILES: C[C@H](NC(=O)c1c(-c2ccnn2-c2ccc(C#N)cc2)n(C)n(-c2cccc(C(F)(F)F)c2)c1=O)c1ncc(CC[N+](C)(C)C)o1 ; O=S(=O)([O-])c1ccccc1] | Intermediate L | Methyl-benzene-sul-phonate | ¹H NMR (400 MHz, d6-DMSO): δ 8.60 (1H, t, J = 8.82 Hz), 8.03 (1H, dd, J = 1.89 and 2.68 Hz), 7.97-7.73 (6H, m), 7.66-7.55 (4H, m), 7.35-7.25 (4H, m), 7.05 (1H, dd, J = 1.87 and 5.44 Hz), 6.92-6.88 (1H, m), 4.87 (1H, td, J = 2.76 and 7.5 Hz), 3.65-3.51 (2H, m), 3.35 (1.5H, s), 3.30 (1.5H, s), 3.24-3.13 (2H, m), 3.09 (9H, d, J = 14.9 Hz), 1.32 (1.5H, d, J = 6.9 Hz), 1.19 (1.5H, d, J = 6.9 Hz). | Rt = 3.25 min, m/z = 633.2 [M]+ |
| 53 | 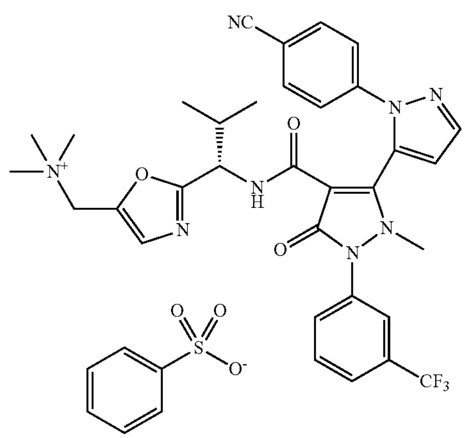 [SMILES: CC(C)[C@H](NC(=O)c1c(-c2ccnn2-c2ccc(C#N)cc2)n(C)n(-c2cccc(C(F)(F)F)c2)c1=O)c1ncc(C[N+](C)(C)C)o1 ; O=S(=O)([O-])c1ccccc1] | Intermediate X | Methyl-benzene-sul-phonate | ¹H NMR (400 MHz, d6-DMSO): δ 8.74 (1H, dd, J = 4.12 and 8.93 Hz), 8.03 (1H, t, J = 1.82 Hz), 7.98-7.80 (6H, m), 7.62-7.57 (3H, m), 7.55 (1H, d, J = 8.79 Hz), 7.35-7.25 (3H, m), 7.05 (1H, dd, J = 1.87 and 3.70 Hz), 4.77-4.69 (2H, m), 4.65 (1H, s), 3.42 (3H, s), 3.08-3.01 (4H, m), 2.99 (5H, s), 0.80 (2H, q, J = 6.84 and 9.66 Hz), 0.64 (4H, dd, J = 6.79 and 21.85 Hz). | Rt = 3.46 min, m/z = 647.2 [M]+ |
| 54 | 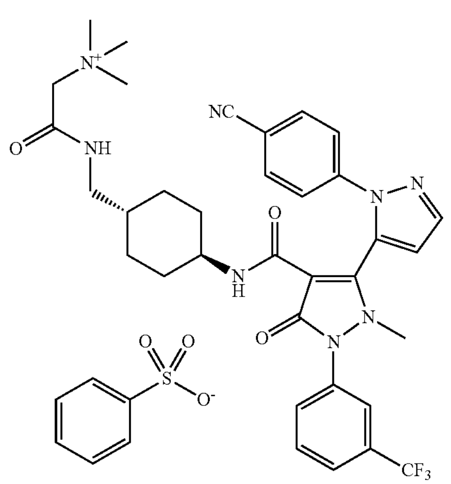 [SMILES: Cn1c(-c2ccnn2-c2ccc(C#N)cc2)c(C(=O)N[C@H]2CC[C@H](CNC(=O)C[N+](C)(C)C)CC2)c(=O)n1-c1cccc(C(F)(F)F)c1 ; O=S(=O)([O-])c1ccccc1] | N-(4-Amino-cyclohexyl-methyl)-2-dimethyl-amino-acetamide | Methyl-benzene-sul-phonate | ¹H NMR (400 MHz, d6-DMSO): δ 8.44-8.39 (1H, m), 8.03-8.01 (1H, d), 7.94-7.78 (6H, m), 7.63-7.56 (4H, m), 7.34-7.27 (3H, m), 7.04-7.02 (1H, d), 4.07-4.04 (1H, s), 3.30-3.27 (3H, s), 3.22-3.17 (9H, s), 2.98-2.93 (2H, t), 1.74-1.67 (1H, bd.d), 1.67-1.59 (2H, m), 1.54-1.47 (1H, bd.s), 1.37-1.26 (1H, bd.s), 1.10-0.98 (1H, m), 0.98-0.85 (3H, m). | Rt = 3.43 min, m/z = 663.3 [M]+ |

-continued

| Ex | Structure | Amine | Quat. reagent | 1H NMR | LC-MS Method 3 |
|---|---|---|---|---|---|
| 55 | 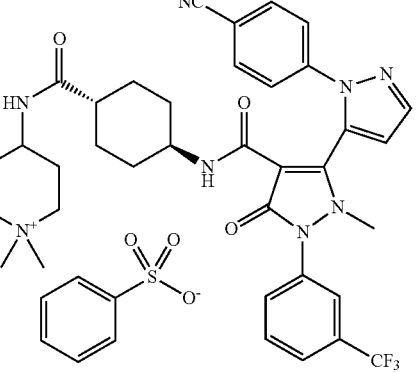 | Intermediate Y | Methyl-benzene-sulphonate | $^1$H NMR (400 MHz, DMSO-d$_6$): δ 8.26 (1H, d, J = 7.8 Hz), 8.02 (1H, d, J = 1.8 Hz), 7.95-7.77 (7H, m), 7.64-7.56 (4H, m), 7.34-7.25 (3H, m), 7.03 (1H, d, 1.9 Hz), 4.22 (1H, sext, J = 7.9 Hz), 3.86-3.75 (1H, m), 3.43-3.36 (4H, m), 3.28 (3H, s), 3.08 (3H, s), 3.03 (3H, s), 2.84-2.75 (1H, m), 2.28-2.15 (2H, m), 2.05-1.84 (4H, m), 1.81-1.68 (2H, m). | Rt = 3.29 min, m/z = 661 [M]+ |
| 56 | 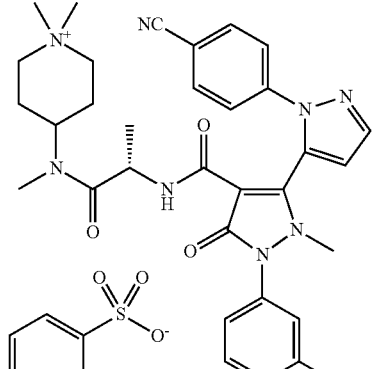 | (S)-2-Amino-N-methyl-N-(1-methyl-piperidin-4-yl)-propion-amide | Methyl-benzene-sulphonate | $^1$H NMR (400 MHz, d6-DMSO): δ 8.60-8.46 (1H, d), 7.98-7.95 (1H, d), 7.91-7.71 (6H, m) 7.64-7.57 (4H, m), 7.30-7.22 (3H, m), 7.00-6.96 (1H, d), 4.73-4.62 (1H, bd.s), 3.53-3.43 (4H, bd.s), 2.87-2.76 (3H, s), 2.25-2.073H, bd.s), 1.70-1.58 (2H, m), 1.16-1.11 (1H, m), 1.01-0.95 (1H, m). | Rt = 3.23 min, m/z = 649.3 [M]+ |
| 57 | 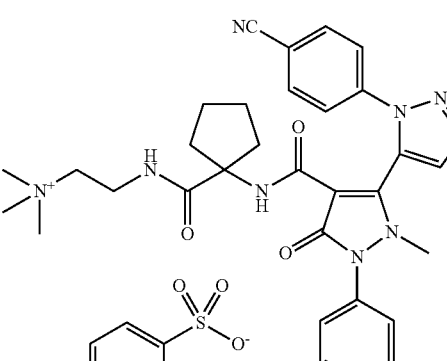 | 1-Amino-cyclo-pentane-carboxylic acid (2-dimethyl-amino-ethyl)-amide | Methyl-benzene-sulphonate | $^1$H NMR (400 MHz, d6-DMSO): δ 8.41-8.37 (1H, s), 7.99-7.96 (1H, d), 7.90-7.74 (6H, m), 7.65-7.56 (6H, m), 7.30-7.23 (6H, m), 7.00-6.99 (1H, d), 3.43-3.33 (6H, m), 3.29-3.25 (5H, s), 3.11-3.09 (3H, s), 3.09-3.07 (3H, s), 3.01-2.98 (9H, s), 2.18-2.05 (2H, m), 2.04-1.86 (3H, m), 1.69-1.54 (7H, m), 1.48-1.35 (2H, m). | Rt = 3.39 min, m/z = 649.3 [M]+ |

| Ex | Structure | Amine | Quat. reagent | 1H NMR | LC-MS Method 3 |
|---|---|---|---|---|---|
| 58 | 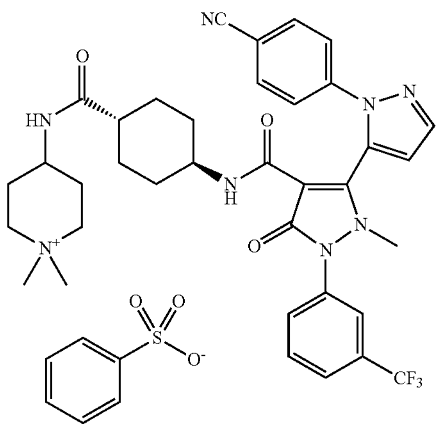 [SMILES: Cn1c(-c2ccnn2-c2ccc(C#N)cc2)c(C(=O)N[C@H]2CC[C@H](C(=O)NC3CC[N+](C)(C)CC3)CC2)c(=O)n1-c1cccc(C(F)(F)F)c1 ; O=S(=O)([O-])c1ccccc1] | See Ex 12 | Methyl-benzene-sulphonate | ¹H NMR (400 MHz, d6-DMSO): δ 8.02 (1H, d, J = 1.86 Hz), 7.95-7.76 (5H, m), 7.72 (1H, d, J = 7.43 Hz), 7.64-7.56 (3H, m), 7.35-7.25 (3H, m), 7.03 (1H, d, J = 1.86 Hz), 3.84-3.72 (1H, m), 3.47-3.32 (5H, m), 3.28 (3H, s), 3.05 (6H, d, J = 17.04 Hz), 2.07-1.95 (1H, m), 1.95-1.83 (2H, m), 1.82-1.62 (5H, m), 1.61-1.50 (1H, m), 1.41-1.24 (2H, m), 1.15-1.01 (1H, m), 1.01-0.87 (1H, m). | Rt = 3.33 min, m/z = 689.5 [M]+ |
| 59 | 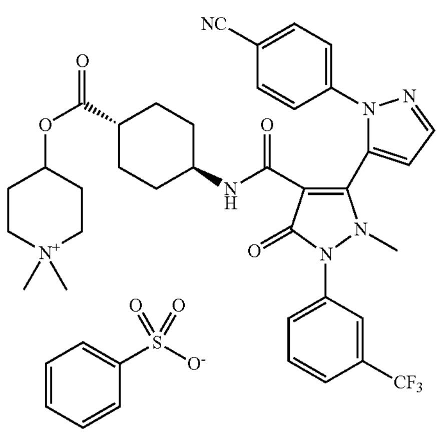 [SMILES: Cn1c(-c2ccnn2-c2ccc(C#N)cc2)c(C(=O)N[C@H]2CC[C@H](C(=O)OC3CC[N+](C)(C)CC3)CC2)c(=O)n1-c1cccc(C(F)(F)F)c1 ; O=S(=O)([O-])c1ccccc1] | See Ex 13 | Methyl-benzene-sulphonate | ¹H NMR (400 MHz, d6-DMSO): δ 8.02 (1H, d, J = 1.87 Hz), 7.99-7.78 (7H, m), 7.64-7.56 (4H, m), 7.35-7.26 (3H, m), 7.04 (1H, d, J = 1.86 Hz), 4.89-4.81 (1H, m), 3.39 (5H, t, J = 5.23 Hz), 3.29 (3H, s), 3.10 (6H, d), 2.26 (1H, dt, J = 3.48 and 11.63 Hz), 2.19-2.04 (2H, m), 1.95-1.81 (4H, m), 1.79-1.68 (1H, m), 1.59-1.49 (1H, m), 1.43-1.27 (2H, m), 1.19-1.06 (1H, m), 1.06-0.93 (1H, m). | Rt = 3.51 min, m/z = 690.3 [M]+ |
| 60 | 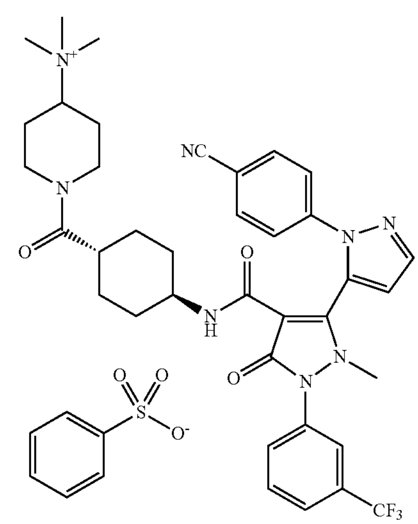 [SMILES: Cn1c(-c2ccnn2-c2ccc(C#N)cc2)c(C(=O)N[C@H]2CC[C@H](C(=O)N3CCC([N+](C)(C)C)CC3)CC2)c(=O)n1-c1cccc(C(F)(F)F)c1 ; O=S(=O)([O-])c1ccccc1] | See Ex 14 | Methyl-benzene-sulphonate | ¹H NMR (400 MHz, d6-DMSO): δ 8.02 (1H, d, J = 1.84 Hz), 7.97-7.78 (7H, m), 7.66-7.55 (4H, m), 7.35-7.25 (3H, m), 7.03 (1H, d, J = 1.85 Hz), 4.56 (1H, d, J = 12.35 Hz), 4.11 (1H, d, J = 12.57 Hz), 3.53 (1H, t, J = 11.87 Hz), 3.42-3.33 (1H, m), 3.28 (3H, s), 3.00 (9H, s), 2.61-2.52 (1H, m), 2.22-2.05 (3H, m), 1.79-1.69 (1H, m), 1.68-1.24 (7H, m), 1.24-1.12 (1H, m), 1.12-0.98 (1H, m). | Rt = 3.30 min, m/z = 703.3 [M]+ |

-continued

| Ex | Structure | Amine | Quat. reagent | 1H NMR | LC-MS Method 3 |
|---|---|---|---|---|---|
| 61 | 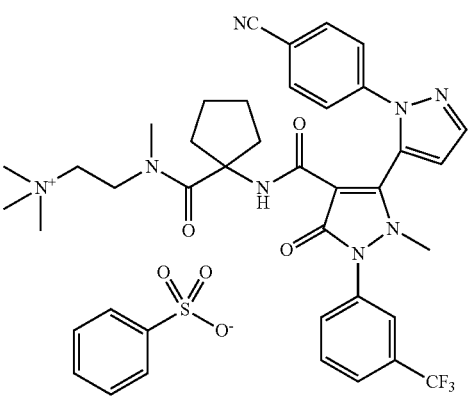 [SMILES: CN(CC[N+](C)(C)C)C(=O)C1(NC(=O)c2c(-c3ccnn3-c3ccc(C#N)cc3)n(C)n(-c3cccc(C(F)(F)F)c3)c2=O)CCCC1 ; O=S(=O)([O-])c1ccccc1] | 1-Amino-cyclo-pentane-carboxylic acid (2-dimethyl-amino-ethyl)-methyl-amide | Methyl-benzene-sul-phonate | $^1$H NMR (400 MHz, d6-DMSO): δ 8.51-8.43 (1H, bd.s), 8.43-8.38 (1H, s), 8.05-8.03 (1H, d), 7.98-7.84 (6H, m), 7.61-7.55 (2H, d), 7.09-7.06 (1H, d) 3.65-3.58 (2H, t), 3.41-3.33 1H, s) 3.07-2.99 (9H, s), 2.78-2.72 (3H, s), 2.05-1.92 (2H, m), 1.74-1.65 (1H, m), 1.59-1.45 (3H, m), 1.41-1.30 (2H, m). | Rt = 3.42 min, m/z = 663.3 [M]+ |
| 62 | 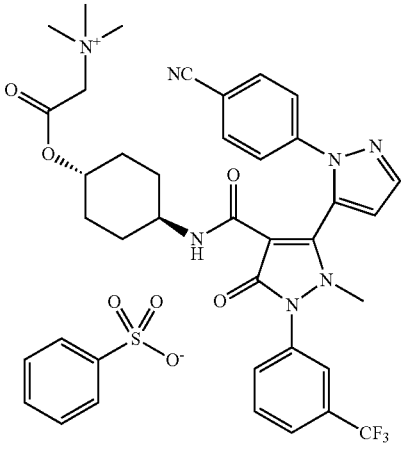 [SMILES: Cn1c(-c2ccnn2-c2ccc(C#N)cc2)c(C(=O)N[C@H]2CC[C@H](OC(=O)C[N+](C)(C)C)CC2)c(=O)n1-c1cccc(C(F)(F)F)c1 ; O=S(=O)([O-])c1ccccc1] | See Ex 16 | Methyl-benzene-sul-phonate | $^1$H NMR (400 MHz, d6-DMSO): δ 8.05-7.99 (2H, m), 7.95-7.79 (6H, m), 7.64-7.56 (4H, m), 7.34-7.25 (3H, m), 7.04 (1H, d, J = 1.86 Hz), 4.83-4.74 (1H, m), 4.40 (2H, s), 3.53-3.40 (1H, m), 3.31 (3H, s), 3.20 (9H, s), 1.91-1.68 (3H, m), 1.60-1.50 (1H, m), 1.50-1.36 (2H, m), 1.35-1.21 (1H, m), 1.20-1.08 (1H, m). | Rt = 3.38 min, m/z = 650.2 [M]+ |
| 63 | 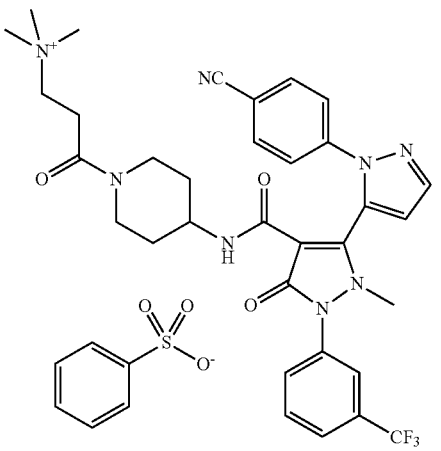 [SMILES: Cn1c(-c2ccnn2-c2ccc(C#N)cc2)c(C(=O)NC2CCN(C(=O)CC[N+](C)(C)C)CC2)c(=O)n1-c1cccc(C(F)(F)F)c1 ; O=S(=O)([O-])c1ccccc1] | 1-(4-Amino-piperidin-1-yl)-3-dimethyl-amino-propan-1-one | Methyl-benzene-sul-phonate | $^1$H NMR (400 MHz, d6-DMSO): δ 8.12-8.06 (1H, t), 8.04-8.02 (1H, d), 7.95-7.80 (6H, m), 7.64-7.56 (4H, m), 7.34-7.26 (3H, m), 7.06-7.03 (1H, t), 4.02-3.91 (1H, bd.t), 3.71-3.63 (1H, m), 3.55-3.48 (2H, t), 3.08-3.01 (9H, s), 2.90-2.80 (3H, q), 1.76-1.62 (1H, m), 1.60-1.44 (1H, bd.t), 1.39-0.93 (3H, m) | Rt = 3.13 min, m/z = 649.3 [M]+ |

| Ex | Structure | Amine | Quat. reagent | 1H NMR | LC-MS Method 3 |
|---|---|---|---|---|---|
| 64 | 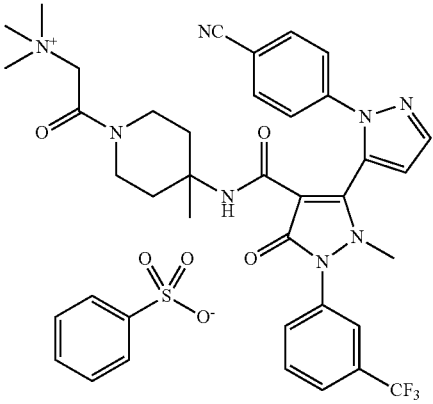 [SMILES: Cn1c(-c2ccnn2-c2ccc(C#N)cc2)c(C(=O)NC2(C)CCN(C(=O)C[N+](C)(C)C)CC2)c(=O)n1-c1cccc(C(F)(F)F)c1 ; O=S(=O)([O-])c1ccccc1] | Intermediate Z | Methyl-benzene-sul-phonate | ¹H NMR (400 MHz, d6-DMSO): δ 8.12-8.09 (1H, s), 8.04-8.02 (1H, d), 7.94-7.84 (6H, m), 7.62-7.56 (4H, m), 7.33-7.27 (3H, m), 7.08-7.06 (1H, d), 4.53-4.28 (3H, m), 3.99-3.89 (1H, bd.t), 3.41-3.37 (3H, s), 3.23-3.17 (9H, d), 3.03-2.93 (1H, bd.t), 2.79-2.68 (1H, bd.q), 1.92-1.82 (1H, bd.t), 1.44-1.18 (3H, m), 1.08-1.04 (3H, s) | Rt = 3.29 min, m/z = 649.2 [M]+ |
| 65 | 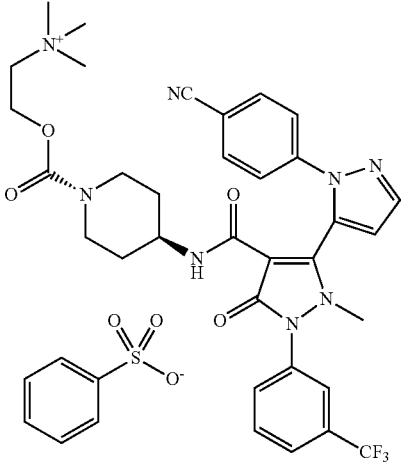 | See Ex 15 | Methyl-benzene-sul-phonate | ¹H NMR (400 MHz, d6-DMSO): δ 8.02 (1H, d, J = 1.86 Hz), 7.99-7.77 (7H, m), 7.64-7.55 (4H, m), 7.35-7.25 (3H, m), 7.03 (1H, d, J = 1.86 Hz), 4.42 (1.8H, s), 4.26 (0.2H, s), 3.67-3.60 (2H, m), 3.42-3.32 (1H, m), 3.10 (9H, s), 2.29 (1H, tt, J = 3.42 and 11.63 Hz), 1.93-1.81 (2H, m), 1.74 (1H, d, J = 11.90 Hz), 1.54 (1H, d, J = 10.65 Hz), 1.43-1.28 (2H, m), 1.21-1.07 (1H, m), 1.07-0.94 (1H, m). | Rt = 3.35 min, m/z = 664.2 [M]+ |
| 66 | 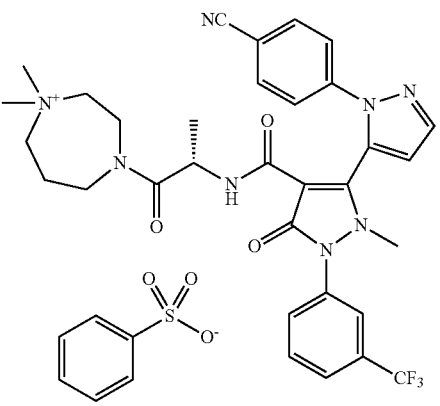 [SMILES: C[C@H](NC(=O)c1c(-c2ccnn2-c2ccc(C#N)cc2)n(C)n(-c2cccc(C(F)(F)F)c2)c1=O)C(=O)N1CCC[N+](C)(C)CC1 ; O=S(=O)([O-])c1ccccc1] | See Ex 17 | Methyl-benzene-sul-phonate | ¹H NMR (400 MHz, d6-DMSO): δ 8.60 (1H, dt, J = 7.13 and 17.13 Hz), 8.03 (1H, d, J = 1.80 Hz), 7.97-7.77 (6H, m), 7.65-7.55 (4H, m), 7.35-7.25 (3H, m), 7.04 (1H, dd, J = 1.88 and 6.99 Hz), 4.65-4.50 (1H, m), 3.92-3.65 (2H, m), 3.65-3.35 (5H, m), 3.33 (3H, s), 3.27 (3H, s), 3.17-3.00 (6H, m), 2.10 (2H, br s), 1.14 (1H, d, J = 6.71 Hz), 0.95 (2H, d, J = 6.72 Hz). | Rt = 3.10 min, m/z = 635.2 [M]+ |

| Ex | Structure | Amine | Quat. reagent | 1H NMR | LC-MS Method 3 |
|---|---|---|---|---|---|
| 67 | 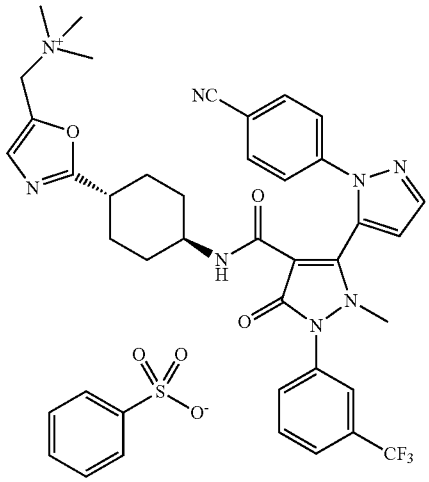 [SMILES: Cn1c(-c2ccnn2-c2ccc(C#N)cc2)c(C(=O)N[C@H]2CC[C@H](c3ncc(C[N+](C)(C)C)o3)CC2)c(=O)n1-c1cccc(C(F)(F)F)c1 ; O=S(=O)([O-])c1ccccc1] | Intermediate M | Methyl-benzene-sulphonate | $^1$H NMR (400 MHz, d6-DMSO): δ 8.04-7.98 (2H, d + d), 7.95-7.79 (6H, m), 7.64-7.56 (4H, m), 7.38-7.36 (1H, s), 7.34-7.27 (3H, m), 7.05-7.03 (1H, d), 4.68-4.64 (2H, s), 3.48-3.37 (1H, m), 3.34-3.30 (9H, m), 3.06-3.01 (3H, s), 2.84-2.74 (1H, m), 2.06-1.96 (2H, m), 1.84-1.76 (1H, m), 1.63-1.43 (3H, m), 1.32-1.18 (1H, m), 1.18-1.04 (1H, m) | Rt = 3.35 min, m/z = 673.3 [M]+ |
| 68 | 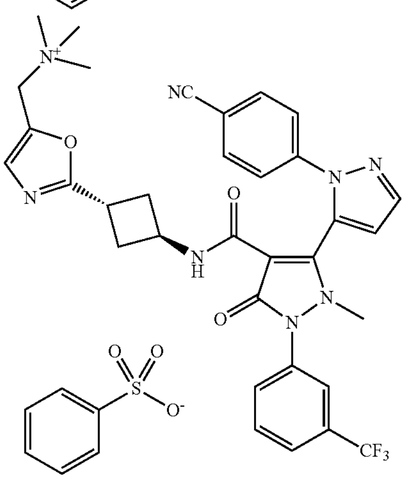 | Intermediate N | Methyl-benzene-sulphonate | $^1$H NMR (400 MHz, d6-DMSO): δ 8.38-8.33 (1H, d), 8.03-8.01 (1H, d), 7.94-7.79 (6H, m), 7.64-7.56 (4H, m), 7.41-7.39 (1H, s), 7.33-7.28 (3H, m), 7.04-7.03 (1H, d), 4.69-4.65 (2H, s), 4.41-4.29 (1H, m), 3.52-3.44 (1H, m), 3.33-3.30 (9H, s) 3.08-3.03 (3H, s), 2.37-2.27 (2H, m), 2.27-2.17 (2H, m) | Rt = 3.27 min, m/z = 645.2 [M]+ |

Example 69

1-(4-{[2'-(4-Cyano-phenyl)-2-methyl-5-oxo-1-(3-trifluoromethyl-phenyl)-2,5-dihydro-1H,2'H-[3,3']bipyrazolyl-4-carbonyl]-amino}-cyclohexylmethyl)-pyridinium bromide

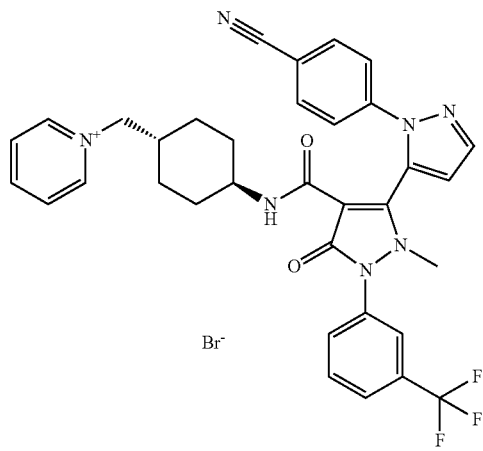 [SMILES: Cn1c(-c2ccnn2-c2ccc(C#N)cc2)c(C(=O)N[C@H]2CC[C@H](C[n+]3ccccc3)CC2)c(=O)n1-c1cccc(C(F)(F)F)c1 ; [Br-]]

Intermediate 69A

2'-(4-Cyano-phenyl)-2-methyl-5-oxo-1-(3-trifluoromethyl-phenyl)-2,5-dihydro-1H,2'H-[3,3']bipyrazolyl-4-carboxylic acid (trans-4-bromomethyl-cyclohexyl)-amide

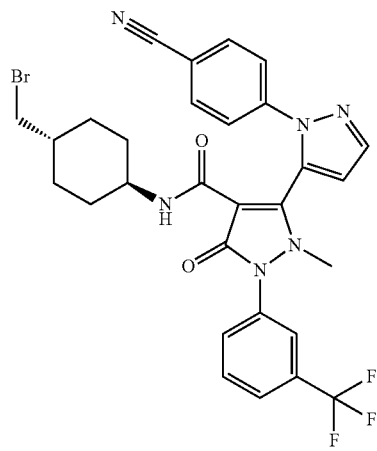 [SMILES: Cn1c(-c2ccnn2-c2ccc(C#N)cc2)c(C(=O)N[C@H]2CC[C@H](CBr)CC2)c(=O)n1-c1cccc(C(F)(F)F)c1]

To a solution of Intermediate G (300 mg, 0.66 mmol) in DCM (6 mL) was added 1 drop of DMF and oxalyl chloride (112 μL, 1.32 mmol) and the reaction mixture stirred at RT for 30 min. The reaction mixture was concentrated in vacuo and the residue suspended in DCM (6 mL). Triethylamine (0.46 mL, 3.31 mmol) and 4-trans bromomethylcyclohexylamine hydrochloride (226 mg, 0.99 mmol) were added. The reaction mixture was stirred at RT for 10 min. The reaction mixture was diluted with water and extracted with DCM (3×10 mL). The combined organic fractions were washed with brine, dried (MgSO$_4$) and concentrated in vacuo. The resultant residue was purified via flash chromatography on silica gel (solvent gradient: 0-5% methanol in ethyl acetate to yield Intermediate 69A as a yellow foam (414 mg, 100%).

LCMS (Method U2): Rt=1.59 min, m/z 627 & 629 [M+H]+

1-(4-{[2'-(4-Cyano-phenyl)-2-methyl-5-oxo-1-(3-trifluoromethyl-phenyl)-2, 5-dihydro-1H,2'H-[3,3'] bipyrazolyl-4-carbonyl]-amino}-cyclohexylmethyl)-pyridinium bromide Intermediate 69A (200 mg, 0.32 mmol) was dissolved in pyridine (3 mL) and the reaction mixture heated at 115° C. for 16 h. The reaction mixture was diluted with diethyl ether and the precipitate formed collected by filtration. The solid residue was crystallized from a mixture of ethyl acetate and methanol and the solid collected by filtration to give the title compound as a white solid (121 mg, 54%).

$^1$H NMR [400 MHz, CDCl$_3$] δ 9.43 (2H, d, J=5.36 Hz), 8.47 (1H, t, J=7.8 Hz), 8.13-8.04 (3H, m), 7.92 (1H, d, J=2.0 Hz), 7.78-7.71 (2H, m), 7.71-7.63 (2H, m), 7.63-7.56 (2H, m), 7.52-7.44 (1H, m), 7.39 (1H, s), 6.92 (1H, d, J=1.7 Hz), 5.00 (1H, dd, J=13.0, 7.1 Hz), 4.84 (1H, dd, J=13.0, 7.6 Hz), 3.72-3.59 (1H, m), 3.03 (3H, s), 2.08-1.92 (2H, m), 1.89-1.82 (1H, m), 1.79-1.72 (1H, m), 1.66-1.62 (1H, m), 1.29-1.04 (4H, m).

LCMS (Method 3) m/z=626 [M]+, Rt=3.51 min.

Example 70

1-(4-{[2'-(4-Cyano-phenyl)-2-methyl-5-oxo-1-(3-trifluoromethyl-phenyl)-2,5-dihydro-1H,2'H-[3,3'] bipyrazolyl-4-carbonyl]-amino}-cyclohexylmethyl)-3-methyl-3H-imidazol-1-ium bromide

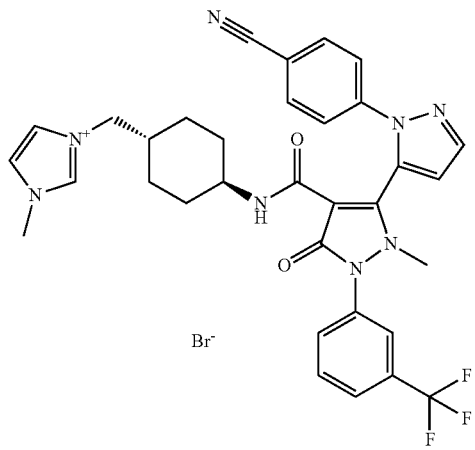 [SMILES: Cn1cc[n+](C[C@H]2CC[C@H](NC(=O)c3c(-c4ccnn4-c4ccc(C#N)cc4)n(C)n(-c4cccc(C(F)(F)F)c4)c3=O)CC2)c1 ; [Br-]]

Intermediate 69A (209 mg, 0.33 mmol) was suspended in N-methylimidazole (2 mL) and the reaction mixture heated at 80° C. for 2 h. The reaction mixture was loaded onto an SCX-NH$_2$ cartridge (5 g) and the cartridge washed with DCM. The product was eluted with methanol and concentrated in vacuo. The resultant residue was triturated with hot ethyl acetate to yield the title compound as a white solid (163 mg, 69%).

$^1$H NMR [400 MHz, CDCl$_3$] δ 10.7 (1H, s), 8.12 (1H, d, J=8.2 Hz), 7.92 (1H, d, J=2.2 Hz), 7.79-7.72 (2H, m), 7.71-7.64 (2H, m), 7.63-7.57 (2H, m), 7.51-7.45 (1H, m), 7.39 (1H, s), 7.29-7.27 (1H, m), 7.23-7.19 (1H, m), 6.92 (1H, d, J=2.2 Hz), 4.23 (1H, dd, J=13.5, 7.1 Hz), 4.15 (1H, dd, J=13.8, 7.3 Hz), 4.11 (3H, s), 3.72-3.60 (1H, m), 3.04 (3H, s), 2.04-1.96 (1H, m), 1.93-1.80 (2H, m), 1.78-1.61 (2H, m), 1.29-1.06 (4H, m).

LCMS (Method 3) m/z=629 [M]+, Rt=3.54 min.

Example 71

2'-(4-Cyano-phenyl)-2-ethyl-5-oxo-1-(3-trifluoromethyl-phenyl)-2,5-dihydro-1H,2'H-[3,3']bipyrazolyl-4-carboxylic acid ethyl ester

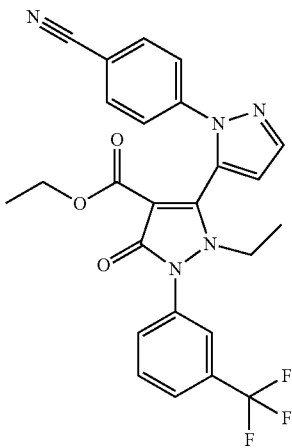 [SMILES: CCOC(=O)c1c(-c2ccnn2-c2ccc(C#N)cc2)n(CC)n(-c2cccc(C(F)(F)F)c2)c1=O]

Intermediate 71A

Bis-BOC protected 2-(4-Cyano-phenyl)-2H-pyrazole-3-carboxylic acid N'-(3-trifluoromethyl-phenyl)-hydrazide

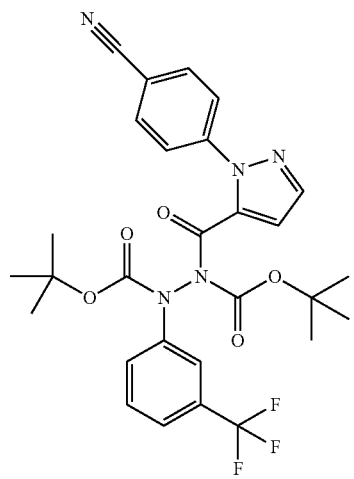 [SMILES: CC(C)(C)OC(=O)N(C(=O)c1ccnn1-c1ccc(C#N)cc1)N(C(=O)OC(C)(C)C)c1cccc(C(F)(F)F)c1]

Prepared from Intermediate B (3 g) by a similar method to that for Intermediate 72D. Yield 4.35 g, 94% after crystallization from diethyl ether.

Intermediate 71B

N'-[2-(4-Cyano-phenyl)-2H-pyrazole-3-carbonyl]-N-(3-trifluoromethyl-phenyl)hydrazinecarboxylic acid tert-butyl ester

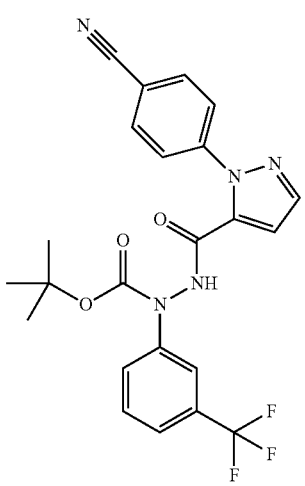 [SMILES: CC(C)(C)OC(=O)N(NC(=O)c1ccnn1-c1ccc(C#N)cc1)c1cccc(C(F)(F)F)c1]

Prepared in a similar manner to Intermediate 72E starting from 3.5 g of Intermediate 71A to afford Intermediate 71B as an off-white foam (2.92 g, quantitative).

LCMS (Method U2) Rt=1.88 min., m/z=472 [M+H]+.

Intermediate 71C

N'-[2-(4-Cyano-phenyl)-2H-pyrazole-3-carbonyl]-N'-ethyl-N-(3-trifluoromethyl-phenyl)-hydrazinecarboxylic acid tert-butyl ester

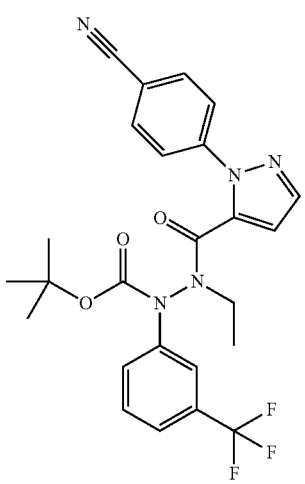 [SMILES: CCN(C(=O)c1ccnn1-c1ccc(C#N)cc1)N(C(=O)OC(C)(C)C)c1cccc(C(F)(F)F)c1]

Synthesized from Intermediate 71B (0.5 g) similarly to Intermediate 72F (using iodoethane in place of iodomethane) to afford, after chromatography, the title compound (456 mg, 86%) as a colorless gum.

LCMS (Method 7) Rt=4.07 min., m/z=500 [M+H]+.

Intermediate 71D 2-(4-Cyano-phenyl)-2H-pyrazole-3-carboxylic acid N-ethyl-N'-(3-trifluoromethyl-phenyl)-hydrazide

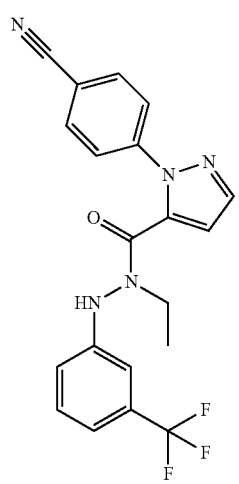 [SMILES: CCN(Nc1cccc(C(F)(F)F)c1)C(=O)c1ccnn1-c1ccc(C#N)cc1]

Intermediate 71C (440 mg, 0.88 mmol) was stirred in DCM (3 mL) with water (25 mg) and TFA (0.5 ml). After 1.5 h a further 0.3 mL of TFA was added. After stirring for a further 2 h, the mixture was diluted with DCM and washed with aqueous sat. NaHCO$_3$.

The organic phase was separated, dried (Na$_2$SO$_4$) and evaporated to give Intermediate 71D (353 mg, 100%).

LCMS (Method 7) Rt=3.51 min., m/z=400 [M+H]+.

Intermediate 71D

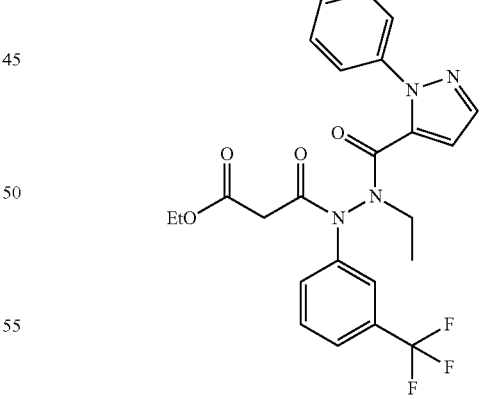

Intermediate 71C (683 mg, 1.71 mmol) was stirred in dry THF (12 mL) and pyridine (164 mg, 2.08 mmol) and DMAP (10 mg, 0.082 mmol) were added, followed by ethyl malonyl chloride (290 mg, 1.93 mmol). The mixture was heated at 50° C. After 5.5 h further quantities of pyridine (164 mg) and ethyl malonyl chloride (290 mg) were added and heating was continued overnight. Third portions of pyridine (164 mg) and ethyl malonyl chloride (290 mg) were added and heating was continued for a further 6 h. After overnight standing the solvent was evaporated and the residue was partitioned between EtOAc and aqueous NaHCO₃. The organic phase was washed with brine, dried (Na₂SO₄), evaporated and purified by SPE chromatography (silica, 25 g) eluting sequentially with 2.5%, 4%, 5% and 10% EtOAc in DCM, to give title compound (257 mg, 29%).

LCMS (Method U2) Rt=1.86 min., m/z=514 [M+H]+, 536 [M+Na]⁺.

2'-(4-Cyano-phenyl)-2-ethyl-5-oxo-1-(3-trifluoromethyl-phenyl)-2,5-dihydro-1H,2'H-[3,3']bipyrazolyl-4-carboxylic acid ethyl ester Intermediate 71D (248 mg, 0.483 mmol) was stirred in EtOH (5 mL) and solid sodium ethoxide (66 mg, 0.967 mmol) was added. After 2.5 h the mixture was partitioned between EtOAc and 10% aqueous citric acid. The organic phase was washed with brine, dried and evaporated (Na₂SO₄). This batch was combined with a smaller scale (28 mg) batch and purified by chromatography on a 10 g silica SPE cartridge, eluting with EtOAc-DCM (1:2, then 1:1) to give 82 mg of a colourless gum which was further purified by a 2$^{nd}$ SPE (5 g) eluting with 20% EtOAc in DCM. The product still contained impurities and therefore was triturated with ether, becoming a white solid. The supernatant was removed and the solid taken up in chloroform and re-precipitated using ether. This process was repeated to give the title compound in good purity (36 mg, 14%).

¹H NMR (400 MHz, d6-DMSO): δ 8.08 (1H, d, J=1.8 Hz), □8.05-8.00 (2H, m), 7.86-7.78 (2H, m), 7.74-7.67 (3H, m), 7.56 (1H, br s), 7.13 (1H, d, J=1.8 Hz), 4.00-3.79 (2H, m), 3.61-3.34 (2H, m), 0.97 (3H, t, J=7.0 Hz), 0.84 (3H, t, J=7.0 Hz).

LCMS (Method 3) Rt 4.49 min., m/z=496.1 [M+H]+.

Example 72

5-[1-(4-Cyano-phenyl)-1H-imidazol-2-yl]-1-methyl-3-oxo-2-(3-trifluoromethyl-phenyl)-2,3-dihydro-1H-pyrazole-4-carboxylic acid cyclopentyl-amide

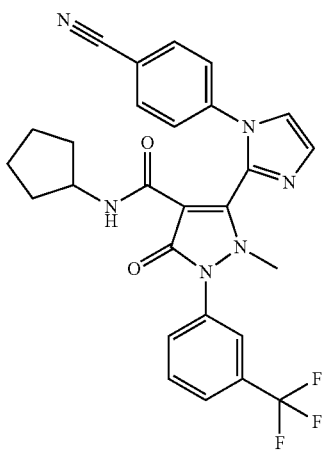 [SMILES: Cn1c(-c2nccn2-c2ccc(C#N)cc2)c(C(=O)NC2CCCC2)c(=O)n1-c1cccc(C(F)(F)F)c1]

Intermediate 72A 1-(4-Cyano-phenyl)-1H-imidazole-2-carboxylate lithium salt

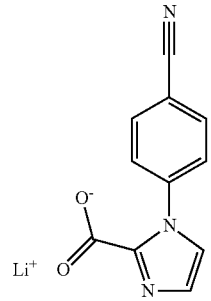 [SMILES: [Li+] ; N#Cc1ccc(-n2ccnc2C(=O)[O-])cc1]

A solution of n-butyl lithium (1.38 mL of a 1.6 M solution in hexanes, 2.2 mmol) was added dropwise to a cold (−75° C.) solution of 4-imidazol-1-yl-benzonitrile in THF (10 ml) in an argon purged flask. The addition was at such a rate that the internal temperature did not exceed −70° C. The mixture was stirred at −75° C. for 1 h and the resultant orange suspension was poured onto ca. 3 g of ground dry ice. The resultant mixture was stirred for 1 h, a thick white precipitate forming over time. The solvent was evaporated in vacuo and the residue was triturated with diethyl ether (15 mL). The solid was recovered by filtration and dried in vacuo to afford Intermediate 72A (429 mg, 1.96 mmol).

¹H NMR (400 MHz, d6-DMSO): δ 7.90 (2H, d, J=8.7 Hz), 7.59 (2H, d, J=8.7 Hz), 7.33 (1H, d, J=1.3 Hz), 6.97 (1H, d, J=1.3 Hz).

Intermediate 72B 1-(4-Cyano-phenyl)-1H-imidazole-2-carboxylic acid methyl ester

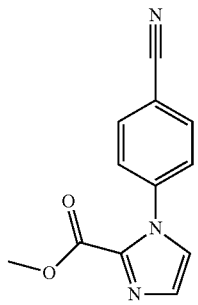 [SMILES: COC(=O)c1nccn1-c1ccc(C#N)cc1]

Iodomethane (1.13 mL, 18.1 mmol) was added to a vigorously stirred mixture of Intermediate 72A (3.18 g, 14.5 mmol) and DMF (45 mL). The mixture was stirred for 18 h and the resultant solution was poured into 1:1 saturated brine:water (450 ml). The mixture was extracted with ethyl acetate (4×50 mL). The combined organic phase was dried (sodium sulfate) and concentrated in vacuo to afford Intermediate 72B (1.40 g, 6.7 mmol) as a white solid.

LCMS (Method U2) Rt=0.98 min, m/z 228.2 [M+H]+.

Intermediate 72C 1-(4-Cyano-phenyl)-1H-imidazole-2-carboxylic acid N'-(3-trifluoromethyl-phenyl)-hydrazide

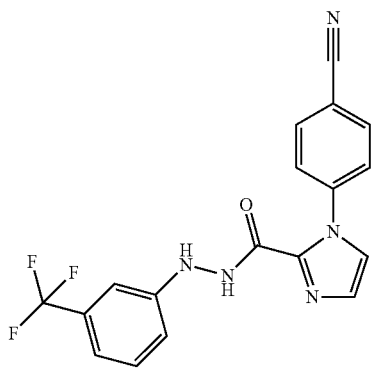 [SMILES: N#Cc1ccc(-n2ccnc2C(=O)NNc2cccc(C(F)(F)F)c2)cc1]

A mixture of 3-trifluoromethyl-phenylhydrazine hydrochloride (1.98 g, 9.3 mmol) and bis(trimethylaluminium)-1,4-diazabicyclo[2.2.2]octane adduct (2.38 g, 9.3 mmol) in dry THF (30 mL) was stirred at 40° C. for 1 h. A suspension of Intermediate 72B (1.40 g, 6.7 mmol) in dry THF (35 mL) was added and the mixture then heated at reflux for 16 h. After allowing to cool to ambient temperature the mixture was quenched by cautious dropwise addition with 4M hydrochloric acid (3.0 mL) and stirred vigorously for 5 minutes then made basic by addition of 5% aqueous potassium carbonate solution (30 mL). The mixture was diluted with water (30 mL) and extracted with ethyl acetate (3×30 mL). The combined organic phase was washed with brine (30 mL), dried (sodium sulfate) and concentrated in vacuo. The residue was purified by flash column chromatography (80 g Si column eluted with 0-25% ethyl acetate in DCM) to afford Intermediate 72C (2.03 g, 5.47 mmol) as a yellow foam.

LCMS (Method U2) Rt=1.39 min, m/z 372.2 [M+H]+.

Intermediate 72D

Bis-BOC-protected-1-(4-cyano-phenyl)-1H-imidazole-2-carboxylic acid N'-(3-trifluoromethyl-phenyl)-hydrazide

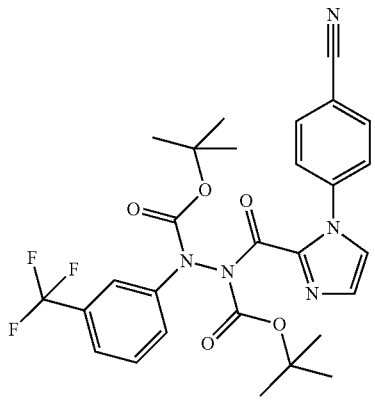 [SMILES: CC(C)(C)OC(=O)N(C(=O)c1nccn1-c1ccc(C#N)cc1)N(C(=O)OC(C)(C)C)c1cccc(C(F)(F)F)c1]

4-Dimethylamino-pyridine (33 mg, 0.27 mmol) was added to a mixture of Intermediate 72C (2.03 g, 5.47 mmol), di-tert-butyl dicarbonate (1.91 g, 8.75 mmol), triethylamine (1.90 mL, 13.68 mmol) and dry THF (40 mL). The mixture was heated at 50° C. for 60 h. The mixture was concentrated in vacuo and the residue was purified by flash column chromatography (40 g silica cartridge eluted with 0-40% ethyl acetate in pentane) to afford Intermediate 72D (2.36 g, 4.13 mmol) as a white solid.

LCMS (Method U2) Rt=1.74 min, m/z 572.3 [M+H]+.

Intermediate 72E

N'-[1-(4-Cyano-phenyl)-1H-imidazole-2-carbonyl]-N-(3-trifluoromethyl-phenyl)-hydrazinecarboxylic acid tert-butyl ester

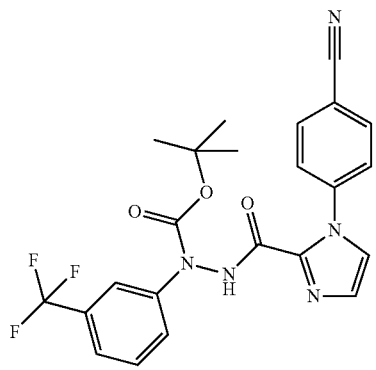 [SMILES: CC(C)(C)OC(=O)N(NC(=O)c1nccn1-c1ccc(C#N)cc1)c1cccc(C(F)(F)F)c1]

Magnesium perchlorate (177 mg, 0.79 mmol) was added to a solution of Intermediate 72D (2.36 g, 4.13 mmol) in dry acetonitrile (60 mL). The mixture was stirred and heated at 50° C. for 2 h. The cold mixture was concentrated to a small volume and diluted with saturated aqueous sodium hydrogen carbonate solution (25 mL). The mixture was extracted with ethyl acetate (3×25 mL). The combined organic phase was dried (sodium sulfate) and concentrated in vacuo to afford Intermediate 72E (1.99 g, ca. quant.) as a yellow foam.

LCMS (Method U2) Rt=1.61 min, m/z 472.2 [M+H]+.

Intermediate 72F

N'-[1-(4-Cyano-phenyl)-1H-imidazole-2-carbonyl]-N'-methyl-N-(3-trifluoromethyl-phenyl)-hydrazinecarboxylic acid tert-butyl ester

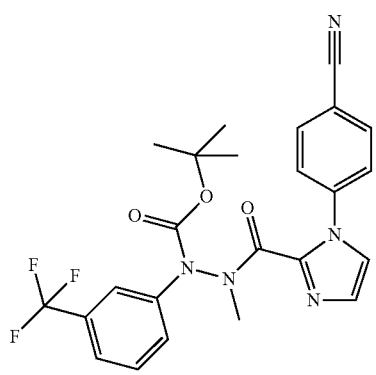 [SMILES: CN(C(=O)c1nccn1-c1ccc(C#N)cc1)N(C(=O)OC(C)(C)C)c1cccc(C(F)(F)F)c1]

Sodium hydride (110 mg of a 60% dispersion in mineral oil, 2.76 mmol) was added to a solution of Intermediate 72E (1.00 g, 2.12 mmol) in dry DMF (20 mL). The mixture was stirred for 1 h then treated with iodomethane (175 μL, 2.82 mmol). The mixture was stirred for 2 h then diluted with brine:water 2:1 (200 mL). The mixture was extracted with ethyl acetate (3×25 mL). The combined organic phase was dried (sodium sulfate) and concentrated in vacuo. The residue was purified by flash column chromatography (40 g Si cartridge eluted with 0-10% ethyl acetate in DCM) to afford Intermediate 72F (0.82 g, 1.69 mmol) as a white foam.

LCMS (Method U2) Rt=1.63 min, m/z 486.2 [M+H]+.

Intermediate 72G 1-(4-Cyano-phenyl)-1H-imidazole-2-carboxylic acid N-methyl-N'-(3-trifluoromethyl-phenyl)-hydrazide

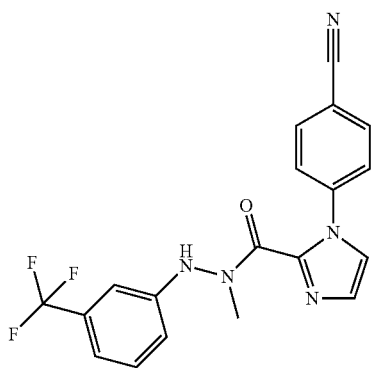 [SMILES: CN(Nc1cccc(C(F)(F)F)c1)C(=O)c1nccn1-c1ccc(C#N)cc1]

A mixture of Intermediate 72F (0.82 g, 1.69 mmol) and 4M hydrogen chloride in dioxane (4.2 mL, 16.9 mmol) was stirred for 2 h then concentrated in vacuo. The residue was passed through a 20 g SCX-2 cartridge washing with dichloromethane then dichloromethane methanol and eluting with 2M methanolic ammonia in dichloromethane. Concentration of the appropriate fractions gave the crude product which was further purified by flash column chromatography (40 g Si cartridge eluted with 0-4% 2M methanolic ammonia in dichloromethane) to afford Intermediate 72G (569 mg, 1.48 mmol) as an off white foam.

LCMS (Method U2) Rt=1.35 min, m/z 386.2 [M+H]+.

Intermediate 72H

3-[N'-[1-(4-Cyano-phenyl)-1H-imidazole-2-carbonyl]-N'-methyl-N-(3-trifluoromethyl-phenyl)-hydrazino]-3-oxo-propionic acid ethyl ester

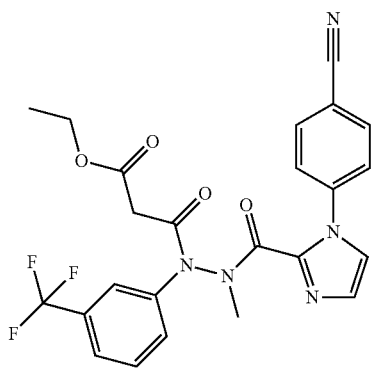 [SMILES: CCOC(=O)CC(=O)N(c1cccc(C(F)(F)F)c1)N(C)C(=O)c1nccn1-c1ccc(C#N)cc1]

A mixture of Intermediate 72G (569 mg, 1.48 mmol), ethyl malonyl chloride (0.202 mL, 1.63 mmol), pyridine (0.144 mL, 1.78 mmol), 4-dimethylamino-pyridine (9 mg, 0.07 mmol) and dry tetrahydrofuran (15 mL) was stirred at 50° C. A further aliquot of ethyl malonyl chloride (0.208 mL, 1.63 mmol) and pyridine (0.144 mL, 1.78 mmol) were added after 16 h. Heating was discontinued after a further 3 h. The mixture was concentrated in vacuo. The residue was taken into ethyl acetate (30 mL) and washed with saturated aqueous sodium hydrogen carbonate (25 mL) and brine (25 mL) then dried (sodium sulfate) and concentrated in vacuo. The residue was purified by flash column chromatography (40 g Si cartridge eluted with 0-25% ethyl acetate in DCM) to afford Intermediate 72H (0.51 g, 1.02 mmol) as a white foam.

LCMS (Method U2) Rt=1.48 min, m/z 500.2 [M+H]+.

Intermediate 72I

5-[1-(4-Cyano-phenyl)-1H-imidazol-2-yl]-1-methyl-3-oxo-2-(3-trifluoromethyl-phenyl)-2,3-dihydro-1H-pyrazole-4-carboxylic acid ethyl ester

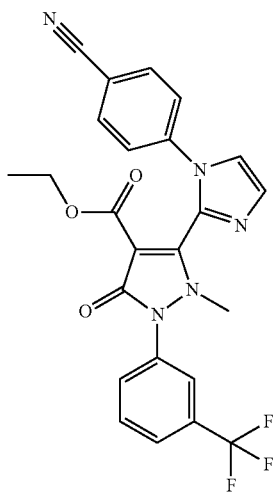 [SMILES: CCOC(=O)c1c(-c2nccn2-c2ccc(C#N)cc2)n(C)n(-c2cccc(C(F)(F)F)c2)c1=O]

Sodium ethoxide (120 mg, 1.76 mmol) was added to a stirred suspension of Intermediate 72H (440 mg, 0.88 mmol) in absolute ethanol (8 mL). The mixture was stirred at RT for 16 h. A second aliquot of sodium ethoxide (30 mg, 0.44 mmol) was added and the mixture was heated at 40° C. for 3 h. The cold mixture was diluted with water (10 mL) and extracted with ethyl acetate (15 mL). The organic phase was washed with 10% aqueous citric acid (15 mL). The aqueous phases were combined and extracted with ethyl acetate (10 mL). The combined organic phase was dried (sodium sulfate) and concentrated in vacuo. The residue was purified by flash column chromatography (25 g Si cartridge eluted with 0-100% ethyl acetate in dichloromethane) to afford Intermediate 72I (372 mg, 0.77 mmol) as a white solid.

LCMS (Method U2) Rt=1.24 min, m/z 482.2 [M+H]+.

Intermediate 72J.

5-[1-(4-Cyano-phenyl)-1H-imidazol-2-yl]-1-methyl-3-oxo-2-(3-trifluoromethyl-phenyl)-2,3-dihydro-1H-pyrazole-4-carboxylic acid

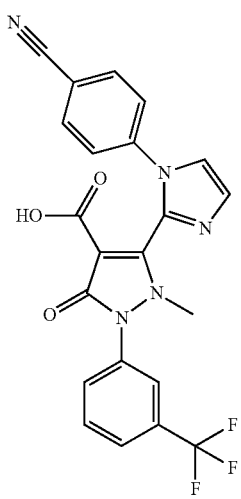 [SMILES: Cn1c(-c2nccn2-c2ccc(C#N)cc2)c(C(=O)O)c(=O)n1-c1cccc(C(F)(F)F)c1]

A solution of lithium hydroxide hydrate (162 mg, 3.86 mmol) in water (5 mL) was added to a solution of Intermediate 72I (372 mg, 0.77 mmol) in tetrahydrofuran (16 mL). The mixture was stirred at RT for 21 h. The mixture was then treated with 5% aqueous potassium hydrogen sulfate solution (20 mL) and extracted with ethyl acetate (2×15 mL). The combined organic phase was washed with brine (15 mL), dried (sodium sulfate) and concentrated in vacuo to afford Intermediate 72J (350 mg, ca quantitative) as a white solid.

LCMS (Method U2) Rt=1.17 min, m/z 454.1 [M+H]+.

5-[1-(4-Cyano-phenyl)-1H-imidazol-2-yl]-1-methyl-3-oxo-2-(3-trifluoromethyl-phenyl)-2,3-dihydro-1H-pyrazole-4-carboxylic acid cyclopentyl-amide Carbonyl diimidazole (53 mg, 0.325 mmol) was added to a suspension of Intermediate 72J (113 mg, 0.25 mmol) in dry tetrahydrofuran (2.0 mL). The mixture was stirred at RT for 2 h then cyclopentyl amine (49 μL, 0.5 mmol) was added. The mixture was stirred for 1 h. The resultant solution was diluted with ethyl acetate (25 mL) and washed with water (2×10 mL) then brine (10 mL). The organic phase was dried (sodium sulfate) and concentrated in vacuo. The residue was purified by flash column chromatography (2 g Si-II column eluted ethyl acetate) to afford the title compound (100 mg, 0.19 mmol) as a white solid.

$^1$H NMR (400 MHz, CDCl3): δ 7.95 (1H, d J=7.2 Hz), 7.76-7.58 (6H, m), 7.47 (1H, d, J=1.3 Hz), 7.43-7.38 (3H, m), 4.04-3.94 (1H, m), 3.37 (3H, s), 1.88-1.72 (2H, m), 1.68-1.46 (4H, m), 1.42-1.30 (1H, m), 1.24-1.14 (1H, m).

LCMS (Method 3): Rt=4.50 min, m/z 521.3 [M+H]+

Biological Assay

Compounds of the present invention were tested for potency in a human neutrophil elastase (HNE) enzyme activity assay.

HNE Enzyme Assay

Assays were performed in 96-well plates in a total assay volume of 100 μL. The final concentration of elastase enzyme (human leukocyte elastase, Sigma E8140) was 0.00072 U/mL. The peptide substrate (MeOSuc-Ala-Ala-Pro-Val-AMC, Calbiochem #324740) was used at a final concentration of 100 μM. The final concentration of DMSO was 1% in the assay buffer (0.05M Tris.HCl, 0.1M NaCl, 0.1M CaCl$_2$, 0.0005% brij-35, pH 7.5). The enzymatic reaction was started by addition of the enzyme and incubated at 25° C. for 30 minutes. After incubation, the reaction was stopped by addition of soybean trypsin inhibitor (Sigma T9003) at a final concentration of 50 μg/well. Fluorescence was measured using a Molecular Devices fluorescence plate reader using 380 nm excitation and 460 nm emission wavelengths.

A dose response to each compound was performed and the effect of compound in each experiment was expressed as a percentage inhibition of the control enzyme fluorescence. Dose response curves were plotted and compound potency (IC$_{50}$) was determined. Compounds were tested in at least two separate experiments. IC$_{50}$ values for tested Examples, representative of the invention, are shown in Table 1:

TABLE 1

| Example | HNE inhibition |
|---|---|
| 1, 3, 4, 5, 6, 7, 8, 9, 10, 11, 12, 13, 14, 15, 16, 17, 18, 19, 22, 23, 24, 25, 26, 27, 28, 30, 31, 32, 33, 35, 36, 37, 38, 39, 40, 41, 42, 43, 44, 45, 46, 47, 48, 49, 50, 51, 53, 54, 55, 56, 57, 58, 59, 60, 61, 62, 63, 64, 65, 66, 67, 68, 69, 70, 71, 72 | ++++ |
| 2, 20, 21, 29, 34, 52, | +++ |

In the table above, HNE enzyme inhibition (IC$_{50}$ values) are indicated as follows:
1-10 nM '+++';
<1 nM '++++'.

LPS/fMLP Model

Male Sprague-Dawley rats were lightly anaesthetized and given vehicle (for example 0.2% Tween 80 in saline for wet formulation studies or lactose for dry powder studies) or compound, i.t., at the desired pre-dose time (prior to fMLP administration e.g. 1 h, 12 h or 24 h)

Four hours prior to fMLP administration, animals were lightly anaesthetized and given LPS (for example 0.5 ml/kg of 20 μg/ml PBS solution) by the i.t. route.

Thirty to forty minutes prior to fMLP-administration, animals were terminally anaesthetized with urethane. Animals were placed on a heat mat and anaesthesia was maintained until animals were killed and subjected to BAL.

Four hours after LPS-challenge, rats were given fMLP (for example 0.5 ml/kg of 0.6 mg/ml PBS solution) by the i.t. route.

Animals were killed one hour after fMLP-administration, the trachea cannulated and BALF collected. An elastase activity assay was performed to determine the level of elastase present in the BALF.

HNE Model

Male Sprague-Dawley rats were lightly anaesthetized and given vehicle (for example 0.2% Tween 80 in saline for wet formulation studies or lactose for dry powder studies) or compound, i.t.

Thirty to forty minutes prior to HNE-administration, animals were terminally anaesthetized with urethane. Animals were placed on a heat mat and anaesthesia was maintained until animals were killed for BAL.

Three hours after compound/vehicle administration, animals were given PBS as control or HNE (for example 0.1 ml of a 1000 U/ml solution in PBS) by the i.t. route.

Animals were killed one hour after iHNE-administration, the trachea cannulated and BALF collected. Red blood cells accumulation in BALF was assessed spectrophotometrically, as a measure of BALF hemoglobin content.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A compound of formula (I):

[Chemical structure of formula (I)]

wherein
Z is —O— or —NH;
W is —H or $(C_1-C_4)$alkyl;
A is:

[Three heterocyclic structures: pyrazole, imidazole, triazole]

X is —$(C_1-C_6)$alkyl, —$(C_2-C_6)$alkylene-$NR_dR_e$, linear or branched —$(C_1-C_4)$alkylene-aryl, linear or branched —$(C_2-C_4)$alkylene-heteroaryl,

[Chemical structures]

-continued

[Chemical structures]

$R_1$ is:

[Chemical structures]

n is an integer from 1 to 4;
m is an integer from 1 to 4;
t is 0 or an integer from 1 to 4;
y is an integer from 1 to 4;
w is an integer from 1 to 4;
$R_2$ is —H or linear or branched —$(C_1-C_4)$alkyl;
$R_3$ is —H, linear or branched —$(C_1-C_4)$alkyl; or
$R_2$ and $R_3$ may form together a —$(C_3-C_6)$cycloalkyl;
$R_4$ is heteroaryl, -arylene-$(C_1-C_4)$alkylene-$NR_dR_e$, heteroarylene-$(C_1-C_4)$alkylene-$NR_dR_e$, or

[Chemical structures]

$R_5$ is —H, —$(CH_2)_t$-heteroaryl, aryl-$(C_1-C_4)$alkylene-oxy-, linear or branched $(C_1-C_4)$alkyl-OC(O)—NH—, —$(CH_2)_t$—$NR_dR_e$, —C(O)—N$(R_{10})(C_1-C_4)$alkylene-$NR_dR_e$, —C(O)O$(C_1-C_4)$alkylene-$NR_dR_e$, —O—C(O)—$(C_1-C_4)$alkylene-$NR_dR_e$, —$(CH_2)_t$NHC(O)—$(C_1-C_4)$alkylene-$NR_dR_e$, or

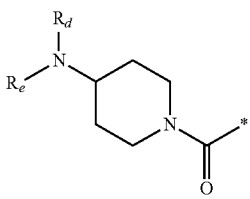

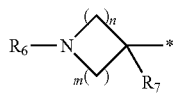

R<sub>6</sub> is —H, —(C<sub>1</sub>-C<sub>4</sub>)alkyl, aryl-(C<sub>1</sub>-C<sub>4</sub>)alkylene-OC(O)—, CF<sub>3</sub>C(O)—, aryl-(C<sub>1</sub>-C<sub>4</sub>)alkylene-, linear or branched (C<sub>1</sub>-C<sub>4</sub>)alkyl-OC(O)—, —C(O)—(C<sub>1</sub>-C<sub>4</sub>)alkylene-NR$_d$R$_e$, —C(O)-heterocycloalkyl, —C(O)O—(C<sub>1</sub>-C<sub>4</sub>)alkylene-NR$_d$R$_e$, or —C(O)—N(R<sub>10</sub>)(C<sub>1</sub>-C<sub>4</sub>)alkylene-NR$_d$R$_e$;

R$_d$ is —H or —(C<sub>1</sub>-C<sub>4</sub>)alkyl;
R$_e$ is —H or —(C<sub>1</sub>-C<sub>4</sub>)alkyl;
R<sub>7</sub> is —H or —(C<sub>1</sub>-C<sub>4</sub>)alkyl;
R<sub>8</sub> is —H or —(C<sub>1</sub>-C<sub>4</sub>)alkyl;
R<sub>9</sub> is -heterocycloalkyl, heterocycloalkyl-(C<sub>1</sub>-C<sub>4</sub>)alkylene-, or (C<sub>1</sub>-C<sub>4</sub>)alkylene-NR$_d$R$_e$ ;
R<sub>10</sub> is —H or —(C<sub>1</sub>-C<sub>4</sub>)alkyl;

wherein any of such heterocycloalkyl, aryl, heteroaryl, heterocycloalkyl-(C<sub>1</sub>-C<sub>4</sub>)alkylene- and aryl-(C<sub>1</sub>-C<sub>4</sub>)alkylene may be optionally substituted by one or more groups independently selected from the group consisting of —(C<sub>1</sub>-C<sub>4</sub>)alkyl and —OR<sub>7</sub>, and wherein * and # indicate the points of attachment for the radical groups to the rest of the molecule, or a pharmaceutically acceptable salt thereof.

2. A compound or salt according to claim 1, wherein X is

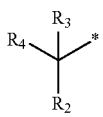

R<sub>6</sub> is —H, —(C<sub>1</sub>-C<sub>4</sub>)alkyl, —C(O)—(C<sub>1</sub>-C<sub>4</sub>)alkylene-NR$_d$R$_e$, or —C(O)-heterocycloalkyl, wherein the heterocycloalkyl may be optionally substituted by one or more —(C<sub>1</sub>-C<sub>4</sub>)alkyl groups; R$_d$ and R$_e$ are independently —H or —(C<sub>1</sub>-C<sub>4</sub>)alkyl; n is 2; m is 2; and R<sub>7</sub> is —H or —(C<sub>1</sub>-C<sub>4</sub>)alkyl.

3. A compound or salt according to claim 1, wherein X is

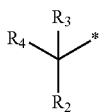

R<sub>2</sub> and R<sub>3</sub> are independently —H or linear or branched —(C<sub>1</sub>-C<sub>4</sub>)alkyl; R<sub>4</sub> is heteroaryl optionally substituted by one or more —(C<sub>1</sub>-C<sub>4</sub>)alkyl.

4. A compound or salt according to claim 1, wherein X is

R<sub>2</sub> and R<sub>3</sub> are independently —H or linear or branched —(C<sub>1</sub>-C<sub>4</sub>)alkyl; R<sub>4</sub> is -heteroarylene-(C<sub>1</sub>-C<sub>4</sub>)alkylene-NR$_d$R$_e$ ; R$_d$ and R$_e$ are independently —H or —(C<sub>1</sub>-C<sub>4</sub>)alkyl.

5. A compound or salt according to claim 1, wherein X is

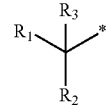

R<sub>2</sub> is —H or linear or branched —(C<sub>1</sub>-C<sub>4</sub>)alkyl; R<sub>3</sub> is —H; R<sub>1</sub> is

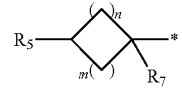

R<sub>7</sub> is —H or —(C<sub>1</sub>-C<sub>4</sub>)alkyl; t is 0; n is 2; and m is 2.

6. A compound or salt according to claim 1, wherein X is

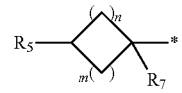

R<sub>10</sub> is —H or —(C<sub>1</sub>-C<sub>4</sub>)alkyl; n is 1 or 2; m is 1 or 2; and R<sub>7</sub> is —H.

7. A compound or salt according to claim 1, wherein X is

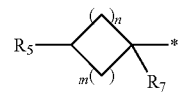

t is 0 or 1, n is 2, m is 2, and R<sub>7</sub> is —H.

8. A compound as claimed in claim 1, wherein X is

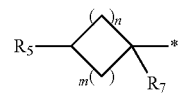

n is 1 or 2, m is 1 or 2, R<sub>7</sub> is —H, and R$_d$ and R$_e$ are each independently —(C<sub>1</sub>-C<sub>4</sub>)alkyl.

9. A compound which is selected from the group consisting of

2'-(4-cyano-phenyl)-2-methyl-5-oxo- 1-(3-trifluoromethyl-phenyl)-2,5-dihydro-1H,2'H-[3,3']bipyrazolyl-4-carboxylic acid ethyl ester;

2'-(4-cyano-phenyl)-2-methyl-5-oxo-1-(3 -trifluoromethyl-phenyl)-2,5-dihydro-1H,2'H- [3,3']bipyrazolyl-4-carboxylic acid (1-methyl-piperidin-4-yl)-amide;

2'-(4-cyano-phenyl)-2-methyl-5-oxo-1-(3-trifluoromethyl-phenyl)-2,5-dihydro-1H,2'H-[3,3']bipyrazolyl-4-carboxylic acid ethylamide;

(3aS,5R,6aR)-5- {[2'-(4-cyano-phenyl)-2-methyl-5-oxo-1-(3-trifluoromethyl-phenyl)-2,5-dihydro-1H,2'H-[3,3']bipyrazolyl-4-carbonyl]-amino}-hexahydro-cyclopenta[c]pyrrole-2-carboxylic acid tert-butyl ester;

2'-(4-cyano-phenyl)-2-methyl-5-oxo-1-(3-trifluoromethyl-phenyl)-2,5-dihydro-1H,2H-[3,3'bipyrazolyl-4-carboxylic acid [(S)-1-(5-dimethylaminomethyl-oxazol-2-yl)-ethyl]-amide;

2'-(4-cyano-phenyl)-2-methyl-5-oxo-1-(3-trifluoromethyl-phenyl)-2,5-dihydro-1H,2'H-{3,3'bipyrazolyl-4-carboxylic acid [1-(2-dimethylamino-acetyl)-piperidin-4-yl]-amide;

2'-(4-cyano-phenyl)-2-methyl-5-oxo-1-(3-trifluoromethyl-phenyl)-2,5-dihydro-1H,2'H-[3,3']bipyrazolyl-4-carboxylic acid {(S)-1-[methyl-(1-methyl-piperidin-4-ylmethyl)-carbamoyl]-ethyl}-amide;

2'-(4-cyano-phenyl)-2-methyl-5-oxo-1-(3-trifluoromethyl-phenyl)-2,5-dihydro-1H,2'H-[3,3']bipyrazolyl-4- carboxylic acid [(S)-1-(5-dimethylaminomethyl-[1,3,4]oxadiazol-2-yl)-ethyl]-amide;

2'-(4-cyano-phenyl)-2-methyl-5-oxo-1-(3-trifluoromethyl-phenyl)-2,5-dihydro-1H,2'H-[3,3']bipyrazolyl-4-carboxylic acid {1-methyl-1-[methyl-(1-methyl-piperidin-4-ylmethyl)-carbamoyl]-ethyl}-amide;

2'-(4-cyano-phenyl)-2-methyl-5-oxo-1-(3-trifluoromethyl-phenyl)-2,5-dihydro-1H,2'H-[3,3']bipyrazolyl-4-carboxylic acid [(S)-1-(5-dimethylaminomethyl-oxazol-2-yl)-2-methyl-ethyl]-amide;

2'-(4-cyano-phenyl)-2-methyl-5-oxo-1-(3-trifluoromethyl-phenyl)-2,5-dihydro-1H,2'H-[3,3']bipyrazolyl-4-carboxylic acid [(S)-1-(5-dimethylaminomethyl-oxazol-2-yl)-2-methyl-propyl]-amide;

2'-(trans-4-cyano-phenyl)-2-methyl-5-oxo-1-(3-trifluoromethyl-phenyl)-2,5-dihydro-1H,2'H-[3,3']bipyrazolyl-4-carboxylic acid [4-(1-methyl-piperidin-4-ylcarbamoyl)-cyclohexyl]-amide;

trans-4-{[2'-(4-cyano-phenyl)-2-methyl-5-oxo-1-(3-trifluoromethyl-phenyl)-2,5-dihydro-1H,2'H-[3,3']bipyrazolyl-4-carbonyl]-amino}-cyclohexanecarboxylic acid 1-methyl-piperidin-4-yl ester 2'-(trans-4-cyano-phenyl)-2-methyl-5-oxo-1-(3-trifluoromethyl-phenyl)-2,5-dihydro-1H,2'H-[3,3']bipyrazolyl-4-carboxylic acid [4-(4-dimethylamino-piperidine-1-carbonyl)-cyclohexyl]-amide;

trans-4-{[2'-(4-cyano-phenyl)-2-methyl-5-oxo-1-(3-trifluoromethyl-phenyl)-2,5-dihydro-1H,2'H-[3,3']bipyrazolyl-4-carbonyl]-amino}-cyclohexanecarboxylic acid 2-dimethylamino-ethyl ester dimethylamino-acetic acid trans-4-{[2'-(4-cyano-phenyl)-2-methyl-5-oxo-1-(3-trifluoromethyl-phenyl)-2,5-dihydro-1H,2'H-[3,3']bipyrazolyl-4-carbonyl]-amino}-cyclohexyl ester;

2'-(4-cyano-phenyl)-2-methyl-5-oxo-1-(3-trifluoromethyl-phenyl)-2,5-dihydro-1H,2'H-[3,3']bipyrazolyl-4-carboxylic acid [(S)-1-methyl-2-(4-methyl-[1,4]diazepan-1-yl)-2-oxo-ethyl]-amide;

2'-(4-cyano-phenyl)-2-ethyl-5-oxo-1-(3-trifluoromethyl-phenyl)-2,5-dihydro-1H,2'H-[3,3'bipyrazolyl-4-carboxylic acid ethyl ester; and 5-[1-(4-cyano-phenyl)-1H-imidazol-2-yl]-1-methyl-3-oxo-2-(3-trifluoromethyl-phenyl)-2,3-dihydro-1H-pyrazole-4-carboxylic acid cyclopentyl-amide.

or a pharmaceutically acceptable salt of said compound.

10. A pharmaceutical composition, comprising a compound or salt according to claim 1 and a pharmaceutically acceptable carrier or excipient.

11. A pharmaceutical composition according to claim 10, which is adapted for oral administration or administration by the pulmonary route.

12. A method of treatment of a disease or condition in which HNE is implicated, comprising administering to a subject in need thereof an effective amount of a compound or salt according to claim 1, wherein said disease or condition is chronic obstructive pulmonary disease, bronchiectasis, chronic bronchitis, lung fibrosis, pneumonia, acute respiratory distress syndrome, pulmonary emphysema, smoking-induced emphysema, cystic fibrosis, asthma, rhinitis, psoriasis, atopic dermatitis, non-atopic dermatitis, Crohn's disease, ulcerative colitis, or irritable bowel disease.

13. A method according to claim 12, wherein said disease or condition is chronic obstructive pulmonary disease, bronchiectasis, chronic bronchitis, lung fibrosis, pneumonia, acute respiratory distress syndrome, pulmonary emphysema, smoking-induced emphysema, or cystic fibrosis.

14. A method according to claim 12 wherein said disease or condition is asthma, rhinitis, psoriasis, atopic dermatitis, non-atopic dermatitis, Crohn's disease, ulcerative colitis, or irritable bowel disease.

15. A compound or salt according to claim 1, which is a an acid addition salt of a compound which contains a —$NR_dR_e$ group or a —$NR_6$— group.

* * * * *